United States Patent
Ahn et al.

(10) Patent No.: US 9,321,728 B2
(45) Date of Patent: Apr. 26, 2016

(54) BETA-ALANINE DERIVATIVES, PHARMACEUTICALLY ACCEPTABLE SALTS THEREOF, AND PHARMACEUTICAL COMPOSITION COMPRISING SAME AS ACTIVE INGREDIENT

(71) Applicants: KOREA RESEARCH INSTITUTE OF CHEMICAL TECHNOLOGY, Daejeon (KR); HANDOK PHARMACEUTICALS CO., LTD., Seoul (KR)

(72) Inventors: Jin Hee Ahn, Daejeon (KR); H. S. Pagire, Daejeon (KR); Sang Dal Rhee, Daejeon (KR); Ki Young Kim, Daejeon (KR); Won Hoon Jung, Daejeon (KR); Myung-Ae Bae, Daejeon (KR); Jin Sook Song, Daejeon (KR); Kwang-Rok Kim, Daejeon (KR); Hyun Jung Kwak, Daejeon (KR)

(73) Assignees: KOREA RESEARCH INSTITUTE OF CHEMICAL TECHNOLOGY, Daejeon (KR); HANDOK PHARMACEUTICALS CO., LTD., Seoul (KR)

( * ) Notice: Subject to any disclaimer, the term of this patent is extended or adjusted under 35 U.S.C. 154(b) by 0 days.

(21) Appl. No.: 14/396,663

(22) PCT Filed: Apr. 25, 2013

(86) PCT No.: PCT/KR2013/003557
§ 371 (c)(1),
(2) Date: Oct. 23, 2014

(87) PCT Pub. No.: WO2013/162298
PCT Pub. Date: Oct. 31, 2013

(65) Prior Publication Data
US 2015/0329504 A1 Nov. 19, 2015

(30) Foreign Application Priority Data

Apr. 25, 2012 (KR) ........................ 10-2012-0043189
Apr. 25, 2013 (KR) ........................ 10-2013-0045811

(51) Int. Cl.
| | | |
|---|---|---|
| C07D 263/32 | (2006.01) |
| C07D 231/12 | (2006.01) |
| C07D 209/20 | (2006.01) |
| C07D 271/06 | (2006.01) |
| C07D 277/30 | (2006.01) |
| C07D 261/08 | (2006.01) |
| C07D 213/56 | (2006.01) |
| C07D 239/26 | (2006.01) |
| C07D 213/82 | (2006.01) |
| A61K 45/06 | (2006.01) |
| A61K 31/421 | (2006.01) |
| A61K 31/415 | (2006.01) |
| A61K 31/27 | (2006.01) |
| C07C 237/12 | (2006.01) |
| A61K 31/216 | (2006.01) |
| A61K 31/403 | (2006.01) |

(Continued)

(52) U.S. Cl.
CPC ............ *C07D 213/82* (2013.01); *A61K 31/167* (2013.01); *A61K 31/216* (2013.01); *A61K 31/27* (2013.01); *A61K 31/403* (2013.01); *A61K 31/415* (2013.01); *A61K 31/421* (2013.01); *A61K 45/06* (2013.01); *C07C 237/04* (2013.01); *C07C 237/12* (2013.01); *C07C 237/22* (2013.01); *C07C 271/22* (2013.01); *C07D 209/20* (2013.01); *C07D 209/42* (2013.01); *C07D 213/56* (2013.01); *C07D 231/12* (2013.01); *C07D 231/14* (2013.01); *C07D 239/26* (2013.01); *C07D 261/08* (2013.01); *C07D 261/10* (2013.01); *C07D 263/32* (2013.01); *C07D 263/34* (2013.01); *C07D 271/06* (2013.01); *C07D 277/30* (2013.01); *C07D 277/56* (2013.01); *C07D 417/12* (2013.01); *C07B 2200/07* (2013.01); *C07C 2101/14* (2013.01)

(58) Field of Classification Search
None
See application file for complete search history.

(56) References Cited

FOREIGN PATENT DOCUMENTS

| WO | 99/26921 A1 | 6/1999 |
| WO | 03/099765 A1 | 12/2003 |
| WO | 2009/016462 A2 | 2/2009 |
| WO | 2011/123401 A1 | 10/2011 |

OTHER PUBLICATIONS

Robert L. Dow, et al; "Discovery of PF-04620110, a Potent, Selective, and Orally Bioavailable Inhibitor of DGAT-1", ACS Medicinal Letters, vol. 2, pp. 407-412, Published Mar. 18, 2011.

(Continued)

*Primary Examiner* — Laura L. Stockton
(74) *Attorney, Agent, or Firm* — Ladas & Parry LLP

(57) ABSTRACT

The present invention relates to a beta-alanine derivative, pharmaceutically acceptable salts thereof, and a pharmaceutical composition including the same as an active ingredient. The novel beta-alanine derivative and pharmaceutically acceptable salts thereof according to the present invention may effectively inhibit the activity of DGAT1, which is an enzyme serving as a catalyst in the final step of the synthesis of neutral lipids, to thereby be effectively used as a pharmaceutical composition for preventing or treating various lipid metabolism-related disorders selected from the group consisting of obesity, dyslipidemia, fatty liver, insulin resistance syndrome, and hepatitis.

8 Claims, No Drawings

(51) Int. Cl.
*A61K 31/167* (2006.01)
*C07C 271/22* (2006.01)
*C07D 231/14* (2006.01)
*C07D 417/12* (2006.01)
*C07D 261/10* (2006.01)
*C07D 263/34* (2006.01)
*C07C 237/04* (2006.01)
*C07C 237/22* (2006.01)
*C07D 277/56* (2006.01)
*C07D 209/42* (2006.01)

(56) References Cited

OTHER PUBLICATIONS

Jesper Lau, et al; "New β-Alanine Derivatives are Orally Available Glucagon Receptor Antagonists", J. Med. Chem. vol. 50, pp. 113-128, Published on Web Jan. 4, 2007.
International Search report dated Aug. 5, 2013; PCT/KR2013/003557.
Extended European Search Report dated Nov. 20, 2015; Appln. 13781273.1-1451/2842938 PCT/KR2013003557.

BETA-ALANINE DERIVATIVES, PHARMACEUTICALLY ACCEPTABLE SALTS THEREOF, AND PHARMACEUTICAL COMPOSITION COMPRISING SAME AS ACTIVE INGREDIENT

TECHNICAL FIELD

The present invention relates to a beta-alanine derivative, pharmaceutically acceptable salts thereof, and a pharmaceutical composition including the same as an active ingredient.

BACKGROUND ART

Metabolic syndrome widely occurring around the world includes diabetes, hypertension, lipid dysbolism, insulin resistance, and the like, wherein these disorders are common disorders which mutually increase occurrence risk, and which relate to metabolic multi-changes in vivo such as aging, stress and immune function deterioration, and the like. In addition, obesity induces chronic disorders such as fatty liver, hypertension, diabetes, cardiovascular disorder, and the like, as well as a problem in view of appearance.

As anti-obesity agents sold in domestic and foreign markets, there is Xenical having orlistat approved by the FDA in the United States as a main ingredient. The Xenical inhibiting lipase function causes gastrointestinal side effects such as steatorrhea, gas generation, and deterioration in fat-soluble vitamin absorption, and the like. In addition thereto, the number of products prohibited for sale due to serious side effects among developed anti-obesity agents is significant. For example, it has been reported that aminophylline has a wide range of side effects through the nervous system, the circulatory system and the digestive system despite having an excellent body lipolysis effect. In addition, fenfluramine, dexfenfluramine, topiramate, ephedrine, and the like, are judged as an inappropriate anti-obesity agent and thus, prohibited for sale. As described above, since the existing pharmaceutical products have limitation and side effects in overcoming a wide range of chronic disorders, development of a new therapeutic agent for metabolic disorders having both of stability and efficacy has been continuously demanded.

A number of research papers and patents are cited throughout the present specification and the references are marked. The disclosure of the cited papers and patents are incorporated by reference in their entirety to more clearly describe the level of the technical field to which the present invention pertains and the content of the present invention.

DISCLOSURE

Technical Problem

The present inventors made an effort to develop a composition for effectively preventing or treating various disorders of lipid metabolism by discovering a compound having an inhibition activity against diacylglycerol acyltransferase 1 (DGAT1). As a result, the present inventors found that a beta-alanine derivative represented by the following Chemical Formula 1, which is unknown so far, significantly inhibits activity of the DGAT1, thereby completing the present invention.

Therefore, an object of the present invention is to provide a novel beta-alanine derivative or pharmaceutically acceptable salts thereof.

Another object of the present invention is to provide a pharmaceutical composition for preventing or treating obesity, diabetes, dyslipidemia, fatty liver, insulin resistance syndrome, or hepatitis, containing the beta-alanine derivative, the pharmaceutically acceptable salts thereof or a solvate thereof of the present invention, as an active ingredient.

The other objects and advantages of the present invention are more clearly described by the following detailed description, claims, and drawings, which are provided by way of example, and thus, the present invention is not limited thereto.

Technical Solution

In one general aspect, the present invention provides a beta-alanine derivative represented by the following Chemical Formula 1, or pharmaceutically acceptable salts thereof.

The beta-alanine derivative represented by the following Chemical Formula 1 or pharmaceutically acceptable salts thereof:

[Chemical Formula 1]

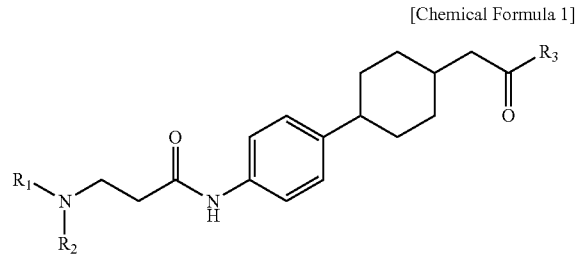

in Chemical Formula 1, $R_1$ and $R_2$ are each independently hydrogen, a $C_1$-$C_{10}$ alkyl group, a $C_3$-$C_7$ cycloalkyl group or

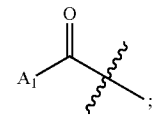

$A_1$ is a substituted or unsubstituted $C_1$-$C_7$ alkyl group, a substituted or unsubstituted $C_3$-$C_7$ cycloalkyl group, a substituted or unsubstituted $C_1$-$C_7$ alkoxy group, a substituted or unsubstituted $C_5$-$C_{20}$ aryl $C_1$-$C_7$ alkyl, a substituted or unsubstituted $C_5$-$C_{20}$ aryl group or a $C_3$-$C_{20}$ heteroaryl group containing 1 to 3 heteroatoms each independently selected from oxygen, nitrogen and sulfur;

$R_3$ is $OR_{30}$, or a substituted or unsubstituted amine group; and $R_{30}$ is hydrogen or $C_1$-$C_5$ alkyl.

In another general aspect, the present invention provides a pharmaceutical composition for preventing or treating a diacylglycerol acyltransferase 1 (DGAT1) activity inhibition-related disorder, containing the beta-alanine derivative represented by Chemical Formula 1 above, the pharmaceutically acceptable salts thereof or a solvate thereof, as an active ingredient.

Advantageous Effects

The novel beta-alanine derivative and pharmaceutically acceptable salts thereof according to the present invention may effectively inhibit the activity of DGAT1, which is an enzyme serving as a catalyst in the final step of the synthesis of neutral lipids, to thereby be effectively used as a pharmaceutical composition for preventing or treating various lipid metabolism-related disorders selected from the group consisting of obesity, dyslipidemia, fatty liver, insulin resistance syndrome, and hepatitis.

BEST MODE

Hereinafter, the present invention will be described in detail. Here, unless technical and scientific terms used herein are defined otherwise, they have meanings understood by those skilled in the art to which the present invention pertains. Known functions and components which obscure the description and the accompanying drawings of the present invention with unnecessary detail will be omitted.

The term "alkyl" used herein means a saturated straight chain or branched hydrocarbon group, for example, methyl, ethyl, propyl, isobutyl, pentyl, hexyl, or the like. $C_1$-$C_5$ alkyl means an alkyl group having an alkyl unit of 1 to 5 carbon atoms, and when $C_1$-$C_5$ alkyl is substituted, the number of carbons in the substituent is not included.

The term "halogen" used herein means a halogen element, for example, fluoro, chloro, bromo and iodo.

The term "aryl" used herein means a substituted or unsubstituted monocyclic or polycyclic carbon ring, which is entirely or partially unsaturated and has aromaticity.

The term "heteroaryl" used herein means a heterocyclic aromatic group including oxygen, sulfur or nitrogen in a ring as a heteroatom. The number of heteroatoms is 1 to 4, preferably, 1 to 2. Aryl in the heteroaryl is preferably monoaryl or biaryl.

The term "dyslipidemia" used herein has a concept including hyperlipidemia and means abnormal lipid condition caused by problems such as lipoprotein dysbolism, and the like, in addition to hypercholesterolemia, hypertriglyceridemia, low HDL-cholesterolemia caused by increase of lipid value in blood.

The term "fatty liver" used herein means a condition in which a large amount of fat accumulate in liver cells due to lipid metabolic disorder of liver, more specifically, means a condition in which a rate occupied by fat is more than 5% based on weight of the liver. Examples of disorders preventing or treating with the composition of the present invention include various fatty liver complications such as angina pectoris, myocardial infarction, stroke, arteriosclerosis, fatty liver, pancreatitis, and the like.

The term "insulin resistance" used herein means a condition in which cell is not allowed to effectively burn glucose due to decreased function of insulin which decreases blood glucose. In the case in which insulin resistance is high, excessive insulin is produced in human body, causing hypertension, dyslipidemia, heart disease, diabetes, and the like. In particular, in type 2 diabetes, the increase of insulin is not perceived in muscle and fat tissue, such that the function of the insulin is not generated.

The term "insulin resistance syndrome" used herein has a generic concept including disorders induced by the above-described insulin resistance, and means disorders characterized by increase in resistance of cell on insulin function, hyperinsulinemia, very low density lipoprotein (VLDL) and neutral fat, decrease in high density lipoprotein (HDL), and hypertension, and the like, which is recognized as a risk factor of cardiovascular disorders and type 2 diabetes (Reaven G M, *Diabetes*, 37: 1595-607, (1988)). In addition, it is known that insulin resistance increases oxidative stress and changes the signal transduction system in cells together with other risk factors such as hypertension, diabetes, smoking, and the like, thus inducing inflammatory responses and leading to atherosclerosis (Freeman B. A., et al., *Lab Invest.* 47: 412-26, (1982)), Kawamura M. et al., *J Clin. Invest.* 94: 771-8, (1994)).

The term "hepatitis" used herein means a disorder in which liver cells or liver tissues are damaged by inflammation due to the presence of inflammatory cells causing inflammation. More preferably, the hepatitis prevented or treated with the composition of the present invention is hepatitis type C.

According to a preferred embodiment of the present invention, the dyslipidemia treated with the composition of the present invention is hyperlipidemia.

The term "hyperlipidemia" used herein means a disorder in which metabolism of fats such as neutral fat, cholesterol, and the like, is not normally performed and induced an excessive amount of fat in blood, more specifically, hyperlipidemia includes hypercholesterolemia or hypertriglyceridemia which highly occurs in a state in which lipid components such as neutral fat, LDL cholesterol, phospholipid, free fatty acid, and the like, are increased in blood.

The present inventors made an effort to develop a composition for effectively preventing or treating various lipid metabolic disorders induced by abnormal activity of diacylglycerol acyltransferase 1 (DGAT1) by discovering a compound having inhibition activity against the DGAT1. As a result, the present inventors found that the beta-alanine derivative represented by Chemical Formula 1 above, which is unknown so far, significantly inhibits activity of the DGAT1.

The diacylglycerol acyltransferase 1 (DGAT1) which is an enzyme serving as a catalyst in the final step of the synthesis of neutral lipids is permanently stationed in the endoplasmic reticulum (ER) and acylates fat molecules to be stored as a neutral fat form. In the case of suppressing the DGAT1 to inhibit biosynthesis of the neutral fat, accumulation of the fat in adipose tissue is inhibited, a size of fat cell is decreased, energy consumption is increased by the increase in momentum and increase in uncoupling protein expression, thereby inhibiting the increase in weight induced by a high fat diet. In addition, it is known that suppression of DGAT1 increases insulin resistance by inhibiting the accumulation of the fat in non-adipose tissues such as skeletal muscle, liver, pancreas, and the like.

In addition, it is reported that the DGAT1 is involved in storing fat in the liver, and in the case in which the activity of the DGAT1 is inhibited, hepatitis C virus (HCV) is not capable of producing infectious virus particles (Eva Herker et al., Efficient Hepatitis C Virus Particle Formation Requires Diacylglycerol Acyltransferase-1, *Nature Medicine* 16:1295-1298 (2010)). Therefore, the composition of the present invention effectively inhibiting the activity of the DGAT1 may be utilized as a pharmaceutical composition for preventing or treating diacylglycerol acyltransferase 1 (DGAT1) activity inhibition-related disorders, and particularly, may be an agent for effectively preventing and treating not only various lipid metabolism disorders such as obesity, diabetes, dyslipidemia, fatty liver, insulin resistance syndrome, and the like, but also hepatitis.

The compound of the present invention is a beta-alanine derivative represented by the following Chemical Formula 1 or pharmaceutically acceptable salts thereof:

[Chemical Formula 1]

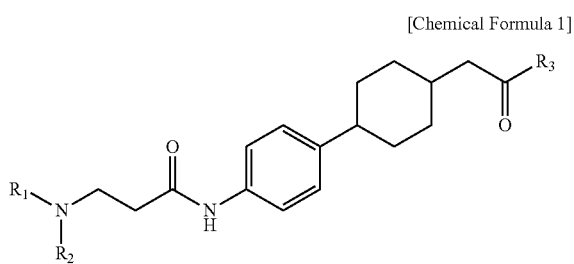

in Chemical Formula 1, $R_1$ and $R_2$ are each independently hydrogen, a $C_1$-$C_{10}$ alkyl group, a $C_3$-$C_7$ cycloalkyl group or

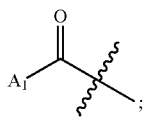

$A_1$ is a substituted or unsubstituted $C_1$-$C_7$ alkyl group, a substituted or unsubstituted $C_3$-$C_7$ cycloalkyl group, a substituted or unsubstituted $C_1$-$C_7$ alkoxy group, a substituted or unsubstituted $C_5$-$C_{20}$ aryl $C_1$-$C_7$ alkyl, a substituted or unsubstituted $C_5$-$C_{20}$ aryl group or a $C_3$-$C_{20}$ heteroaryl group containing 1 to 3 heteroatoms each independently selected from oxygen, nitrogen and sulfur;

$R_3$ is $OR_{30}$, or a substituted or unsubstituted amine group; and $R_{30}$ is hydrogen or $C_1$-$C_5$ alkyl.

Substitutable $C_1$-$C_7$ alkyl group, $C_3$-$C_7$ cycloalkyl group, $C_1$-$C_7$ alkoxy group, $C_5$-$C_{20}$ aryl $C_1$-$C_7$ alkyl, $C_5$-$C_{20}$ aryl group or $C_3$-$C_{20}$ heteroaryl group containing 1 to 3 heteroatoms each independently selected from oxygen, nitrogen and sulfur in $A_1$ may be substituted with one or more substituents each independently selected from halogen, a substituted or unsubstituted $C_1$-$C_7$ alkyl group, a carboxyl group, a substituted or unsubstituted $C_1$-$C_7$ alkylcarbonyl group, a substituted or unsubstituted $C_1$-$C_7$ alkoxy group, a substituted or unsubstituted $C_3$-$C_7$ cycloalkyl group, a $C_1$-$C_7$ alkoxycarbonyl group, a carboxy $C_1$-$C_7$ alkyl group, a substituted or unsubstituted $C_5$-$C_{20}$ aryl group, a substituted or unsubstituted $C_3$-$C_{20}$ heteroaryl group containing 1 to 2 or more heteroatoms selected from oxygen, nitrogen and sulfur, a nitro group, and an amino group, and additionally, may be further substituted with one or more selected from the group consisting of halogen, a $C_1$-$C_7$ alkyl group, a $C_3$-$C_7$ cycloalkyl group, and a $C_1$-$C_7$ alkoxy group.

More specifically, in Chemical Formula 1 above, $R_1$ and $R_2$ are each independently hydrogen or

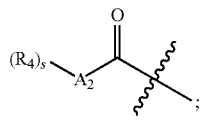

$A_2$ is a $C_1$-$C_7$ alkylene group, a $C_3$-$C_7$ cycloalkylene group, a $C_5$-$C_{20}$ arylene group or a $C_3$-$C_{20}$ heteroarylene group containing 1 to 3 heteroatoms each independently selected from oxygen, nitrogen and sulfur;

$R_4$ is hydrogen, each independently halogen, a substituted or unsubstituted $C_1$-$C_7$ alkyl group, a substituted or unsubstituted $C_3$-$C_7$ cycloalkyl group, a substituted or unsubstituted $C_1$-$C_7$ alkoxy group, a substituted or unsubstituted amino group, a substituted or unsubstituted $C_5$-$C_{20}$ aryl group or a substituted or unsubstituted $C_3$-$C_{20}$ heteroaryl group containing 1 to 2 or more heteroatoms selected from oxygen, nitrogen and sulfur; and s is an integer of 0 to 3.

More preferably, there is provided the beta-alanine derivative wherein $A_2$ is phenylene, naphthylene, benzylene, pyridylene, pyrimidinylene, triazinylene, oxazolene, pyrazolene, oxadiazolene, thiazolene, or indolene, or pharmaceutically acceptable salts thereof.

There is provided the beta-alanine derivative wherein $R_4$ is further substituted with at least one substituent independently selected from halogen, a substituted or unsubstituted $C_1$-$C_7$ alkyl group, a carboxyl group, a substituted or unsubstituted $C_1$-$C_7$ alkylcarbonyl group, a substituted or unsubstituted $C_1$-$C_7$ alkoxy group, a substituted or unsubstituted $C_3$-$C_7$ cycloalkyl group, a $C_1$-$C_7$ alkoxycarbonyl group, a carboxy $C_1$-$C_7$ alkyl group, a substituted or unsubstituted $C_5$-$C_{20}$ aryl group, a substituted or unsubstituted $C_3$-$C_{20}$ heteroaryl group containing 1 to 2 or more heteroatoms selected from oxygen, nitrogen and sulfur, a nitro group, and an amino group, or pharmaceutically acceptable salts thereof.

There is provided the beta-alanine derivative wherein the $R_4$ is further substituted with at least one substituent independently selected from halogen; a $C_1$-$C_7$ alkyl group which is unsubstituted or substituted with halogen, a $C_1$-$C_7$ alkyl group, a $C_3$-$C_7$ cycloalkyl group or a $C_1$-$C_7$ alkoxy group; a carboxyl group; a $C_1$-$C_7$ alkylcarbonyl group which is unsubstituted or substituted with halogen, a $C_1$-$C_7$ alkyl group, a $C_3$-$C_7$ cycloalkyl group or a $C_1$-$C_7$ alkoxy group; a $C_1$-$C_7$ alkoxy group which is unsubstituted or substituted with halogen, a $C_1$-$C_7$ alkyl group, a $C_3$-$C_7$ cycloalkyl group or a $C_1$-$C_7$ alkoxy group; a $C_3$-$C_7$ cycloalkyl group which is unsubstituted or substituted with halogen, a $C_1$-$C_7$ alkyl group, a $C_3$-$C_7$ cycloalkyl group or a $C_1$-$C_7$ alkoxy group; a $C_1$-$C_7$ alkoxycarbonyl group which is unsubstituted or substituted with halogen, a $C_1$-$C_7$ alkyl group, a $C_3$-$C_7$ cycloalkyl group or a $C_1$-$C_7$ alkoxy group; a carboxy $C_1$-$C_7$ alkyl group which is unsubstituted or substituted with halogen, a $C_1$-$C_7$ alkyl group, a $C_3$-$C_7$ cycloalkyl group or a $C_1$-$C_7$ alkoxy group; a $C_5$-$C_{20}$ aryl group which is unsubstituted or substituted with halogen, a $C_1$-$C_7$ alkyl group, a $C_3$-$C_7$ cycloalkyl group or a $C_1$-$C_7$ alkoxy group; a $C_3$-$C_{20}$ heteroaryl group containing 1 to 2 or more heteroatoms selected from oxygen, nitrogen and sulfur which is unsubstituted or substituted with halogen, a $C_1$-$C_7$ alkyl group, a $C_3$-$C_7$ cycloalkyl group or a $C_1$-$C_7$ alkoxy group; a nitro group which is unsubstituted or substituted with halogen, a $C_1$-$C_7$ alkyl group, a $C_3$-$C_7$ cycloalkyl group or a $C_1$-$C_7$ alkoxy group; and an amino group which is unsubstituted or substituted with halogen, a $C_1$-$C_7$ alkyl group, a $C_3$-$C_7$ cycloalkyl group or a $C_1$-$C_7$ alkoxy group, or pharmaceutically acceptable salts thereof.

According to a preferred embodiment of the present invention, the beta-alanine derivative represented by Chemical Formula 1 of the present invention or pharmaceutically acceptable salts thereof may be selected from the group consisting of the following compounds 1 to 105:

1) trans-(4-{4-[3-(3,4-diethoxybenzoylamino)propionylamino]phenyl}cyclohexyl)acetic acid methyl ester;
2) trans-(4-{4-[3-(3,4-diethoxybenzoylamino)propionylamino]phenyl}cyclohexyl)acetic acid;
3) trans-(4-{4-[3-(4-ethoxybenzoylamino)propionylamino]phenyl}cyclohexyl)acetic acid methyl ester;
4) trans-(4-{4-[3-(4-ethoxybenzoylamino)propionylamino]phenyl}cyclohexyl)acetic acid;

5) trans-[4-(4-{3-[(2-phenyl-5-trifluoromethyloxazole-4-carbonyl)amino]propionylamino}phenyl)cyclohexyl]acetic acid methyl ester;
6) trans-[4-(4-{3-[(2-Phenyl-5-trifluoromethyloxazole-4-carbonyl)amino]propionylamino}phenyl)cyclohexyl]acetic acid;
7) trans-[4-(4-{3-[(1-phenyl-3-trifluoromethyl-1H-pyrazole-4-carbonyl)amino]propionylamino}phenyl)cyclohexyl]acetic acid;
8) trans-2-(4-(4-(3-(2-(2,3-dichlorophenyl)-5-(trifluoromethyl)oxazole-4-carboxamido)propanamido)phenyl)cyclohexyl)acetic acid;
9) trans-2-(4-(4-(3-(2-(2,5-dichlorophenyl)-5-(trifluoromethyl)oxazole-4-carboxamido)propanamido)phenyl)cyclohexyl)acetic acid;
10) trans-{4-[4-(3-{[2-(2-chlorophenyl)-5-trifluoromethyloxazole-4-carbonyl]amino}propionylamino)phenyl]cyclohexyl}acetic acid methyl ester;
11) trans-{4-[4-(3-{[2-(2-chlorophenyl)-5-trifluoromethyloxazole-4-carbonyl]amino}propionylamino)phenyl]cyclohexyl}acetic acid;
12) trans-{4-[4-(3-{[2-(4-chlorophenyl)-5-trifluoromethyloxazole-4-carbonyl]amino}propionylamino)phenyl]cyclohexyl}acetic acid methyl ester;
13) trans-{4-[4-(3-{[2-(4-chlorophenyl)-5-trifluoromethyloxazole-4-carbonyl]amino}propionylamino)phenyl]cyclohexyl}acetic acid;
14) trans-[4-(4-{3-[(2-phenyl-4-trifluoromethyloxazole-5-carbonyl)amino]propionylamino}phenyl)cyclohexyl]acetic acid methyl ester;
15) trans-[4-(4-{3-[(2-phenyl-4-trifluoromethyloxazole-5-carbonyl)amino]propionylamino}phenyl)cyclohexyl]acetic acid;
16) trans-[4-(4-{3-[(5-phenyl-[1,2,4]oxadiazole-3-carbonyl)amino]propionylamino}phenyl)cyclohexyl]acetic acid methyl ester;
17) trans-[4-(4-{3-[(5-phenyl-[1,2,4]oxadiazole-3-carbonyl)amino]propionylamino}phenyl)cyclohexyl]acetic acid;
18) trans-[4-(4-{3-[(2-p-tolyl-5-trifluoromethyloxazole-4-carbonyl)amino]propionylamino}phenyl)cyclohexyl]acetic acid methyl ester;
19) trans-[4-(4-{3-[(2-p-tolyl-5-trifluoromethyloxazole-4-carbonyl)amino]propionylamino}phenyl)cyclohexyl]acetic acid;
20) trans-[4-(4-{3-[(2-o-tolyl-5-trifluoromethyloxazole-4-carbonyl)amino]propionylamino}phenyl)cyclohexyl]acetic acid methyl ester;
21) trans-[4-(4-{3-[(2-o-tolyl-5-trifluoromethyloxazole-4-carbonyl)amino]propionylamino}phenyl)cyclohexyl]acetic acid;
22) sodium; trans-[4-(4-{3-[(2-phenyl-5-trifluoromethyloxazole-4-carbonyl)amino]propionylamino}phenyl)cyclohexyl]acetate;
23) trans-{4-[4-(3-tert-Butoxycarbonylaminopropionylamino)phenyl]cyclohexyl}acetic acid methyl ester;
24) trans-{4-[4-(3-tert-Butoxycarbonylaminopropionylamino)phenyl]cyclohexyl}acetic acid;
25) trans-{4-[4-(3-amino-propionylamino)phenyl]cyclohexyl}acetic acid methyl ester hydrochloride;
26) trans-{4-[4-(3-{[2-(4-bromo-phenyl)-5-trifluoromethyloxazole-4-carbonyl]amino}propionylamino)phenyl]cyclohexyl}acetic acid methyl ester;
27) trans-{4-[4-(3-{[2-(4-bromophenyl)-5-trifluoromethyloxazole-4-carbonyl]amino}propionylamino)phenyl]cyclohexyl}acetic acid;
28) trans-[4-(4-{3-[(2-methyl-5-trifluoromethyloxazole-4-carbonyl)amino]propionylamino}phenyl)cyclohexyl]acetic acid methyl ester;
29) trans-[4-(4-{3-[(2-methyl-5-trifluoromethyloxazole-4-carbonyl)amino]propionylamino}phenyl)cyclohexyl]acetic acid;
30) trans-[4-(4-{3-[(5-methyl-2-phenyloxazole-4-carbonyl)amino]propionylamino}phenyl)cyclohexyl]acetic acid methyl ester;
31) trans-[4-(4-{3-[(5-methyl-2-phenyloxazole-4-carbonyl)amino]propionylamino}phenyl)cyclohexyl]acetic acid;
32) trans-[4-(4-{3-[(4-methyl-2-phenylthiazole-5-carbonyl)amino]propionylamino}phenyl)cyclohexyl]acetic acid methyl ester;
33) trans-[4-(4-{3-[(4-methyl-2-phenylthiazole-5-carbonyl)amino]propionylamino}phenyl)cyclohexyl]acetic acid;
34) trans-{4-[4-(3-{[2-(4-chlorophenyl)-4-methylthiazole-5-carbonyl]amino}propionylamino)phenyl]cyclohexyl}acetic acid methyl ester;
35) trans-{4-[4-(3-{[2-(4-chlorophenyl)-4-methylthiazole-5-carbonyl]amino}propionylamino)phenyl]cyclohexyl}acetic acid;
36) trans-[4-(4-{3-[(2-phenyl-4-trifluoromethylthiazole-5-carbonyl)amino]propionylamino}phenyl)cyclohexyl]acetic acid methyl ester;
37) trans-[4-(4-{3-[(2-phenyl-4-trifluoromethylthiazole-5-carbonyl)amino]propionylamino}phenyl)cyclohexyl]acetic acid;
38) trans[4-(4-{3-[(2-methoxy-4-trifluoromethylthiazole-5-carbonyl)amino]propionylamino}phenyl)cyclohexyl]acetic acid methyl ester;
39) trans[4-(4-{3-[(2-methoxy-4-trifluoromethylthiazole-5-carbonyl)amino]propionylamino}phenyl)cyclohexyl]acetic acid;
40) trans-{4-[4-(3-{[4-trifluoromethyl-2-(6-trifluoromethylpyridin-3-ylamino)thiazole-5-carbonyl]amino}propionylamino)phenyl]cyclohexyl}acetic acid;
41) trans-2-phenyl-5-trifluoromethyloxazole-4-carboxylic acid{2-[4-(4-carbamoylmethylcyclohexyl)phenylcarbamoyl]ethyl}amide;
42) trans-{4-[4-(3-{[5-(2-trifluoromethylphenyl)isoxazole-3-carbonyl]amino}propionylamino)phenyl]cyclohexyl}acetic acid methyl ester;
43) trans-{4-[4-(3-{[5-(2-trifluoromethylphenyl)isoxazole-3-carbonyl]amino}propionylamino)phenyl]cyclohexyl}acetic acid;
44) trans-[4-(4-{3-[(1-o-tolyl-3-trifluoromethyl-1H-pyrazole-4-carbonyl)amino]propionylamino}phenyl)cyclohexyl]acetic acid methyl ester;
45) trans-[4-(4-{3-[(1-o-tolyl-3-trifluoromethyl-1H-pyrazol-4-ylmethyl)amino]propionylamino}phenyl)cyclohexyl]acetic acid;
46) trans-[4-(4-{3-[(1-p-tolyl-3-trifluoromethyl-1H-pyrazole-4-carbonyl)amino]propionylamino}phenyl)cyclohexyl]acetic acid methyl ester;
47) trans-[4-(4-{3-[(1-p-tolyl-3-trifluoromethyl-1H-pyrazole-4-carbonyl)amino]propionylamino}phenyl)cyclohexyl]acetic acid;
48) trans-{4-[4-(3-{[1-(4-chlorophenyl)-3-trifluoromethyl-1H-pyrazole-4-carbonyl]amino}propionylamino)phenyl]cyclohexyl}acetic acid methyl ester;
49) trans-{4-[4-(3-{[1-(4-chlorophenyl)-3-trifluoromethyl-1H-pyrazole-4-carbonyl]amino}propionylamino)phenyl]cyclohexyl}acetic acid;
50) trans-{4-[4-(3-{[1-(2-chlorophenyl)-3-trifluoromethyl-1H-pyrazole-4-carbonyl]amino}propionylamino)phenyl]cyclohexyl}acetic acid methyl ester;

51) trans-{4-[4-(3-{[1-(2-Chlorophenyl)-3-trifluoromethyl-1H-pyrazole-4-carbonyl]amino}propionylamino)phenyl]cyclohexyl}acetic acid;
52) trans-{4-[4-(3-{[1-(4-methoxyphenyl)-3-trifluoromethyl-1H-pyrazole-4-carbonyl]amino}propionylamino)phenyl]cyclohexyl}acetic acid methyl ester;
53) trans-{4-[4-(3-{[1-(4-methoxyphenyl)-3-trifluoromethyl-1H-pyrazole-4-carbonyl]amino}propionylamino)phenyl]cyclohexyl}acetic acid;
54) trans-[4-(4-{3-[(5-chloro-1H-indole-2-carbonyl)amino]propionylamino}phenyl)cyclohexyl]acetic acid methyl ester;
55) trans-[4-(4-{3-[(5-chloro-1H-indole-2-carbonyl)amino]propionylamino}phenyl)cyclohexyl]acetic acid;
56) trans-{4-[4-(3-{[2-(4-fluorophenyl)-5-trifluoromethyloxazole-4-carbonyl]amino}propionylamino)phenyl]cyclohexyl}acetic acid;
57) trans-[4-(4-{3-[2-(4-trifluoromethoxyphenyl)acetylamino]propionylamino}phenyl)cyclohexyl]acetic acid;
58) trans-(4-{4-[3-(4-cyclopropylmethoxybenzoylamino)propionylamino]phenyl}cyclohexyl)acetic acid;
59) trans-{4-[4-(3-{[2-(2-Fluorophenyl)-5-trifluoromethyloxazole-4-carbonyl]amino}propionylamino)phenyl]cyclohexyl}acetic acid methyl ester;
60) trans-{4-[4-(3-{[2-(2-Fluorophenyl)-5-trifluoromethyloxazole-4-carbonyl]amino}propionylamino)phenyl]cyclohexyl}acetic acid;
61) trans-(4-{4-[3-(4-chlorobenzoylamino)propionylamino]phenyl}cyclohexyl)acetic acid methyl ester;
62) trans(4-{4-[3-(4-chlorobenzoylamino)propionylamino]phenyl}cyclohexyl)acetic acid;
63) trans-{4-[4-(3-{[2-(2,4-dichlorophenyl)-5-trifluoromethyloxazole-4-carbonyl]amino}propionylamino)phenyl]cyclohexyl}acetic acid methyl ester;
64) trans-{4-[4-(3-{[2-(2,4-dichlorophenyl)-5-trifluoromethyloxazole-4-carbonyl]amino}propionylamino)phenyl]cyclohexyl}acetic acid;
65) trans-{4-[4-(3-{[2-(2-Bromophenyl)-5-trifluoromethyloxazole-4-carbonyl]amino}propionylamino)phenyl]cyclohexyl}acetic acid;
66) trans-{4-[4-(3-{[5-trifluoromethyl-2-(2-trifluoromethylphenyl)oxazole-4-carbonyl]amino}propionylamino)phenyl]cyclohexyl}acetic acid;
67) trans-{4-[4-(3-{[2-(3-chlorophenyl)-5-trifluoromethyloxazole-4-carbonyl]amino}propionylamino)phenyl]cyclohexyl}acetic acid;
68) trans-{4-[4-(3-{[2-(2,6-dichlorophenyl)-5-trifluoromethyloxazole-4-carbonyl]amino}propionylamino)phenyl]cyclohexyl}acetic acid;
69) sodium; trans-{4-[4-(3-{[2-(2,6-dichlorophenyl)-5-trifluoromethyloxazole-4-carbonyl]amino}propionylamino)phenyl]cyclohexyl}acetate;
70) trans-{4-[4-(3-{[2-(2-chlorophenyl)-5-methyloxazole-4-carbonyl]amino}propionylamino)phenyl]cyclohexyl}acetic acid;
71) trans-{4-[4-(3-{[2-(2-methoxyphenyl)-5-trifluoromethyloxazole-4-carbonyl]amino}propionylamino)phenyl]cyclohexyl}acetic acid;
72) trans-{4-[4-(3-{[2-(2,6-difluorophenyl)-5-trifluoromethyloxazole-4-carbonyl]amino}propionylamino)phenyl]cyclohexyl}acetic acid;
73) trans-{4-[4-(3-{[2-(2-chloro-6-fluorophenyl)-5-trifluoromethyloxazole-4-carbonyl]amino}propionylamino)phenyl]cyclohexyl}acetic acid;
74) trans-[4-(4-{3-[(2'-methylbiphenyl-4-carbonyl)amino]propionylamino}phenyl)cyclohexyl]acetic acid;
75) trans-[4-(4-(3-(2',6'-dimethyl biphenyl-4-carbonylamino)propionylamino)phenyl)cyclohexyl]acetic acid;
76) trans-[4-(4-{3-[4-(4-carboxymethylcyclohexyl)benzoylamino]propionylamino}phenyl)cyclohexyl]acetic acid;
77) trans-{4-[4-(3-{[2-(2-nitrophenyl)-5-trifluoromethyloxazole-4-carbonyl]amino}propionylamino)phenyl]cyclohexyl}acetic acid;
78) trans-[4-(4-{3-[(biphenyl-4-carbonyl)amino]propionylamino}phenyl)cyclohexyl]acetic acid;
79) sodium; trans-{4-[4-(3-{[2-(2-chlorophenyl)-5-trifluoromethyloxazole-4-carbonyl]amino}propionylamino)phenyl]cyclohexyl}acetate;
80) trans-[4-(4-{3-[(naphthalene-2-carbonyl)amino]propionylamino}phenyl)cyclohexyl]acetic acid;
81) trans-4-(4-{2-[4-(4-methoxycarbonylmethylcyclohexyl)phenylcarbamoyl]ethylcarbamoyl}phenoxy)cyclohexanecarboxylic acid ethyl ester;
82) cis, trans-4-(4-{2-[4-(4-carboxymethylcyclohexyl)phenylcarbamoyl]ethylcarbamoyl}phenoxy)cyclohexanecarboxylic acid;
83) trans-[4-(4-{3-[(4-fluoronaphthalene-1-carbonyl)amino]propionylamino}phenyl)cyclohexyl]acetic acid;
84) trans-[4-(4-(3-(2',6'-dichlorobiphenyl-4-carbonylamino)propionylamino)phenyl)cyclohexyl]acetic acid;
85) trans-{4-[4-(3-{[3-(2-chloro-6-fluorophenyl)-5-methylisoxazole-4-carbonyl]amino}propionylamino)phenyl]cyclohexyl}acetic acid;
86) trans-[4-(4-{3-[(2'-chlorobiphenyl-4-carbonyl)amino]propionylamino}phenyl)cyclohexyl]acetic acid;
87) trans-[4-(4-{3-[(5-chloro-2-phenyloxazole-4-carbonyl)amino]propionylamino}phenyl)cyclohexyl]acetic acid;
88) trans-[4-(4-(3-(2',6'-difluorobiphenyl-4-carbonylamino)propionylamino)phenyl)cyclohexyl]acetic acid;
89) trans-[4-(4-(3-(2',4'-difluorobiphenyl-4-carbonylamino)propionylamino)phenyl)cyclohexyl]acetic acid;
90) trans-[4-(4-(3-(2'-ethylbiphenyl-4-carbonylamino)propionylamino)phenyl)cyclohexyl]acetic acid;
91) trans-[4-(4-{3-[(2-phenyloxazole-4-carbonyl)amino]propionylamino}phenyl)cyclohexyl]acetic acid;
92) trans-[4-(4-{3-[(5-phenylpyridine-3-carbonyl)amino]propionylamino}phenyl)cyclohexyl]acetic acid;
93) trans-[4-(4-{3-[(4'-ethylbiphenyl-4-carbonyl)amino]propionylamino}phenyl)cyclohexyl]acetic acid;
94) trans-[4-(4-{3-[(2-chlorobiphenyl-4-carbonyl)amino]propionylamino}phenyl)cyclohexyl]acetic acid;
95) trans-{4-[4-(3-{[5-chloro-2-(2-chlorophenyl)oxazole-4-carbonyl]amino}propionylamino)phenyl]cyclohexyl}acetic acid;
96) trans-(4-{4-[3-(4-pyrimidin-5-yl-benzoylamino)propionylamino]phenyl}cyclohexyl)acetic acid;
97) trans-(4-{4-[3-(4-pyrimidin-2-yl-benzoylamino)propionylamino]phenyl}cyclohexyl)acetic acid;
98) trans-{4-[4-(3-{[5-chloro-2-(2,4,5-trifluorophenyl)-oxazole-4-carbonyl]amino}propionylamino)phenyl]cyclohexyl}acetic acid;
99) trans-[4-(4-{3-[(2'-trifluoromethylbiphenyl-4-carbonyl)amino]propionylamino}phenyl)cyclohexyl]acetic acid;
100) trans-[4-(4-{3-[(6-phenylpyridine-3-carbonyl)amino]propionylamino}phenyl)cyclohexyl]acetic acid;
101) trans-{4-[4-(3-{[6-(2-trifluoromethylphenyl)pyridine-3-carbonyl]amino}propionylamino)phenyl]cyclohexyl}acetic acid;
102) trans-{4-[4-(3-{[2-(2,4,5-trifluorophenyl)oxazole-4-carbonyl]amino}propionylamino)phenyl]cyclohexyl}acetic acid;

103) trans-{4-[4-(3-{[2-(2-iodophenyl)-5-trifluoromethyloxazole-4-carbonyl]amino}propionylamino)phenyl]cyclohexyl}acetic acid;

104) trans-{4-[4-(3-{[2-(2-chlorophenyl)oxazole-4-carbonyl]amino}propionylamino)phenyl]cyclohexyl}acetic acid; and 105) (trans-(4-(4-(3-(2-(2,6-dichloro-4-fluorophenyl)-5-(trifluoromethyl)oxazole-4-carboxamido)propanamido)phenyl)cyclohexyl)acetic acid.

According to more preferred embodiment of the present invention, the beta-alanine derivative of the present invention or the pharmaceutically acceptable salts thereof are selected from the group consisting of the following compounds 4, 6, 11, 41, 60, 64, 65, 66, 68, 69, 79, 93, 94, 95 and 105.

4) trans-(4-{4-[3-(4-ethoxybenzoylamino)propionylamino]phenyl}cyclohexyl)acetic acid;

6) trans-[4-(4-{3-[(2-phenyl-5-trifluoromethyloxazole-4-carbonyl)amino]propionylamino}phenyl)cyclohexyl]acetic acid;

11) trans-{4-[4-(3-{[2-(2-chlorophenyl)-5-trifluoromethyloxazole-4-carbonyl]amino}propionylamino)phenyl]-cyclohexyl}-acetic acid;

41) trans-2-phenyl-5-trifluoromethyloxazole-4-carboxylic acid{2-[4-(4-carbamoylmethylcyclohexyl)phenylcarbamoyl]ethyl}amide;

60) trans-{4-[4-(3-{[2-(2-fluorophenyl)-5-trifluoromethyloxazole-4-carbonyl]amino}propionylamino)phenyl]cyclohexyl}acetic acid;

64) trans-{4-[4-(3-{[2-(2,4-dichlorophenyl)-5-trifluoromethyloxazole-4-carbonyl]amino}propionylamino)phenyl]cyclohexyl}acetic acid;

65) trans-{4-[4-(3-{[2-(2-bromophenyl)-5-trifluoromethyloxazole-4-carbonyl]amino}propionylamino)phenyl]cyclohexyl}acetic acid;

66) trans-{4-[4-(3-{[5-trifluoromethyl-2-(2-trifluoromethylphenyl)oxazole-4-carbonyl]amino}propionylamino)phenyl]cyclohexyl}acetic acid;

68) trans-{4-[4-(3-{[2-(2,6-dichlorophenyl)-5-trifluoromethyloxazole-4-carbonyl]amino}propionylamino)phenyl]cyclohexyl}acetic acid;

69) sodium; trans-{4-[4-(3-{[2-(2,6-dichlorophenyl)-5-trifluoromethyloxazole-4-carbonyl]amino}propionylamino)phenyl]cyclohexyl}acetate;

79) sodium; trans-{4-[4-(3-{[2-(2-chlorophenyl)-5-trifluoromethyloxazole-4-carbonyl]amino}propionylamino)phenyl]cyclohexyl}acetate;

93) trans-[4-(4-{3-[(4'-ethyl-biphenyl-4-carbonyl)amino]propionylamino}phenyl)cyclohexyl]acetic acid;

94) trans-[4-(4-{3-[(2-chlorobiphenyl-4-carbonyl)amino]propionylamino}phenyl)cyclohexyl]acetic acid;

95) trans-{4-[4-(3-{[5-chloro-2-(2-chlorophenyl)-oxazole-4-carbonyl]amino}propionylamino)phenyl]cyclohexyl}acetic acid; and 105) trans-(4-(4-(3-(2-(2,6-dichloro-4-fluorophenyl)-5-(trifluoromethyl)oxazole-4-carboxamido)propanamido)phenyl)cyclohexyl)acetic acid.

According to the present invention, the above-listed fifteen compounds have a significantly low inhibition concentration ($IC_{50}$) of 50 nM or less in inhibitory activity of DGAT1. Therefore, the compounds may be used as a significantly effective therapeutic composition of various lipid metabolic disorders and hepatitis.

According to another embodiment of the present invention, the present invention provides a pharmaceutical composition for preventing or treating activity inhibition-related disorders, containing the beta-alanine derivative of the present invention, the pharmaceutically acceptable salts thereof, or a solvate thereof, as an active ingredient, for example, a pharmaceutical composition for preventing or treating obesity, dyslipidemia, fatty liver, insulin resistance syndrome, or hepatitis.

According to a preferred embodiment of the present invention, the insulin resistance syndrome treated with the composition of the present invention is one or more disorders selected from the group consisting of obesity, hypertension, arteriosclerosis, hyperlipidemia, hyperinsulinemia, non-alcoholic fatty liver, and diabetes, caused by insulin resistance.

The term "diabetes" used herein means a chronic disease characterized by relative or absolute shortage of insulin causing glucose-intolerance. The diabetes prevented or treated with the composition of the present invention may be selected from the group consisting of Type I diabetes, Type II diabetes, idiopathic Type I diabetes (Ib type), adult latent autoimmune diabetes (LADA), early-onset type 2 diabetes (EOD), youth-onset atypical diabetes (YOAD), maturity onset diabetes of the young (MODY), malnutrition-related diabetes, hereditary diabetes and gestational diabetes. The diabetes includes Type I diabetes and Type II diabetes. The type 1 diabetes, also referred to as insulin dependent diabetes, is mainly caused by destruction of β-cell, and the type 2 diabetes, also referred to as insulin independent diabetes, is caused by insufficient insulin secretion or insulin resistance after eating.

The composition of the present invention may be provided as a pharmaceutical composition for preventing or treating lipid metabolic disorder such as obesity, dyslipidemia, fatty liver, insulin resistance syndrome, or hepatitis.

The composition of the present invention may further contain at least one pharmaceutical agent selected from the group consisting of anti-obesity agents or anti-diabetic agents. For example, the anti-obesity agent may be selected from the group consisting of dirlotapide, mitratapide, implitapide, R56918 (CAS No. 403987), CAS No. 913541-47-6, lorcaserin, cetilistat, $PYY_{3-36}$, naltrexone, oleoyl-estrone, obinepitide, pramlintide, tesofensine, leptin, liraglutide, bromocriptine, orlistat, exenatide, AOD-9604 (CAS No. 221231-10-3) and sibutramine.

The anti-diabetic agent may be selected from the group consisting of metformin, acetohexamide, chlorpropamide, diabinese, glibenclamide, glipizide, glyburide, glimepiride, gliclazide, glipentide, gliquidone, glisolamide, tolazamide, tolbutamide, tendamistat, trestatin, acarbose, adiposine, camiglibose, emiglitate, miglitol, voglibose, pradimicin-Q, salbostatin, balaglitazone, ciglitazone, darglitazone, englitazone, isaglitazone, pioglitazone, rosiglitazone, troglitazone, exendin-3, exendin-4, trodusquemine, reservatrol, hyrtiosal extract, sitagliptin, vildagliptin, alogliptin and saxagliptin, but the present invention is not limited thereto.

In the case in which the composition of the present invention is prepared as a pharmaceutical composition, the pharmaceutical composition of the present invention contains a pharmaceutically acceptable carrier. The pharmaceutically acceptable carrier contained in the pharmaceutical composition of the present invention, which is generally used in preparation, includes lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil, but the present invention is not limited thereto. The pharmaceutical composition of the present invention may further contain a lubricant, a wetting agent, a sweetening agent, a flavouring agent, an emulsifier, a suspension, a preservative, and the like, in addition to the above components. Appropriate pharmaceutically acceptable carriers and formulations are described in *Remington's Pharmaceutical Sciences* (19th ed., 1995) in detail.

The pharmaceutical composition of the present invention may be orally or parenterally administered, and the parenteral administration may include intravenous injection, subcutaneous injection, intramuscular injection, intraperitoneal injection, transdermal administration, and the like.

An appropriate dosage of the pharmaceutical composition of the present invention may be variously prescribed by factors such as formulation methods, administration types, age, body weight, sex, morbidity of patients, food, administration time, administration route, excretion rate and response sensitivity. A daily dosage of the pharmaceutical composition of the present invention is, for example, 0.001 to 100 mg/kg.

The pharmaceutical composition of the present invention may be formulated as general formulations using the pharmaceutically acceptable carriers and/or excipients according to methods easily practiced by a person skilled in the art to which the present invention pertains, to be prepared as a unit dosage form or to be prepared by introducing the composition into a multi-dosage container. The general formulation refers to oral (including tablets, capsules, powders), intrabuccal, sublingual, intrarectal, intravaginal, intranasal, topical or parenteral (including intravenous, cavernous, intramuscular, subcutaneous and intravascular) administration formulation. For example, the compound according to the present invention may be parenterally, intrabuccally or sublingually administered as a tablet form containing starch or lactose, or a capsule form alone or containing excipient, or an elixir or a suspension form containing chemicals to provide flavor or have color. Liquid formulations are prepared with pharmaceutically acceptable additives such as suspensions (for example, methyl cellulose, semisynthetic glyceride such as witepsol, mixture of apricot kernel oil and PEG-6 ester, glyceride mixtures such as PEG-8 and caprylic/capric glyceride mixture). In addition, in the case in which the compound is parenterally injected through intravenous, cavernous, intramuscular, subcutaneous, and intravascular, an aseptic aqueous solution form is the most preferred, wherein the solution may contain other materials (for example, salt, monosaccharide such as mannitol or glucose) in order to have isotonicity with blood.

The beta-alanine derivative of the present invention may be used as a pharmaceutically acceptable salt, wherein the salt may be acid addition salts formed by pharmaceutically acceptable free acids. The acid addition salt is obtained from inorganic acids such as hydrochloric acid, nitric acid, phosphoric acid, sulfuric acid, hydrobromic acid, hydriodic acid, nitrous acid or phosphorous acid, non-toxic organic acids such as aliphatic mono and dicarboxylate, phenyl-substituted alkanoate, hydroxy alkanoate and alkanedioate, aromatic acids, aliphatic and aromatic sulfonic acids, organic acids such as acetic acid, benzoic acid, citric acid, lactic acid, maleic acid, gluconic acid, methanesulfonic acid, 4-toluenesulfonic acid, tartaric acid, fumaric acid. An example of the pharmaceutically nontoxic salt includes sulfate, pyrosulfate, bisulfate, sulfite, bisulfite, nitrate, phosphate, mono-hydrogen phosphate, dihydrogen phosphate, meta-phosphate, pyrophosphate chloride, bromide, iodide, fluoride, acetate, propionate, decanoate, caprylate, acrylate, formate, isobutyrate, caprate, heptanoate, propioleate, oxalate, malonate, succinate, suberate, sebacate, fumarate, maleate, butyne-1,4-dioate, hexane-1,6-dioate, benzoate, chlorobenzoate, methylbenzoate, dinitro benzoate, hydroxybenzoate, methoxybenzoate, phthalate, terephthalate, benzene sulfonate, toluene sulfonate, chlorobenzene sulfonate, xylene sulfonate, phenylacetate, phenyl propionate, phenyl butyrate, citrate, lactate, β-hydroxybutyrate, glycolate, maleate, tartrate, methane sulfonate, propane sulfonate, naphthalene-1-sulfonate, naphthalene-2-sulfonate or mandelate, but the present invention is not limited thereto.

The acid addition salt according to the present invention may be prepared by generally known methods. For example, the acid addition salt may be prepared by dissolving the derivative of Chemical Formula 1 in organic solvents such as methanol, ethanol, acetone, methylene chloride, acetonitrile, and the like, and adding organic acid or inorganic acid thereto to thereby obtain a precipitate, then filtering and drying the produced precipitate, or may be prepared by distillation under reduced pressure with the solvent and excessive amounts of acids, followed by a drying process or crystallization in the presence of organic solvents.

In addition, pharmaceutically acceptable metallic salt may be prepared using a base. Alkali metal or alkali earth metal salt is obtained by dissolving a compound in an excessive amount of alkali metal hydroxide or alkali earth metal hydroxide solution, filtering non-dissolved compound salt, and evaporating and drying the filtrate. Here, in view of pharmaceutical preparation, sodium salt, potassium salt, or calcium salt is appropriate as the metal salt. In addition, corresponding silver salts are obtained by reacting alkali metal or alkali earth metal salts with suitable silver salt (for example, silver nitrate). Further, the present invention includes not only the beta-alanine derivative represented by Chemical Formula 1 above and pharmaceutically acceptable salts thereof, but also solvates, hydrates, stereisoomers which are capable of being prepared therefrom.

In addition, the compound of the present invention may contain at least one asymmetric carbon atom, and may be present as a racemate and an optically active form. The compound and enantiomers thereof are included in the category of the present invention.

In addition, the compound of the present invention may be present not only as a non-solvated form with pharmaceutically acceptable solvents, for example, water, ethanol, and the like, but also as a solvated form. In general, the solvated form is regarded as the same as the non-solvated form for objects of the present invention. The compound may be present as at least one crystalline state, that is, as a cocrystal, polymorph, or may be present as an amorphous solid. All of the above-mentioned forms are included in the scope and the claims of the present invention.

As shown in the following Reaction Formula 1, in preparation of the beta-alanine derivative represented by Chemical Formula 1 above according to the present invention, a compound represented by the following Chemical Formula A may be reacted with a beta-alanine derivative to synthesize a derivative represented by a compound B. The compound B may be reacted in acidic conditions to be converted into a compound C, followed by coupling with various organic acids, thereby synthesizing various compounds represented by Chemical Formula 1:

Reaction Formula 1

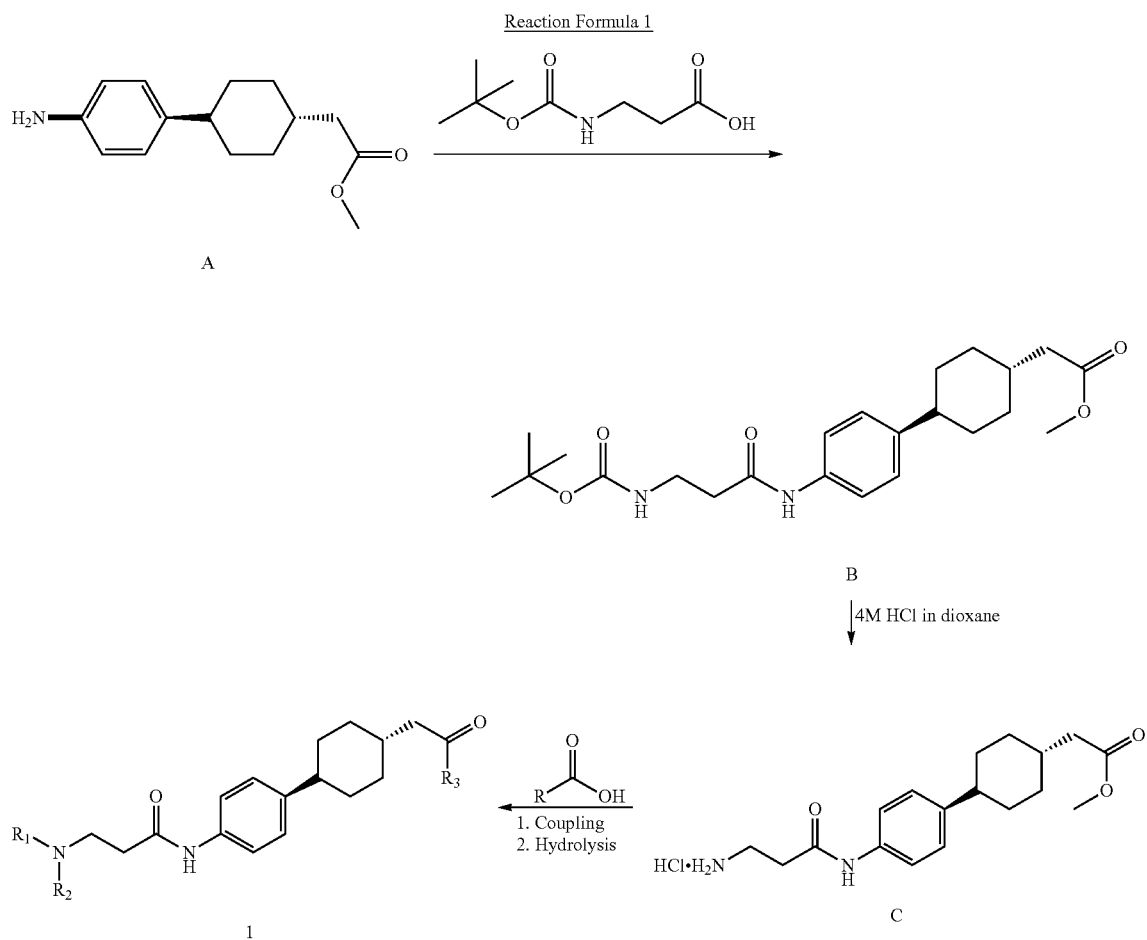

In addition, the compound represented by Chemical Formula 1 may be prepared by a method shown in the following Reaction Formula 2. A compound represented by the following Chemical Formula D may be synthesized by coupling beta-alanine methyl ester with various organic acids, and the obtained product may be coupled with the compound represented by Chemical Formula A, thereby synthesizing a compound represented by Chemical Formula E. The compound represented by Chemical Formula E may be hydrolyzed or may be reacted with other substituents, thereby obtaining various kinds of final compounds represented by Chemical Formula 1.

Reaction Formula 2

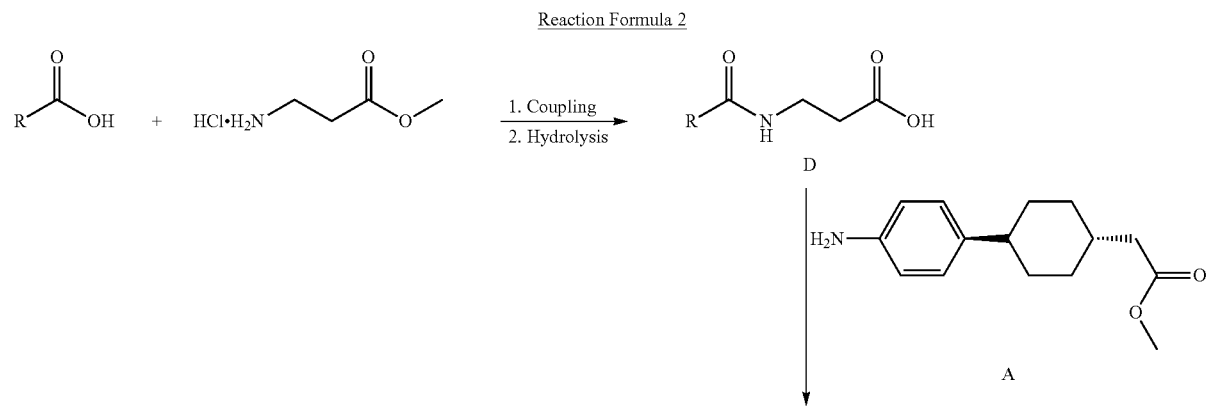

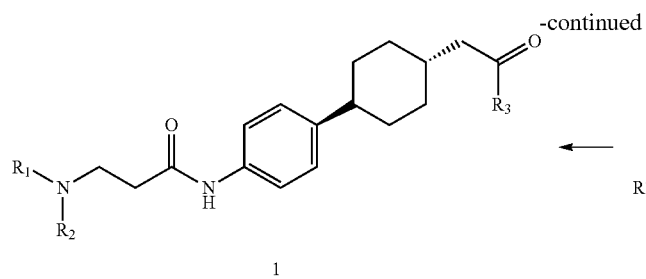
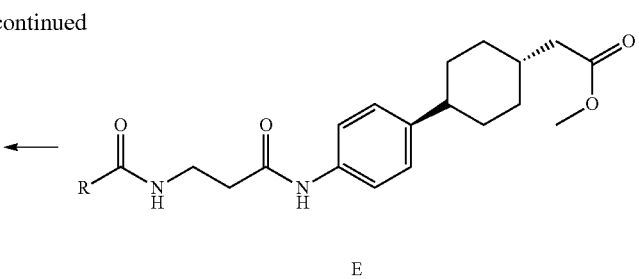

Hereinafter, each detailed synthetic method of beta-alanine derivative is as follows.

Hereinafter, the present invention is described through Preparation Examples, Examples, and Experimental Examples in detail. The following Examples and Experimental Examples are for merely exemplifying the present invention, and therefore, the scope of the present invention is not limited to the following examples.

Preparation Example 1

Preparation of [4-(4-aminophenyl)cyclohexyl]acetic acid methyl ester

Step 1: [4-(4-hydroxyphenyl)cyclohexylidene]acetic acid methyl ester

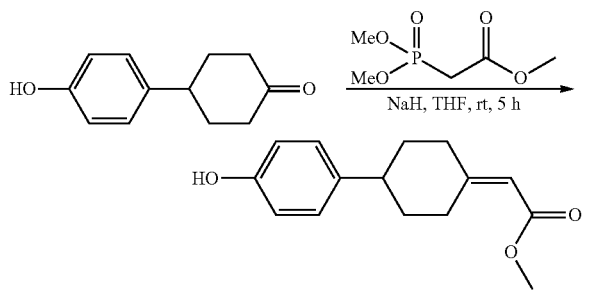

60% suspension mixed with NaH mineral oil (7.6 g, 0.19 mol) was added to trimethyl phosphonoacetate (22.8 mL, 0.15 mol) solution dissolved in anhydrous tetrahydrofuran (655 mL) under 0° C. nitrogen gas. 4-(4-hydroxyphenyl) cyclohexanone (25 g, 0.13 mol) solution dissolved in tetrahydrofuran (525 mL) was slowly added thereto at 25° C. Then, the reaction mixture was stirred at room temperature for 5 hours, cooled with water, and extracted with ethyl acetate. The mixed organic phase was washed with brine and dried with $Na_2SO_4$. The solvent was reduced under reduced pressure to obtain [4-(4-hydroxyphenyl)cyclohexylidene]acetic acid methyl ester as a white solid (31.3 g, 97%).

$^1$H NMR (300 MHz, DMSO-$d_6$): δ 9.14 (s, 1H), 7.00 (d, J=8 Hz, 2H), 6.65 (d, J=7.8 Hz), 5.69 (s, 1H), 3.86-3.76 (m, 1H), 3.60 (s, 3H), 2.76-2.63 (m, 1H), 2.42-2.24 (m, 2H), 2.07-1.86 (m, 3H), 1.57-1.33 (m, 2H).

Step 2: Trans [4-(4-hydroxyphenyl)cyclohexyl]acetic acid methyl ester

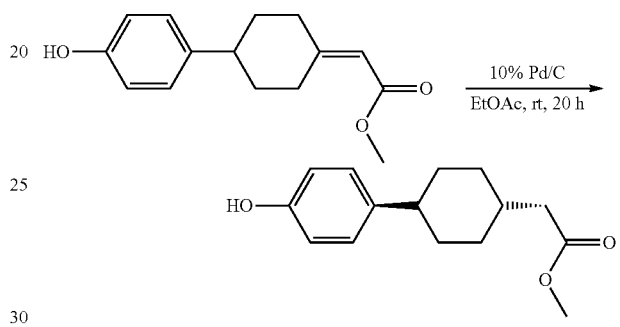

[4-(4-hydroxyphenyl)cyclohexylidene]acetic acid methyl ester (29 g, 0.12 mol) and 10% pd/c (2.9 g) were put into ethyl acetate and stirred under 25° C. hydrogen gas for 24 hours. The reaction mixture was filtered with celite and concentrated in the vacuum to obtain a yellow solid. The mixture was dissolved in hot ethyl acetate (29 mL) and cooled to reach ambient temperature. The reaction mixture was cooled with ice water again, a filtrate was filtered and washed with ethyl acetate (15 mL) to obtain trans [4-(4-hydroxyphenyl)cyclohexyl]acetic acid methyl ester as a white solid (12.6 g, 43%).

$^1$H NMR (500 MHz, CDCl$_3$): δ 7.06 (d, J=8.5 Hz, 2H), 6.75 (d, J=8.5 Hz, 2H), 4.66 (s, 1H), 3.68 (s, 3H), 2.44-2.35 (m, 1H), 2.24 (d, J=6.9 Hz, 2H), 1.90-1.78 (m, 5H), 1.50-1.39 (m, 2H), 1.19-1.07 (m, 2H).

Step 3: [4-(4-trifluoromethanesulfonyloxyphenyl)cyclohexyl]acetic acid methyl ester

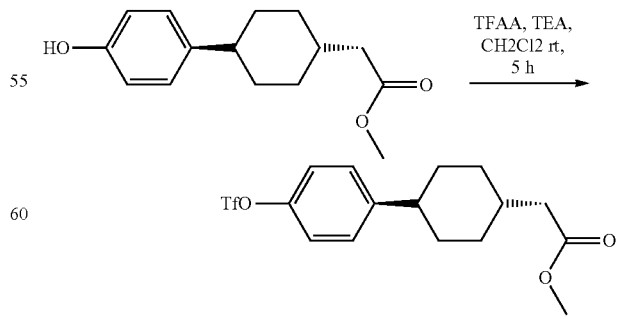

Triethyl amine (8.1 mL, 57.99 mmol) was added dropwise to [4-(4-hydroxyphenyl)cyclohexyl]acetic acid methyl ester (9.6 g, 38.66 mmol) dissolved in CH$_2$Cl$_2$ and trifluoromethane sulphonic acid (8.1 mL, 48.32 mmol) solution at 0° C. The reaction mixture was warmed up to reach ambient temperature and stirred for 5 hours. The reaction mixture was poured into 200 mL water and extracted with CH$_2$Cl$_2$. The organic phase was washed with saturated sodium bicarbonate solution, brine and anhydrous Na$_2$SO$_4$. The solvent was reduced under reduced pressure, the residue was purified in silica gel using CH$_2$Cl$_2$ as an eluent to obtain [4-(4-trifluoromethanesulfonyloxyphenyl)cyclohexyl]acetic acid methyl ester (13.4 g, 91%) as a white solid.

$^1$H NMR (500 MHz, DMSO-d$_6$): δ 7.47-7.32 (m, 4H), 3.59 (s, 3H), 2.58-2.50 (m, 1H), 2.24 (d, J=6.2 Hz, 2H), 1.82-1.69 (m, 5H), 1.51-1.39 (m, 2H), 1.18-1.09 (m, 2H).

Step 4: Trans [4-(4-aminophenyl)cyclohexyl]acetic acid methyl ester

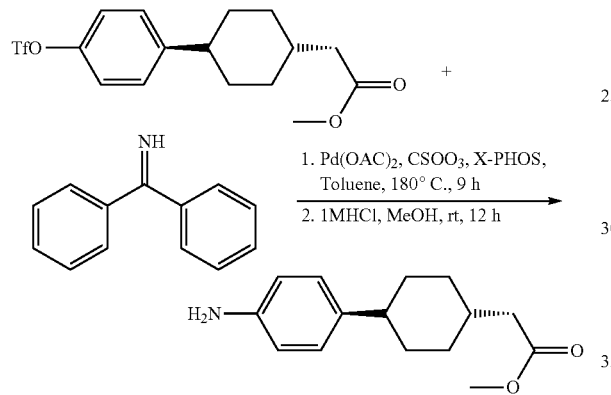

Benzophenone imine (5.8 mL, 34.7 mmol) was added to a mixed solution of trans [4-(4-trifluoromethanesulfonyloxyphenyl)cyclohexyl]acetic acid methyl ester (12 g, 31.54 mmol), cesium carbonate (11.3 g, 34.7 mmol), palladium acetate (708 mg, 3.15 mmol), X-phos (3 g, 6.31 mmol) and toluene (78 mL) in a sealed tube. The mixture was purified 5 times with nitrogen and stirred at 180° C. for 10 hours. The prepared solution was cooled to remove the solvent under reduced pressure, the residue was sectioned with ether (600 mL) and water (600 mL) to separate each layer. The aqueous solution layer was extracted with ether (3×180 mL), a mixed organic layer was dried with anhydrous Na$_2$SO$_4$ and concentrated under vacuum to obtain yellow oil. The obtained oil was used without further purification (crude 21 g). The oil was dissolved in methanol (252 mL) and the solution was cooled to be 4° C. Hydrochloric acid (84 mL) 1M was slowly added thereto while maintaining the temperature less than 7° C. The solution was warmed up for 16 hours to ensure the temperature was ambient temperature. Then, methanol was removed in a vacuum state and the reaction mixture was diluted with water (210 mL). The liquid-phase mixture was washed with ether (2×180 mL) and the mixed organic layer was washed with 1M hydrochloric acid (2×90 mL). The mixed aqueous solution layer was basified with a 10% sodium carbonate solution up to pH of 9 to thereby obtain a filtrate. Ethyl acetate (3200 mL) was added thereto to thereby separate each layer. The organic layer was dried with MgSO$_4$ and concentrated in a vacuum state until a filtrate was formed. The mixture was cooled, filtered, and washed with heptane (24 mL) to obtain trans[4-(4-aminophenyl)cyclohexyl]acetic acid methyl ester (4.247% was obtained by two steps) as a white solid.

$^1$H NMR (500 MHz, CDCl$_3$): δ 6.99 (d, J=8.2 Hz, 2H), 6.63 (d, J=8.2 Hz, 2H), 3.68 (s, 3H), 3.54 (s, 2H), 2.40-2.31 (m, 1H), 2.24 (d, J=6.7 Hz, 2H), 1.90-1.77 (m, 5H), 1.50-1.38 (m, 2H), 1.18-1.06 (m, 2H).

Example 1

Trans-[4-(4-{3-[(2-phenyl-5-trifluoromethyloxazole-4-carbonyl)amino]propionylamino}phenyl)cyclohexyl]-acetic acid methyl ester (Compound 5)

Step 1: Preparation of 3-[(2-phenyl-5-trifluoromethyloxazole-4-carbonyl)amino]propionic acid

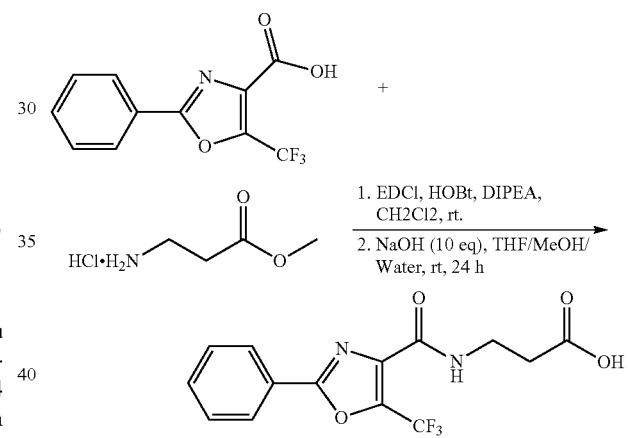

2-phenyl-5-trifluoromethyloxazole-4-carboxylic acid (200 mg, 0.78 mmol), EDCI (372.7 mg, 1.94 mmol), methyl 3-aminopropionate (16.7 mg, 1.17 mmol), HOBt (157.6 mg, 1.17 mmol) and ethyldiisopropylamine (352.6 mg, 2.7 mmol) dissolved in dichloromethane (15 mL) were stirred for 24 hours. The reaction mixture was diluted with aqueous NaHCO$_3$ and extracted with dichloromethane. The extract was washed with brine and dried with anhydrous sodium sulfate and concentrated under vacuum. The residue was purified by silica gel column chromatography to obtain the desired compound (265 mg, 99%) as a white solid.

NaOH (309.7 mg, 7.7 mmol) was added to 3-[(2-phenyl-5-trifluoromethyloxazole-4-carbonyl)amino]propionic acid methyl ester (265 mg, 0.77 mmol) dissolved in THF/MeOH/water (25 mL, 4:2:1). The reaction mixture was stirred at 25° C. for 12 hours and concentrated under vacuum. The residue was acidified with 1M HCl up to pH 2 and extracted with ethyl acetate. The extract was washed with brine and dried with anhydrous sodium sulfate and concentrated under vacuum to obtain the desired compound (250 mg, 98%) as a white solid.

Step 2: Preparation of trans-[4-(4-{3-[(2-phenyl-5-trifluoromethyloxazole-4-carbonyl)amino]propionylamino}phenyl)cyclohexyl]acetic acid methyl ester

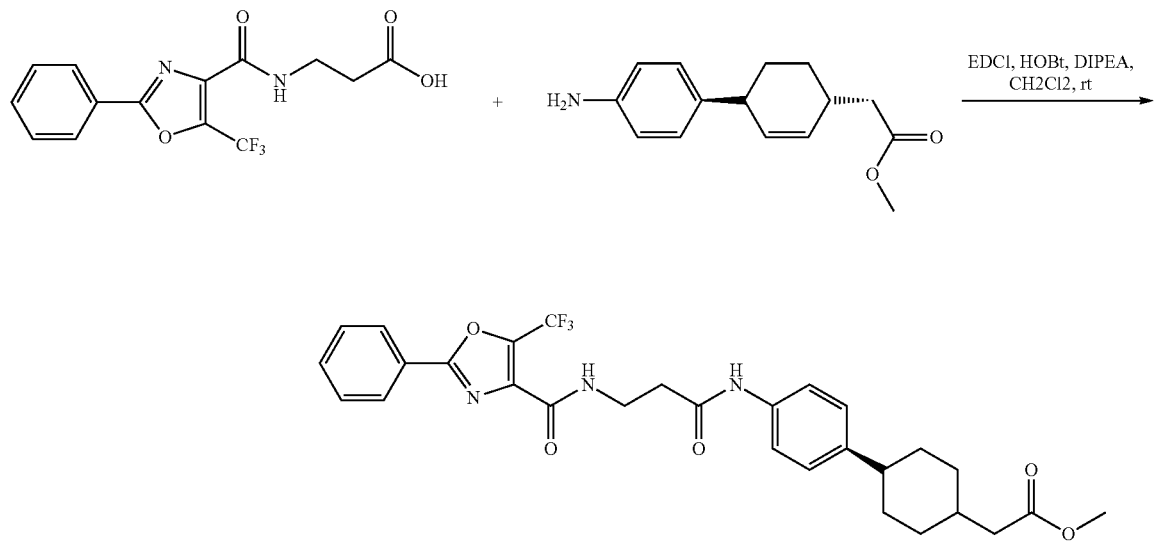

Trans-[4-(4-aminophenyl)cyclohexyl]acetic acid methyl ester (150 mg, 0.6 mmol), EDCI (290.7 mg, 1.5 mmol), 3-[(2-phenyl-5-trifluoromethyloxazole-4-carbonyl)amino] propionic acid (228.9 mg, 0.7 mmol), HOBt (123 mg, 0.91 mmol) and ethyldiisopropylamine (275 mg, 0.21 mmol) dissolved in dichloromethane (15 mL) were stirred for 24 hours. The reaction mixture was diluted with aqueous NaHCO₃ and extracted with dichloromethane. The extract was washed with brine and dried with anhydrous sodium sulfate and concentrated under vacuum. The residue was purified by silica gel column chromatography to obtain the desired compound (330 mg, 98%) as a white solid.

$^1$H NMR (300 MHz, CDCl$_3$): δ 8.07 (d, J=6, 7 Hz, 2H), 7.88-7.79 (m, 1H), 7.62-7.47 (m, 4H), 7.43 (d, J=8.3 Hz, 2H), 7.15 (d, J=8.2 Hz, 2H), 3.88-3.78 (m, 2H), 3.68 (s, 3H), 2.75 (t, J=5.6 Hz, 2H), 2.48-2.36 (m, 1H), 2.24 (d, J=6.5 Hz, 2H), 1.93-1.78 (m, 5H), 1.56-1.37 (m, 2H), 1.22-1.04 (m, 2H).

Example 2

Preparation of trans-[4-(4-{3-[(2-phenyl-5-trifluoromethyloxazole-4-carbonyl)amino]propionylamino}phenyl)cyclohexyl]acetic acid (Compound 6)

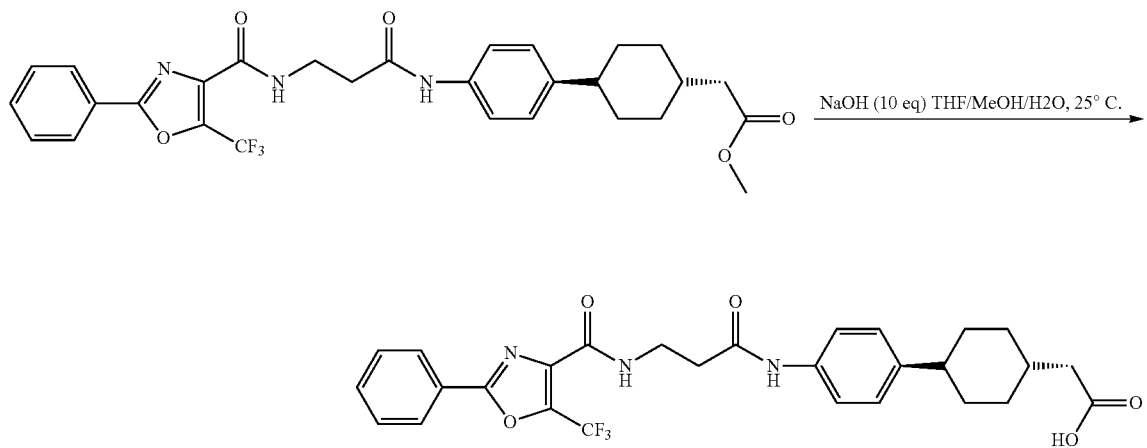

NaOH (241 mg, 5.7 mmol) was added to [4-(4-{3-[(2-phenyl-5-trifluoromethyloxazole-4-carbonyl-amino]propionylamino}phenyl)cyclohexyl]acetic acid methyl ester (320 mg, 0.57 mmol) dissolved in THF/MeOH/water (25 mL, 3:2:1). The reaction mixture was stirred at 25° C. for 5 hours and concentrated under vacuum. The residue was acidified with 1M HCl up to pH of 2 and extracted with ethyl acetate. The extract was washed with brine and dried with anhydrous sodium sulfate and concentrated under vacuum. Acetonitrile was added thereto and cooled to obtain a filtrate, and the filtrate was filtered and separated to obtain the desired compound (275 mg, 88%) as a white solid.

$^1$H NMR (500 MHz, DMSO-$d_6$): δ 11.99 (s, 1H), 9.91 (s, 1H), 8.76 (t, J=5.4 Hz, 1H), 8.08-8.04 (m, 2H), 7.69-7.59 (m, 3H), 7.48 (d, J=8.7 Hz, 2H), 7.13 (d, J=8.7 Hz, 2H), 3.56 (q, J=6.7 Hz, 2H), 2.63 (t, J=6.9 Hz, 2H), 2.43-2.35 (m, 1H), 2.13 (d, J=7.0 Hz, 2H), 1.83-1.65 (m, 5H), 1.47-1.36 (m, 2H), 1.15-1.03 (m, 2H).

Example 3

Preparation of trans-[4-(4-{3-[(1-phenyl-3-trifluoromethyl-1H-pyrazole-4-carbonyl)amino]propionylamino}phenyl)cyclohexyl]acetic acid (Compound 7)

Step 1: Preparation of 3-[(1-phenyl-3-trifluoromethyl-1H-pyrazole-4-carbonyl)amino]propionic acid

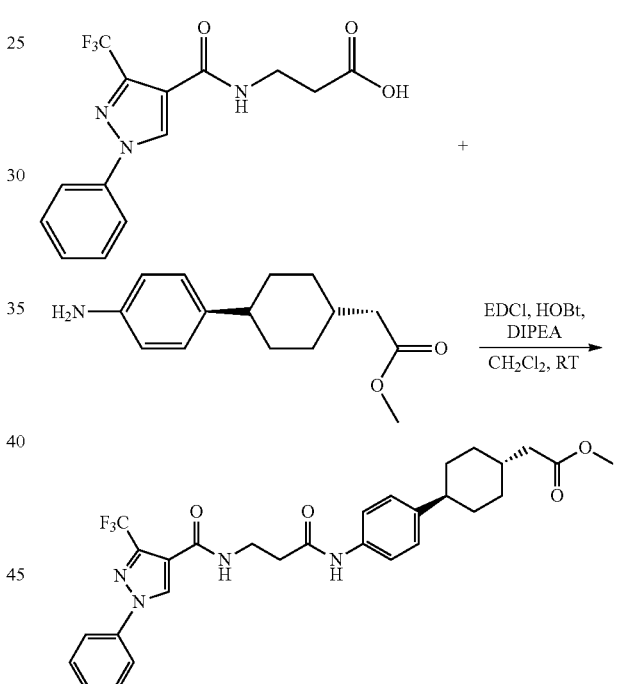

1-phenyl-3-trifluoromethyl-1H-pyrazole-4-carboxylic acid (150 mg, 0.57 mmol), EDCI (280.6 mg, 1.5 mmol), methyl 3-aminopropionate (163.5 mg, 1.17 mmol), HOBt (118.7 mg, 0.8 mmol) and ethyldiisopropylamine (265.5 mg, 2.1 mmol) dissolved in dichloromethane (15 mL) were stirred for 24 hours. The reaction mixture was diluted with aqueous NaHCO$_3$ and extracted with dichloromethane. The extract was washed with brine and dried with anhydrous sodium sulfate and concentrated under vacuum. The residue was purified by silica gel column chromatography to obtain the desired compound (181 mg, 91%) as a white solid.

NaOH (212.1 mg, 5.3 mmol) was added to 3-[(1-phenyl-3-trifluoromethyl-1H-pyrazole-4-carbonyl)amino]propionic acid methyl ester (181 mg, 0.53 mmol) dissolved in THF/MeOH/water (25 mL, 4:2:1). The reaction mixture was stirred at 25° C. for 5 hours and concentrated under vacuum. The residue was acidified with 1M HCl up to pH 2 and extracted with ethyl acetate. The extract was washed with brine and dried with anhydrous sodium sulfate and concentrated under vacuum to obtain the desired compound (170 mg, 98%) as a white solid.

Step 2: Preparation of trans-[4-(4-{3-[(1-phenyl-3-trifluoromethyl-1H-pyrazole-4-carbonyl)amino]propionylamino}phenyl)cyclohexyl]acetic acid methyl ester

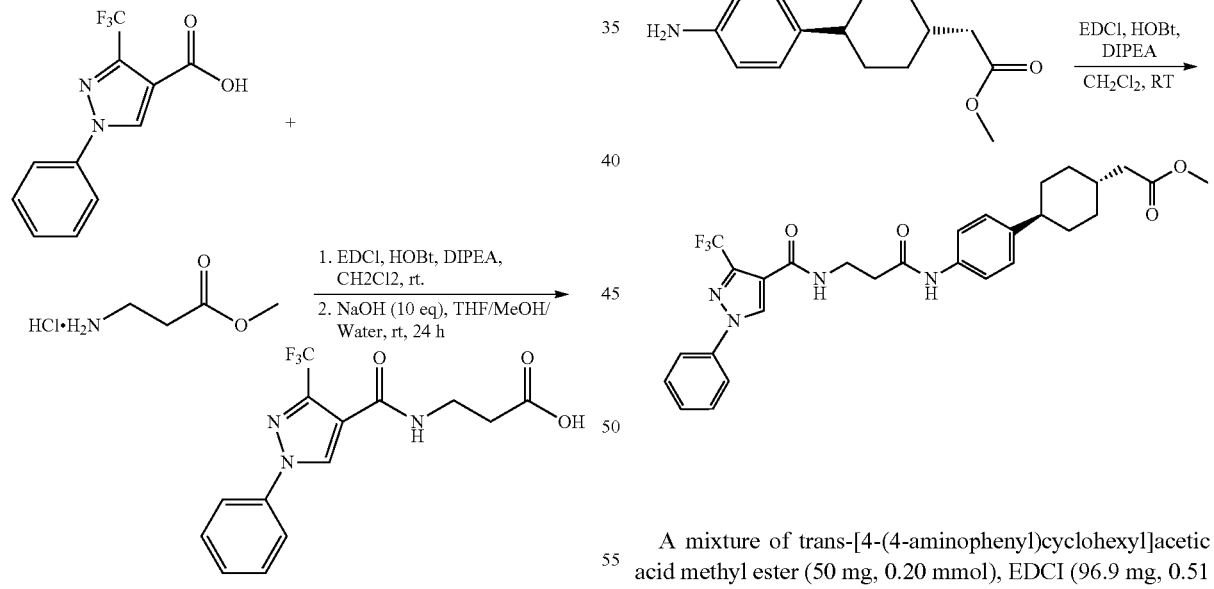

A mixture of trans-[4-(4-aminophenyl)cyclohexyl]acetic acid methyl ester (50 mg, 0.20 mmol), EDCI (96.9 mg, 0.51 mmol), 3-[(1-phenyl-3-trifluoromethyl-1H-pyrazole-4-carbonyl)amino]propionic acid (79.4 mg, 0.24 mmol), HOBt (41 mg, 0.3 mmol) and ethyldiisopropylamine (91.7 mg, 0.71 mmol) dissolved in dichloromethane (15 mL) were stirred for 24 hours. The reaction mixture was diluted with aqueous NaHCO$_3$ and extracted with dichloromethane. The extract was washed with brine and dried with anhydrous sodium sulfate and concentrated under vacuum. The residue was purified by silica gel column chromatography to obtain the desired compound (102 mg, 91%) as a white solid.

Step 3: Preparation of trans-[4-(4-{3-[(1-phenyl-3-trifluoromethyl-1H-pyrazole-4-carbonyl)amino]propionylamino}phenyl)cyclohexyl]acetic acid

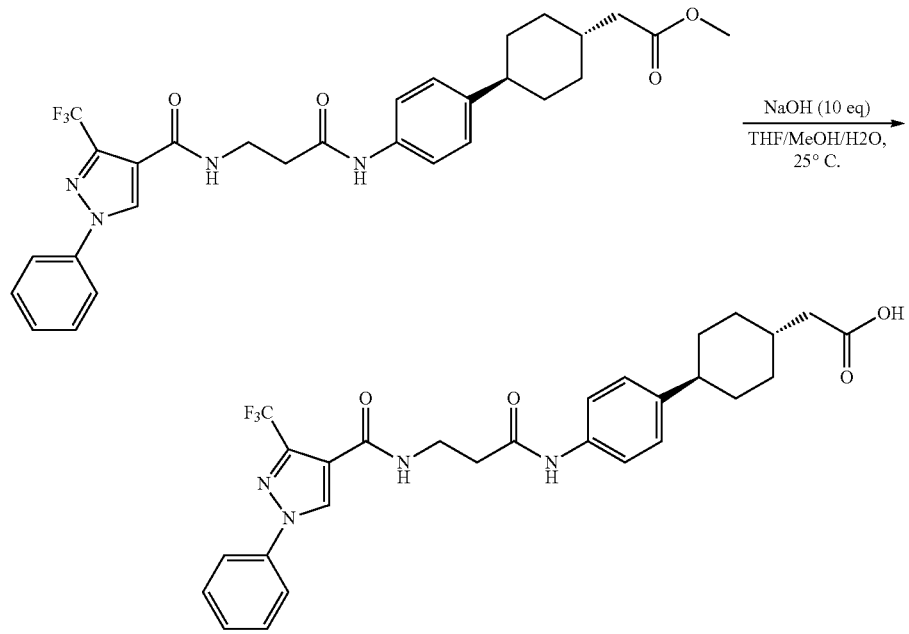

NaOH (71.9 mg, 1.8 mmol) was added to trans-[4-(4-{3-[(1-phenyl-3-trifluoromethyl-1H-pyrazole-4-carbonyl)amino]propionylamino}phenyl)cyclohexyl]acetic acid methyl ester (100 mg, 0.18 mmol) dissolved in THF/MeOH/water (25 mL, 3:2:1). The reaction mixture was stirred at 25° C. for 5 hours and concentrated under vacuum. The residue was acidified with 1M HCl up to pH of 2 and extracted with ethyl acetate. The extract was washed with brine and dried with anhydrous sodium sulfate and concentrated under vacuum. Acetonitrile was added thereto and cooled to obtain a filtrate, and the filtrate was filtered and separated to obtain the desired compound (95 mg, 98%) as a white solid.

$^1$H NMR (500 MHz, DMSO-$d_6$): δ 12.02 (s, 1H), 9.91 (s, 1H), 9.07 (s, 1H), 8.50-8.44 (m, 1H), 7.80 (d, J=7.7 Hz, 2H), 7.61-7.56 (m, 2H), 7.51-7.43 (m, 3H), 7.13 (d, J=8.5 Hz, 2H), 3.53-3.48 (m, 2H), 2.59 (t, J=6.8 Hz, 2H), 2.41-2.34 (m, 1H), 2.11 (d, J=6.8 Hz, 2H), 1.83-1.66 (m, 5H), 1.45-1.35 (m, 2H), 1.13-1.03 (m, 2H).

Example 4

Preparation of trans-{4-[4-(3-{[2-(2-chlorophenyl)-5-trifluoromethyloxazole-4-carbonyl]amino}propionylamino)phenyl]cyclohexyl}acetic acid methyl ester (Compound 10)

Step 1: Preparation of 3-{[2-2-chlorophenyl]-5-trifluoromethyloxazole-4-carbonyl]amino}propionic acid

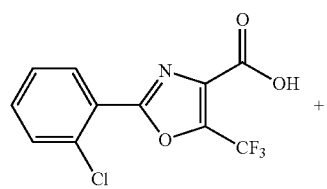

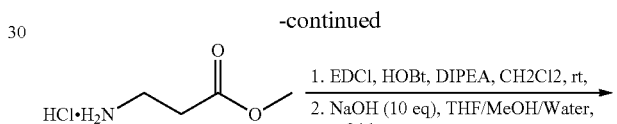

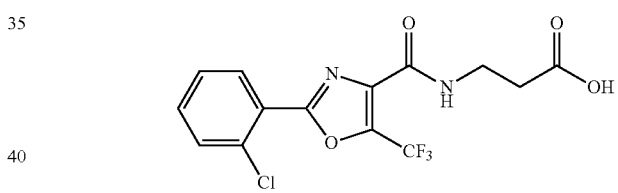

A mixture of 2-(2-chlorophenyl)-5-trifluoromethyloxazole-4-carboxylic acid (150 mg, 0.51 mmol), EDCI (146.5 mg, 1.3 mmol), 3-aminopropionic acid methyl ester hydrochloride salt (107.6 mg, 0.77 mmol), HOBt (104.3 mg, 0.77 mmol) and ethyldiisopropylamine (233.3 mg, 1.8 mmol) dissolved in dichloromethane (15 mL) were stirred for 24 hours. The reaction mixture was diluted with aqueous NaHCO$_3$ and extracted with dichloromethane. The extract was washed with brine and dried with anhydrous sodium sulfate and concentrated under vacuum. The residue was purified by silica gel column chromatography to obtain the desired compound (190 mg, 98%) as a white solid.

NaOH (201.7 mg, 5.04 mmol) was added to 3-{[2-(2-chlorophenyl)-5-trifluoromethyloxazole-4-carbonyl]amino}propionic acid methyl ester (190 mg, 0.504 mmol) dissolved in THF/MeOH/water (25 mL, 4:2:1). The reaction mixture was stirred at 25° C. for 5 hours and concentrated under vacuum. The residue was acidified with 1M HCl up to pH 2 and extracted with ethyl acetate. The extract was washed with brine and dried with anhydrous sodium sulfate and concentrated under vacuum to obtain the desired compound (160 mg, 88%) as a white solid.

Step 2: Preparation of trans-{4-[4-(3-{[2-(2-chlorophenyl)-5-trifluoromethyloxazole-4-carbonyl]amino}propionylamino)phenyl]cyclohexyl}acetic acid methyl ester

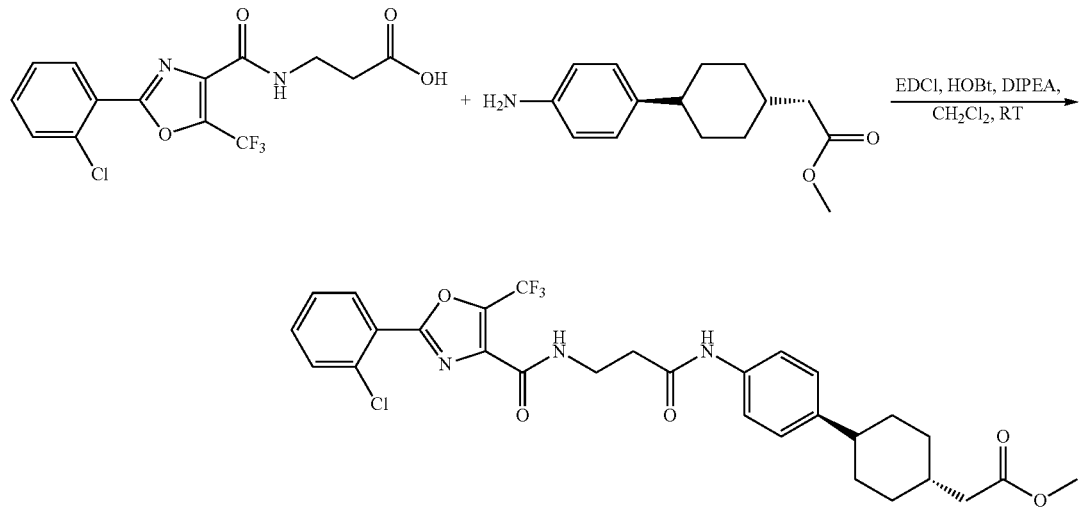

Trans-[4-(4-aminophenyl)cyclohexyl]acetic acid methyl ester (70 mg, 0.28 mmol), EDCI (135.6 mg, 0.71 mmol), 3-{[2-(2-chlorophenyl)-5-trifluoromethyloxazole-4-carbonyl]amino}propionic acid (123.2 mg, 0.34 mmol), HOBt (57.4 mg, 0.23 mmol) and ethyldiisopropylamine (128.3 mg, 0.99 mmol) dissolved in dichloromethane (15 mL) were stirred for 24 hours. The reaction mixture was diluted with aqueous NaHCO₃ and extracted with dichloromethane. The extract was washed with brine and dried with anhydrous sodium sulfate and concentrated under vacuum. The residue was purified by silica gel column chromatography to obtain the desired compound (165 mg, 99%) as a white solid.

$^1$H NMR (300 MHz, CDCl$_3$): δ 8.02 (d, J=7.2 Hz, 1H), 7.88-7.78 (m, 1H), 7.59-7.36 (m, 6H), 7.14 (d, J=8.2 Hz, 2H), 3.89-3.78 (m, 2H), 3.68 (s, 3H), 2.74 (t, J=5.5 Hz, 2H), 2.49-2.34 (m, 1H), 2.24 (d, J=6.5 Hz, 2H), 1.93-1.79 (m, 5H), 1.56-1.37 (m, 2H), 1.22-1.04 (m, 2H).

Example 5

Preparation of trans-{4-[4-(3-{[2-(2-chlorophenyl)-5-trifluoromethyloxazole-4-carbonyl]amino}propionylamino)phenyl]cyclohexyl}acetic acid (Compound 11)

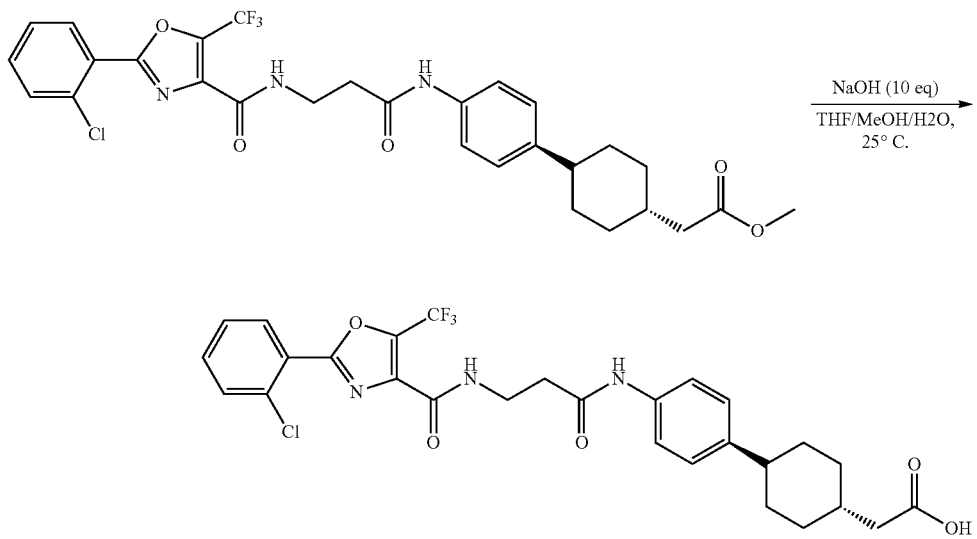

NaOH (108 mg, 2.7 mmol) was added to trans-{4-[4-(3-{[2-(2-chlorophenyl)-5-trifluoromethyloxazole-4-carbonyl]amino}propionylamino)phenyl]cyclohexyl}acetic acid methyl ester (160 mg, 0.27 mmol) dissolved in THF/MeOH/water (25 mL, 3:2:1). The reaction mixture was stirred at 25° C. for 5 hours and concentrated under vacuum. The residue was acidified with 1M HCl up to pH of 2 and extracted with ethyl acetate. The extract was washed with brine and dried with anhydrous sodium sulfate and concentrated under vacuum. Acetonitrile was added thereto and cooled to obtain a filtrate, and the filtrate was filtered and separated to obtain the desired compound (130 mg, 83%) as a white solid.

$^1$H NMR (500 MHz, DMSO-$d_6$): δ 12.03 (s, 1H), 9.92 (s, 1H), 8.80-8.74 (m, 1H), 8.06 (d, J=7.5 Hz, 1H), 7.72 (d, J=7.9 Hz, 1H), 7.66 (t, J=7.5 Hz, 1H), 7.58 (t, J=7.6 Hz, 1H), 7.48 (d, J=8.3 Hz, 2H), 7.13 (d, J=8.3 Hz, 2H), 3.60-3.52 (m, 2H), 2.62 (t, J=6.9 Hz, 2H), 2.42-2.34 (m, 1H), 2.12 (d, J=6.8 Hz, 2H), 1.83-1.65 (m, 5H), 1.46-1.35 (m, 2H), 1.14-1.03 (m, 2H).

Example 6

Preparation of trans-[4-(4-{3-[(2-phenyl-5-trifluoromethyloxazole-4-carbonyl)amino]propionylamino}phenyl)cyclohexyl]acetate sodium salt (Compound 22)

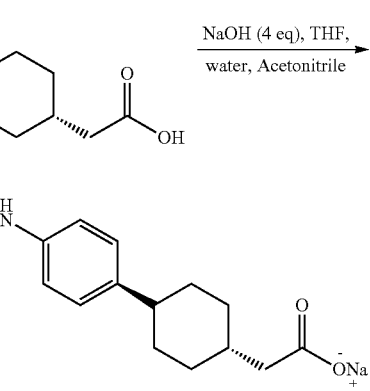

Sodium hydroxide (23.55 mg, 0.56 mmol) was added to trans-[4-(4-{3-[(2-phenyl-5-trifluoromethyloxazole-4-carbonyl)amino]propionylamino}phenyl)cyclohexyl]acetic acid (80 mg, 0.15 mmol) dissolved in THF (8 mL) and water (3 mL) at room temperature. The obtained mixture was stirred at 40° C. for 2 hours. When water is added, most of the organic solvents may be reduced under reduced pressure. Acetonitrile was added thereto and cooled to obtain a filtrate, and the filtrate was filtered and separated to obtain a sodium salt of the desired compound.

$^1$H NMR (300 MHz, DMSO-$d_6$): δ10.15 (s, 1H), 8.93-8.84 (m, 1H), 8.06 (d, J=7.0 Hz, 2H), 7.70-7.56 (m, 3H), 7.49 (d, J=8.0 Hz, 2H), 7.11 (d, J=8.2 Hz, 2H), 3.61-3.51 (m, 2H), 2.68-2.59 (m, 2H), 2.40-2.27 (m, 1H), 1.86-1.63 (m, 7H), 1.43-1.47 (m, 2H), 1.04-0.88 (m, 2H).

Example 7

Preparation of trans-{4-[4-(3-tert-butoxycarbonylaminopropionylamino)phenyl]cyclohexyl}acetic acid methyl ester (Compound 23)

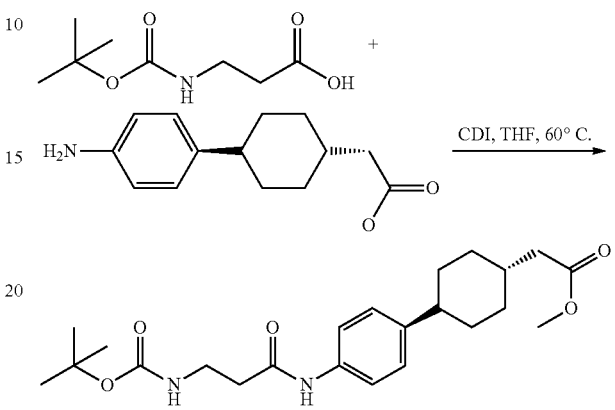
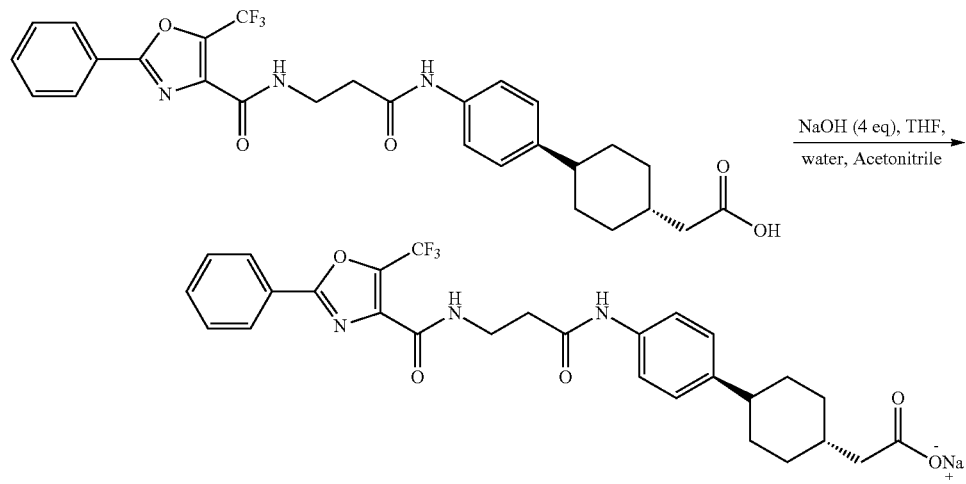

Trans-[4-(4-aminophenyl)cyclohexyl]acetic acid methyl ester (500 mg, 2.02 mmol) was added to a stirred solution of 3-tert-butoxycarbonylamino-propionic acid (765 mg, 4.04 mmol) and 1,1-carbonyldiimidazole (656 mg, 4.04 mmol) dissolved in tetrahydrofuran at 60° C. After 8 hours, the reaction mixture was diluted with dichloromethane, washed with saturated sodium bicarbonate and brine, and dried with anhydrous magnesium sulfate and concentrated under vacuum. The residue was purified by silica gel column chromatography to obtain {4-[4-(3-tert-butoxycarbonylaminopropyonylamino)phenyl]cyclohexyl}acetic acid methyl ester (838 mg, 99%, white solid).

$^1$H NMR (300 MHz, CDCl$_3$): δ 7.48 (s, 1H), 7.42 (d, J=8.2 Hz, 2H), 7.15 (d, J=8.2 Hz, 2H), 5.19-5.10 (m, 1H), 3.68 (s, 3H), 3.53-3.44 (m, 2H), 2.58 (t, J=5.5 Hz, 2H), 2.50-2.37 (m, 1H) 2.25 (d, J=6.5 Hz, 2H), 1.97-1.79 (m, 5H), 1.51-1.37 (m, 11H), 1.23-1.05 (m, 2H).

Example 8

Preparation of trans-{4-[4-(3-tert-butoxycarbonylaminopropionylamino)phenyl]cyclohexyl}acetic acid (Compound 24)

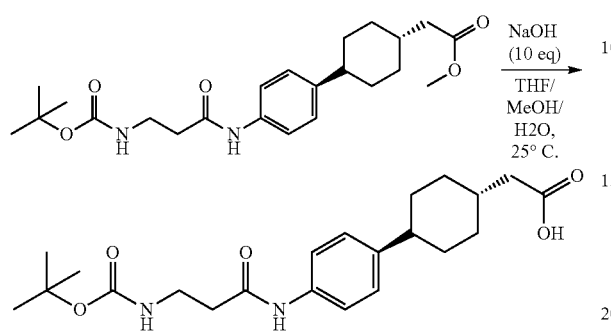

NaOH (47.8 mg, 1.19 mmol) was added to trans-{4-[4-(3-tert-butoxycarbonylaminopropionylamino)phenyl]cyclohexyl}acetic acid methyl ester (50 mg, 0.12 mmol) dissolved in THF/MeOH/water (20 mL, 3:2:1). The reaction mixture was stirred at 25° C. for 5 hours and concentrated under vacuum. The residue was acidified with 1M HCl up to pH of 2 and extracted with ethyl acetate. The extract was washed with brine and dried with anhydrous sodium sulfate and concentrated under vacuum. Acetonitrile was added thereto and cooled to obtain a filtrate, and the filtrate was filtered and separated to obtain the desired compound (47 mg, 97%) as a white solid.

$^1$H NMR (500 MHz, DMSO-$d_6$): δ12.04 (s, 1H), 9.83 (s, 1H), 7.47 (d, J=8.0 Hz, 2H), 7.12 (d, J=8.0 Hz, 2H), 6.88-6.82 (m, 1H), 3.19 (q, J=6.3 Hz, 2H), 2.43 (t, J=7.1 Hz, 2H), 2.40-2.33 (m, 1H), 2.12 (d, J=6.8 Hz, 2H), 1.84-1.64 (m, 5H), 1.47-1.33 (m, 11H), 1.14-1.02 (m, 2H).

Example 9

Trans-{4-[4-(3-aminopropionylamino)phenyl]cyclohexyl}acetic acid methyl ester hydrochloride salt (Compound 25)

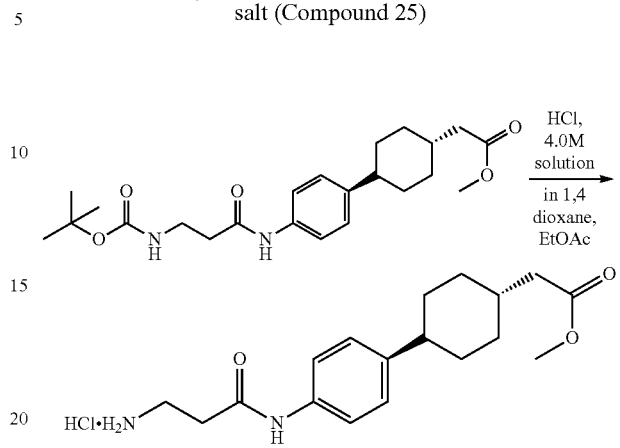

0.4M hydrogen chloride solution dissolved in 1,4-dioxane (3.2 mL) was added to trans-{4-[4-(3-tert-butoxycarbonylaminopropionylamino)phenyl]cyclohexyl}acetic acid methyl ester (800 mg, 1.91 mmol) dissolved in ethyl acetate (16 mL). The reaction mixture was stirred at 50° C. for 4 hours and slowly cooled up to 25° C. The product was collected through filtration and washed with ethyl acetate. The product was dried under vacuum to obtain the desired compound (615 mg, 91%) as a white solid.

$^1$H NMR (500 MHz, DMSO-$d_6$): δ 10.14 (s, 1H), 7.86 (s, 3H), 7.49 (d, J=8.0 Hz, 2H), 7.15 (d, J=8.0 Hz, 2H), 3.59 (s, 3H), 3.05 (t, J=6.7 Hz, 2H), 2.69 (t, J=6.7 Hz, 2H), 2.43-2.34 (m, 1H), 2.23 (d, J=6.7 Hz, 2H), 1.81-1.68 (m, 5H), 1.47-1.05 (m, 2H).

Example 10

Preparation of trans-[4-(4-{3-[(5-methyl-2-phenyloxazole-4-carbonyl)amino]propionylamino}phenyl)cyclohexyl]acetic acid (Compound 31)

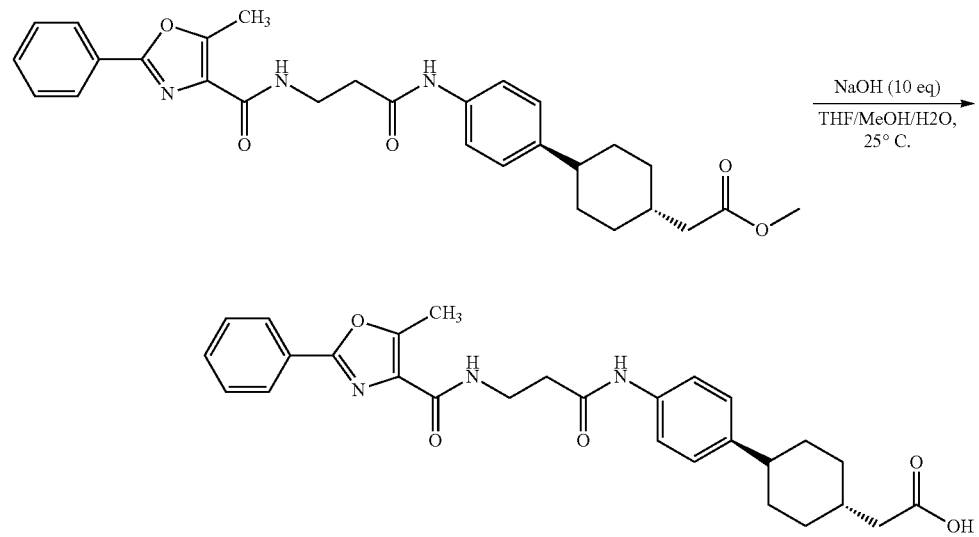

NaOH (59.6 mg, 1.5 mmol) was added to trans-[4-(4-{3-[(5-methyl-2-phenyloxazole-4-carbonyl)amino]propionylamino}phenyl)cyclohexyl]acetic acid methyl ester (75 mg, 0.15 mmol) dissolved in THF/MeOH/water (20 mL, 3:2:1). The reaction mixture was stirred at 25° C. for 5 hours and concentrated under vacuum. The residue was acidified with 1M HCl up to pH 2 and extracted with ethyl acetate. The extract was washed with brine and dried with anhydrous sodium sulfate and concentrated under vacuum. The residue was stirred with acetonitrile and filtered, then eluted with a gradient of methanol/DCM (5-10%) on a silica gel by column chromatography and purified. Therefore, the desired compound as a white solid was obtained.

$^1$H NMR (300 MHz, DMSO-$d_6$): δ 12.05 (s, 1H), 9.91 (s, 1H), 8.25-8.17 (m, 1H), 8.01-7.93 (m, 2H), 7.59-7.51 (m, 3H), 7.48 (d, J=8.4 Hz, 2H), 7.13 (d, J=8.4 Hz, 2H), 3.58-3.49 (m, 2H), 2.65 (s, 3H), 2.60 (t, 7.4 Hz, 2H), 2.44-2.31 (m, 1H), 2.12 (d, J=6.6 Hz, 2H), 1.85-1.64 (m, 5H), 1.49-1.32 (m, 2H), 1.16-0.99 (m, 2H).

Example 11

Preparation of trans-2-phenyl-5-trifluoromethyloxazole-4-carboxylic acid{2-[4-(4-carbamoylmethylcyclohexyl)phenylcarbamoyl]ethyl}amide (Compound 41)

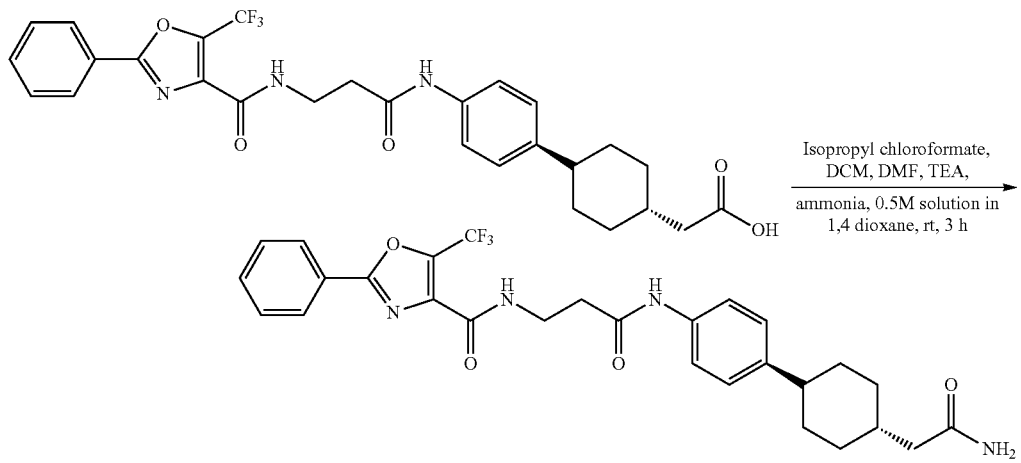

Trans-[4-(4-{3-[(2-phenyl-5-trifluoromethyloxazole-4-carbonyl)amino]propionylamino}phenyl)cyclohexyl]acetic acid (41 mg, 0.07 mmol) was added to DCM (4 mL) and DMF (1 mL) solution. Isopropyl chloroformate (0.02 mL, 0.11 mmol) and triethyl amine (0.2 mL, 0.15 mmol) were added dropwise thereto at 0° C., a temperature of the product was raised to room temperature, and stirred for 2 hours. Then, 0.5 M ammonia dissolved in 1,4-dioxane was added and stirred for 2 hours. Ethyl acetate (20 mL) and water (40 mL) were added to the reaction mixture. Then, the organic layer was separated and the product was dried with anhydrous sodium sulfate to prepare a solid under reduced pressure. The product was purified by chromatography using methanol/DCM 2-10% to obtain the desired compound (38 mg, 93%) as a white solid.

$^1$H NMR (300 MHz, DMSO-$d_6$) δ 9.93 (s, 1H), 8.83-8.74 (m, 1H), 8.11-8.03 (m, 2H), 7.72-7.56 (m, 3H), 7.48 (d, J=8.3 Hz, 2H), 7.13 (d, J=8.3 Hz, 2H), 3.61-3.51 (m, 2H), 2.68-2.59 (m, 2H), 2.45-2.31 (m, 1H), 2.19 (d, J=6.3 Hz, 2H), 1.86-1.66 (m, 5H), 1.50-1.31 (m, 2H), 1.18-0.99 (m, 2H).

Example 12

Preparation of trans-[4-(4-{3-[(1-o-tolyl-3-trifluoromethyl-1H-pyrazole-4-carbonyl)amino]propionylamino}phenyl)cyclohexyl]acetic acid methyl ester (Compound 44)

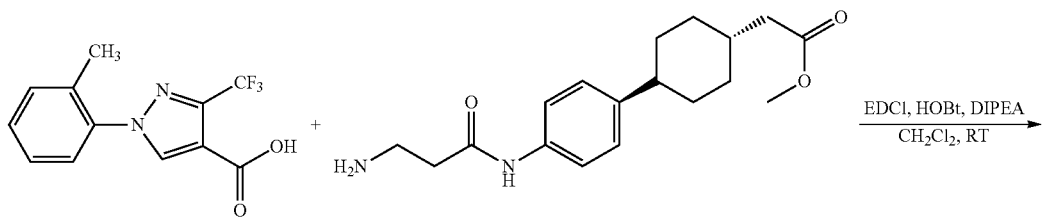

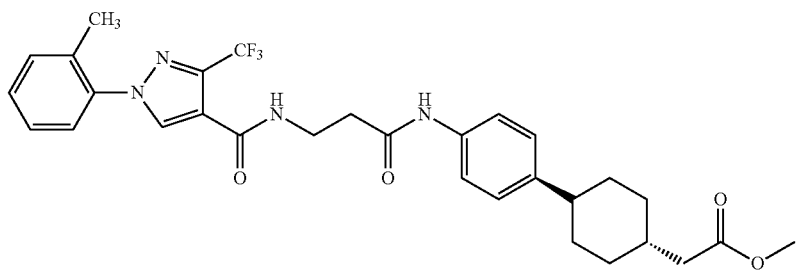

A mixture of trans-{4-[4-(3-aminopropionylamino)phenyl]cyclohexyl}acetic acid methyl ester (50 mg, 0.16 mmol), EDCI (75.26 mg, 0.39 mmol), 1-o-tolyl-3-trifluoromethyl-1H-pyrazole-4-carboxylic acid (51 mg, 0.19 mmol), HOBt (31.8 mg, 0.24 mmol) and ethyldiisopropylamine (71.2 mg, 0.6 mmol) dissolved in dichloromethane solvent (10 mL) was stirred for 24 hours. The reaction mixture was diluted with aqueous NaHCO₃ and extracted with dichloromethane. The extract was washed with brine and dried with anhydrous sodium sulfate and concentrated under vacuum. The residue was purified with silica gel column chromatography to obtain the desired compound (82 mg, 91%) as a white solid.

Example 13

Preparation of trans-[4-(4-{3-[(1-o-tolyl-3-trifluoromethyl-1H-pyrazole-4-ylmethyl)amino]propionylamino}phenyl)cyclohexyl]acetic acid (Compound 45)

NaOH (52.6 mg, 1.3 mmol) was added to trans-[4-(4-{3-[(1-o-tolyl-3-trifluoromethyl-1H-pyrazole-4-carbonyl)amino]propionylamino}phenyl)cyclohexyl]acetic acid methyl ester (75 mg, 0.13 mmol) dissolved in THF/MeOH/water (20 mL, 3:2:1). The reaction mixture was stirred at 25° C. for 5 hours and concentrated under vacuum. The residue was acidified with 1M HCl up to pH of 2 and extracted with ethyl acetate. The extract was washed with brine and dried with anhydrous sodium sulfate and concentrated under vacuum. The residue was stirred with acetonitrile and filtered. The filtrate was eluted with a gradient of methanol/DCM (5-10%) on a silica gel by column chromatography and purified. Accordingly, the desired compound (70 mg, 96%) was obtained as a white solid.

$^1$H NMR (300 MHz, DMSO-$d_6$): δ 12.04 (s, 1H), 9.91 (s, 1H), 8.62 (s, 1H), 8.51-8.43 (m, 1H), 7.53-7.35 (m, 6H), 7.12 (d, J=8.5 Hz, 2H), 3.54-3.44 (m, 2H), 2.62-2.54 (m, 2H), 2.19 (s, 3H), 2.12 (d, J=6.6 Hz, 2H), 1.84-1.61 (m, 5H), 1.49-1.31 (m, 2H), 1.17-0.99 (m, 2H).

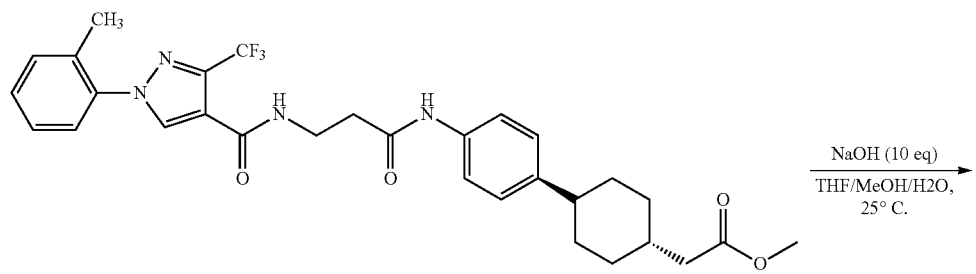

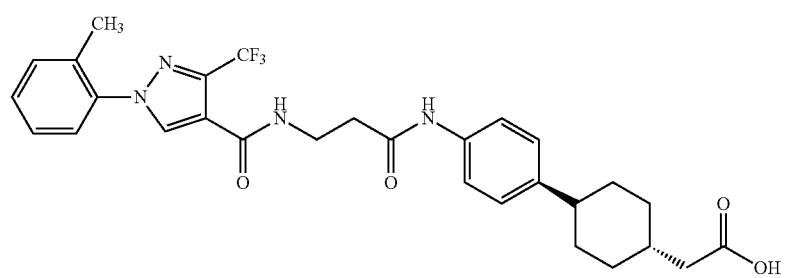

Example 14

Trans [4-(4-{3-[(5-chloro-1H-indole-2-carbonyl) amino]propionylamino}phenyl)cyclohexyl]acetic acid methyl ester (Compound 54)

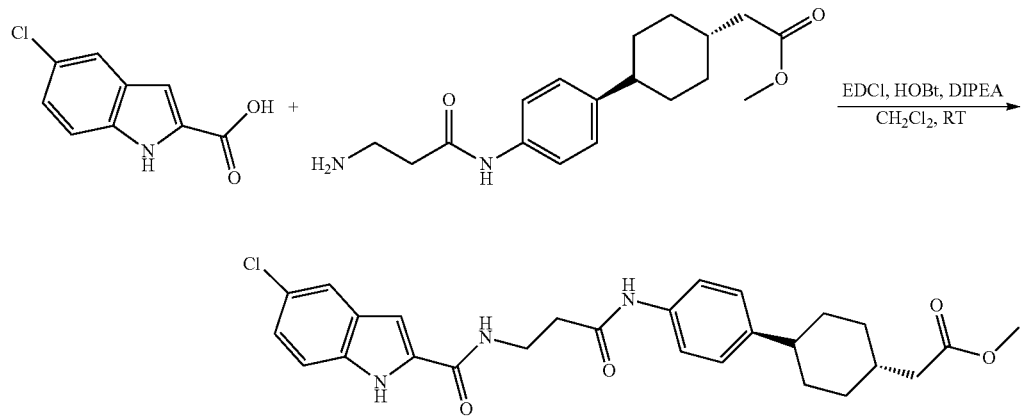

A mixture of trans-{4-[4-(3-aminopropionylamino)phenyl]cyclohexyl}acetic acid methyl ester (50 mg, 0.16 mmol), EDCI (75.26 mg, 0.39 mmol), 5-chloro-1H-indole-2-carboxylic acid (36.86 mg, 0.19 mmol), HOBt (31.8 mg, 0.24 mmol) and ethyldiisopropylamine (71.2 mg, 0.6 mmol) dissolved in dichloromethane solvent (10 mL) was stirred for 24 hours. The reaction mixture was diluted with aqueous NaHCO$_3$ and extracted with dichloromethane. The extract was washed with brine and dried with anhydrous sodium sulfate and concentrated under vacuum. The residue was purified with silica gel column chromatography to obtain the desired compound (75 mg, 96%) as a white solid.

Example 15

Trans [4-(4-{3-[(5-chloro-1H-indole-2-carbonyl) amino]propionylamino}phenyl)cyclohexyl]acetic acid (Compound 55)

NaOH (56.5 mg, 1.4 mmol) was added to trans-[4-(4-{3-[(5-chloro-1H-indole-2-carbonyl)amino] propionylamino}phenyl)cyclohexyl]acetic acid methyl ester (70 mg, 0.14 mmol) dissolved in THF/MeOH/water (20 mL, 3:2:1). The reaction mixture was stirred at 25° C. for 5 hours, concentrated under vacuum, and the residue was acidified with 1M HCl up to pH 2 and extracted with ethyl acetate. The extract was washed with brine and dried with anhydrous sodium sulfate and concentrated under vacuum. The residue was stirred with acetonitrile and filtered. The filtrate was eluted with a gradient of methanol/DCM (5-10%) on a silica gel by a column chromatography and purified to obtain the desired compound (64 mg, 94%) as a white solid.

$^1$H NMR (300 MHz, DMSO-d$_6$) δ (s, 1H), 11.78 (s, 1H), 9.90 (s, 1H), 8.72-8.65 (m, 1H), 7.69-7.66 (m, 1H), 7.48 (d, J=8.2 Hz, 2H), 7.41 (d, J=8.7 Hz, 1H), 7.19-7.05 (m, 4H), 3.62-3.50 (m, 2H), 2.66-2.55 (m, 2H), 2.45-2.31 (m, 1H), 2.12 (d, J=6.8 Hz, 2H), 1.85-1.61 (m, 5H), 1.50-1.32 (m, 2H), 1.17-0.99 (m, 2H).

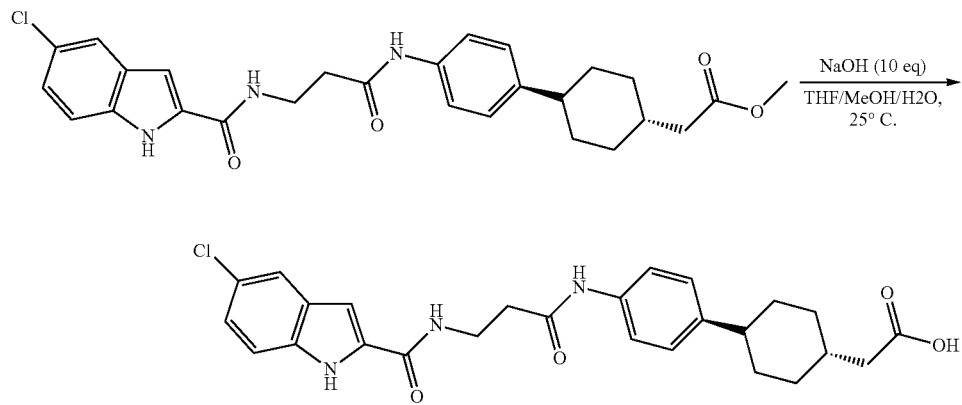

Example 16

Preparation of trans-{4-[4-(3-{[2-(4-fluorophenyl)-5-trifluoromethyloxazole-4-carbonyl]amino}propionylamino)phenyl]cyclohexyl}acetic acid (Compound 56)

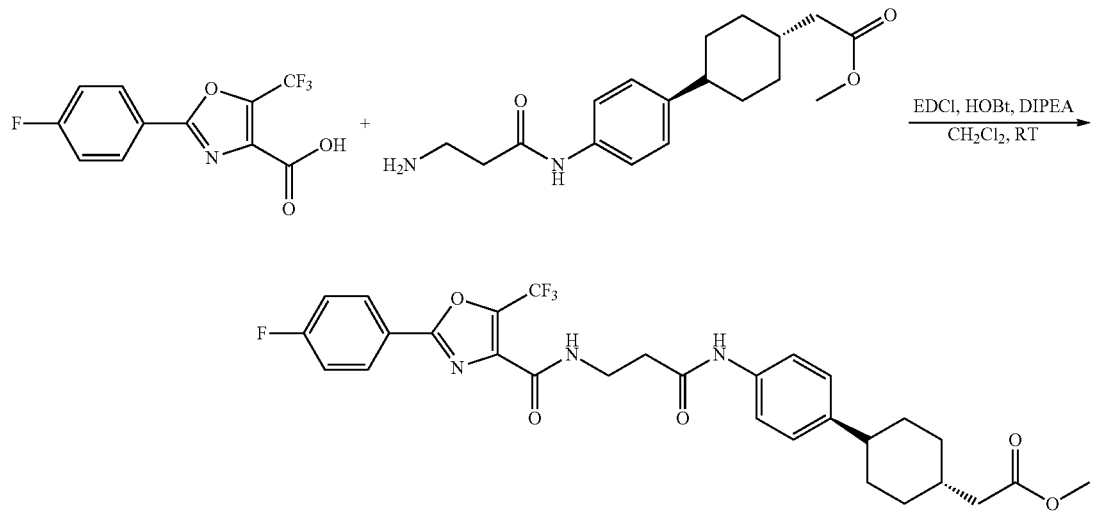

A mixture of trans-{4-[4-(3-aminopropionylamino)phenyl]cyclohexyl}acetic acid methyl ester (60 mg, 0.16 mmol), EDCI (90.3 mg, 0.47 mmol), 2-(4-fluorophenyl)-5-trifluoromethyloxazole-4-carboxylic acid (62.2 mg, 0.23 mmol), HOBt (38.2 mg, 0.28 mmol) and ethyldiisopropylamine (85.4 mg, 0.7 mmol) dissolved in dichloromethane solvent (10 mL) was stirred for 24 hours. The reaction mixture was diluted with aqueous NaHCO₃ and extracted with dichloromethane. The extract was washed with brine and dried with anhydrous sodium sulfate and concentrated under vacuum. The residue was purified by a silica gel column chromatography to obtain trans-{4-[4-(3-{[2-(4-fluorophenyl)-5-trifluoromethyloxazole-4-carbonyl]amino}propionylamino)phenyl]cyclohexyl}acetic acid methyl ester (89 mg, 82%) as a white solid.

NaOH (30.9 mg, 0.8 mmol) was added to trans-{4-[4-(3-{[2-(4-fluorophenyl)-5-trifluoromethyloxazole-4-carbonyl]amino}propionylamino)phenyl]cyclohexyl}acetic acid methyl ester solution (89 mg, 0.16 mmol) dissolved in THF/MeOH/water (20 mL, 3:2:1). The reaction mixture was stirred at 25° C. for 15 hours and concentrated under vacuum. The residue was acidified with 1M HCl up to pH 2, stirred for 30 minutes, and filtered. The filtrate was eluted with a gradient of methanol/DCM (5-10%) on a silica gel by column chromatography and purified to obtain the desired compound (75 mg, 86%) as a white solid.

$^1$H NMR (300 MHz, DMSO-$d_6$): δ 12.02 (s, 1H), 9.92 (s, 1H), 8.81-8.72 (m 1H), 8.16-8.07 (m, 2H), 7.53-7.42 (m, 4H), 7.13 (d, J=8.0 Hz, 2H), 3.61-3.51 (m, 2H), 2.67-2.58 (m, 2H), 2.45-2.31 (m, 1H), 2.13 (d, J=6.8 Hz, 2H), 1.85-1.62 (m, 5H), 1.49-1.32 (m, 2H), 1.18-1.00 (m, 2H).

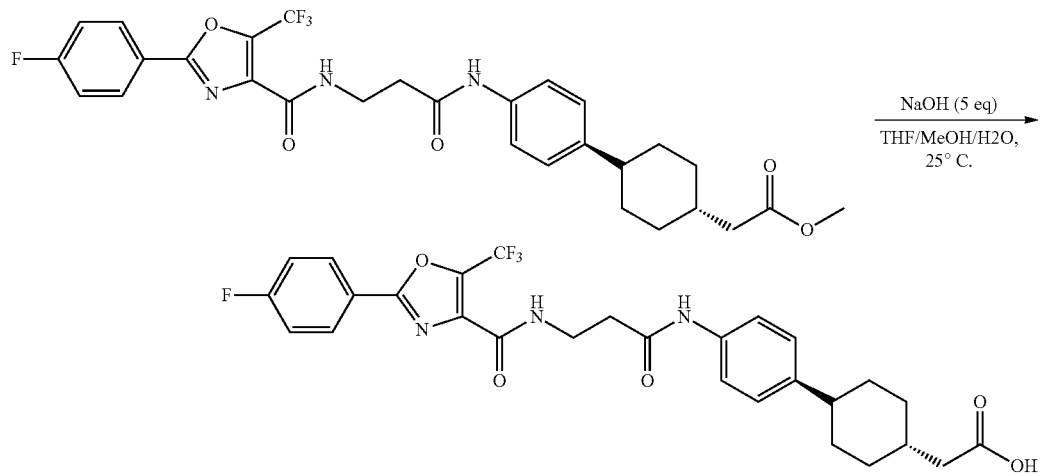

Example 17

Preparation of trans-{4-[4-(3-{[2-(2-fluorophenyl)-5-trifluoromethyloxazole-4-carbonyl]amino}propionylamino)phenyl]cyclohexyl}acetic acid methyl ester (Compound 59)

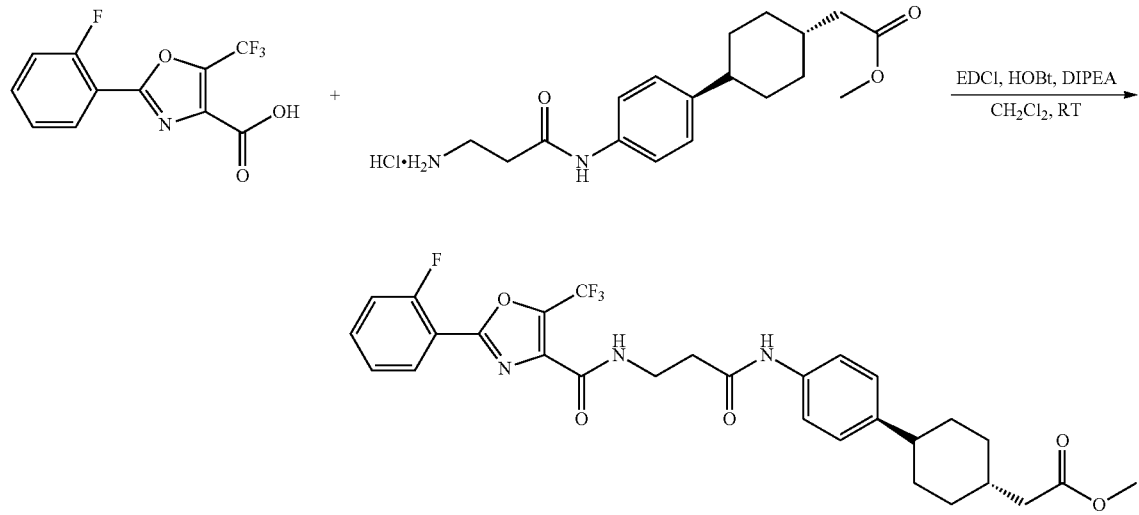

Trans-{4-[4-(3-aminopropionylamino)phenyl]cyclohexyl}acetic acid methyl ester HCl salt (50 mg, 0.14 mmol), EDCI (67.5 mg, 0.35 mmol), 2-(2-fluorophenyl)-5-trifluoromethyloxazole-4-carboxylic acid (46.5 mg, 0.17 mmol), HOBt (28.6 mg, 0.2 mmol) and ethyldiisopropylamine (63.9 mg, 0.5 mmol) dissolved in dichloromethane solvent (10 mL) were stirred for 24 hours. The reaction mixture was diluted with aqueous NaHCO₃ and extracted with dichloromethane. The extract was washed with brine and dried with anhydrous sodium sulfate and concentrated under vacuum. The residue was purified by a silica gel column chromatography to obtain trans-{4-[4-(3-{[2-(2-fluorophenyl)-5-trifluoromethyloxazole-4-carbonyl]amino}propionylamino)phenyl]cyclohexyl}acetic acid methyl ester (73 mg, 90%) as a white solid.

$^1$H NMR (300 MHz, CDCl$_3$): δ 8.06 (t, J=7.4H, 1H), 7.86-7.77 (m, 1H), 7.60-7.39 (m, 4H), 7.34-7.20 (m, 2H), 7.15 (d, J=8.0 Hz, 2H), 3.89-3.79 (m, 2H), 2.79-2.71 (m, 2H), 2.50-2.36 (m, 1H), 2.24 (d, J=6.4 Hz, 2H), 1.92-1.77 (m, 5H), 1.54-1.37 (m, 2H), 1.22-1.04 (m, 2H).

Example 18

Preparation of trans-{4-[4-(3-{[2-(2-fluorophenyl)-5-trifluoromethyloxazole-4-carbonyl]amino}propionylamino)phenyl]cyclohexyl}acetic acid (Compound 60)

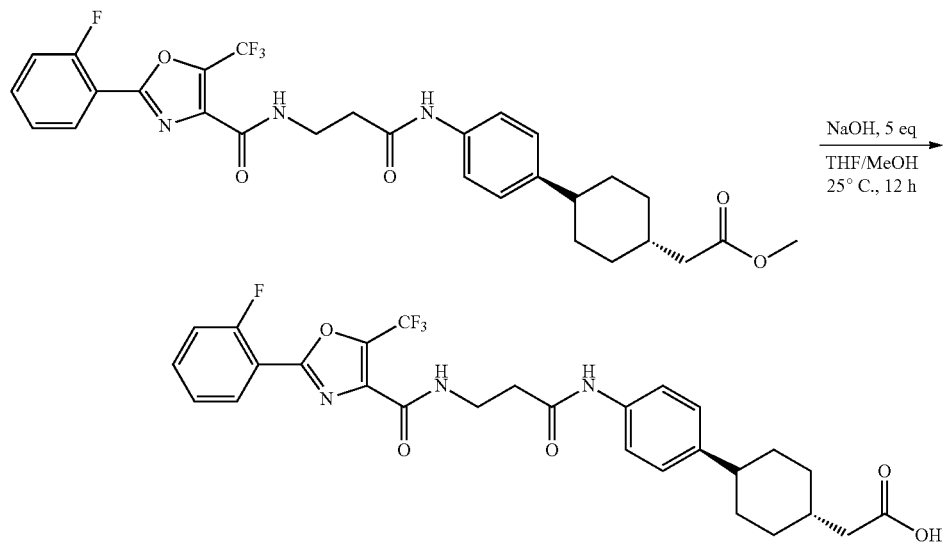

NaOH (22.6 mg, 0.57 mmol) was added to trans-{4-[4-(3-{[2-(2-fluoro-phenyl)-5-trifluoromethyloxazole-4-carbonyl]amino}propionylamino)phenyl]cyclohexyl}acetic acid methyl ester (65 mg, 0.11 mmol) dissolved in THF/MeOH/water (20 mL, 3:2:1). The reaction mixture was stirred at 25° C. for 15 hours and concentrated under vacuum. The residue was acidified with 1M HCl up to pH of 2, stirred for 30 minutes, and filtered. The filtrate was eluted with a gradient of methanol/DCM (5-10%) on a silica gel by column chromatography and purified to obtain the desired compound (60 mg, 94%) as a white solid.

$^1$H NMR (300 MHz, DMSO-d$_6$): δ 11.93 (s, 1H), 9.91 (s, 1H), 8.78-8.69 (m, 1H), 8.15-8.05 (m, 1H), 7.77-7.65 (m, 1H), 7.54-7.39 (m, 4H), 7.13 (d, J=7.6 Hz, 2H), 3.62-3.49 (m, 2H), 2.65-2.57 (m, 2H), 2.45-2.31 (m, 1H), 2.12 (d, J=6.8 Hz, 2H), 1.85-1.61 (m, 5H), 1.50-1.32 (m, 2H), 1.16-0.99 (m, 2H).

Example 19

Preparation of trans-{4-[4-(3-{[2-(2,4-dichlorophenyl)-5-trifluoromethyloxazole-4-carbonyl]amino}propionylamino)phenyl]cyclohexyl}acetic acid methyl ester (Compound 63)

mmol), EDCI (81 mg, 0.42 mmol), 2-(2,4-dichloro-phenyl)-5-trifluoromethyl-oxazole-4-carboxylic acid (66.14 mg, 0.2 mmol), HOBt (34.27 mg, 0.25 mmol) and ethyldiisopropylamine (76.7 mg, 0.6 mmol) dissolved in dichloromethane solvent (10 mL) were stirred for 24 hours. The reaction mixture was diluted with aqueous NaHCO$_3$ and extracted with dichloromethane. The extract was washed with brine and dried with anhydrous sodium sulfate and concentrated under vacuum. The residue was purified with silica gel column chromatography to obtain the desired compound (80 mg, 75%) as a white solid.

$^1$H NMR (300 MHz, CDCl$_3$): δ 8.01-7.95 (m, 1H), 7.86-7.78 (m, 1H), 7.57 (s, 1H), 7.49-7.36 (m, 4H), 7.14 (d, J=7.7 Hz, 2H), 3.87-3.78 (m, 2H), 3.68 (s, 3H), 2.78-2.70 (m, 2H), 2.49-2.36 (m, 1H), 2.25 (d, J=7.0 Hz, 2H), 1.92-1.78 (m, 5H), 1.54-1.37 (m, 2H), 1.22-1.05 (m, 2H).

Example 20

Preparation of trans-{4-[4-(3-{[2-(2,4-dichlorophenyl)-5-trifluoromethyloxazole-4-carbonyl]amino}propionylamino)phenyl]cyclohexyl}acetic acid (Compound 64)

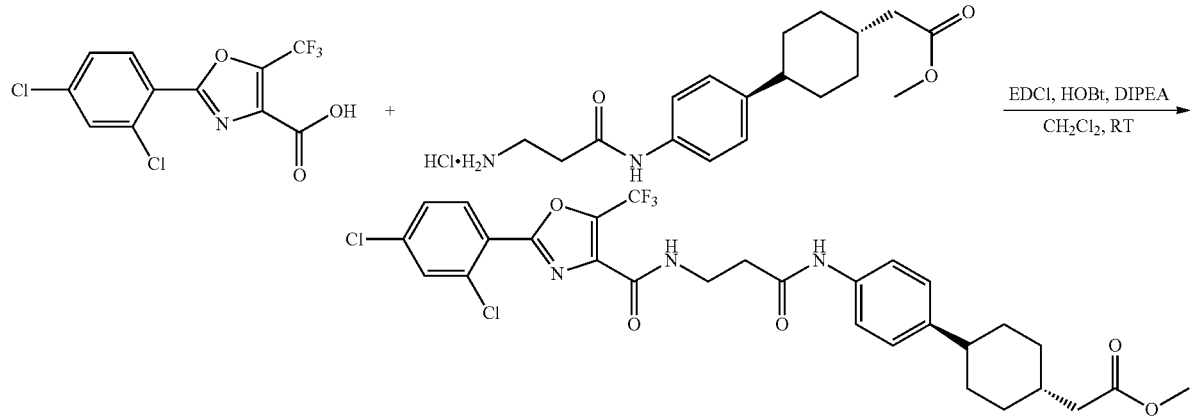

A mixture of trans-{4-[4-(3-aminopropionylamino)phenyl]cyclohexyl}acetic acid methyl ester HCl salt (60 mg, 0.17

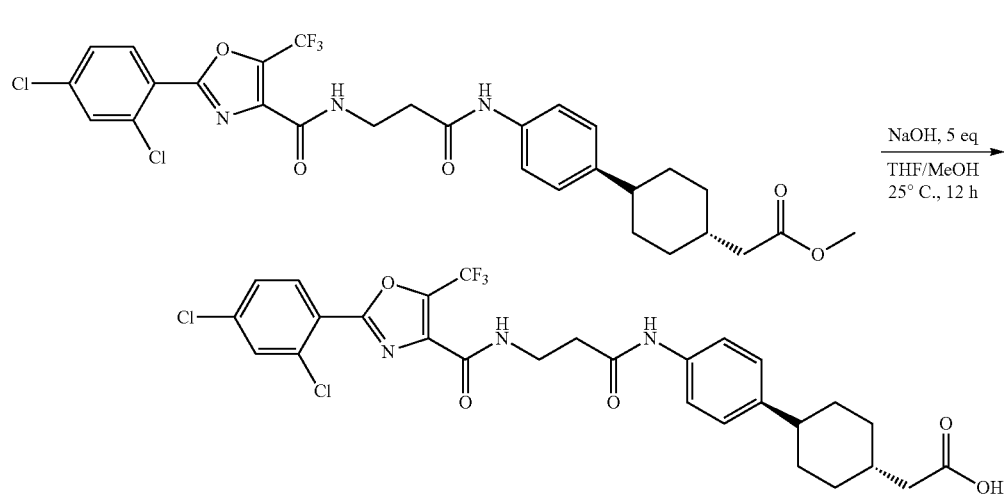

NaOH (23.94 mg, 0.56 mmol) was added to trans-{4-[4-(3-{[2-(2,4-dichlorophenyl)-5-trifluoromethyloxazole-4-carbonyl]amino}propionylamino)phenyl]cyclohexyl}acetic acid methyl ester (75 mg, 0.12 mmol) dissolved in THF/MeOH/water (20 mL, 3:2:1). The reaction mixture was stirred at 25° C. for 15 hours and concentrated under vacuum. The residue was acidified with 1M HCl up to pH 2, stirred for 30 minutes, and filtered. Then, the filtrate was eluted with a gradient of methanol/DCM (5-10%) on a silica gel by column chromatography and purified. Accordingly, the desired compound (71 mg, 97%) was obtained as a white solid.

$^1$H NMR (300 MHz, DMSO-$d_6$): δ 12.01 (s, 1H), 9.91 (s, 1H), 8.81-8.73 (m, 1H), 8.08 (d, J=8.6 Hz, 1H), 7.93 (d, J=2 Hz, 1H), 7.69 (dd, J=8.6, 2.0 Hz, 1H), 7.47 (d, J=8.6 Hz, 2H), 7.13 (d, J=8.4 Hz, 2H), 3.62-3.49 (m, 2H), 2.66-2.57 (m, 2H), 2.45-2.31 (m, 1H), 2.12 (d, J=6.7 Hz, 2H), 1.85-1.64 (m, 5H), 1.50-1.32 (m, 2H), 1.18-1.00 (m, 2H).

Example 21

Preparation of trans-{4-[4-(3-{[5-trifluoromethyl-2-(2-trifluoromethylphenyl)oxazole-4-carbonyl]amino}propionylamino)phenyl]cyclohexyl}acetic acid (Compound 66)

Step 1: Preparation of trans-{4-[4-(3-{[5-trifluoromethyl-2-(2-trifluoromethylphenyl)oxazole-4-carbonyl]amino}propionylamino)phenyl]cyclohexyl}acetic acid methyl ester Trans-{4-[4-(3-aminopropionylamino)phenyl]cyclohexyl}acetic acid methyl ester HCl salt (300 mg, 0.846 mmol), EDCI (405.23 mg, 2.114 mmol), 5-trifluoromethyl-2-(2-trifluoromethylphenyl)oxazole-4-carboxylic acid (288.68 mg, 0.888 mmol), HOBt (171.39 mg, 1.268 mmol) and ethyldiisopropylamine (383.39 mg, 2.959 mmol) were put into dichloromethane solvent (10 mL) and stirred at room temperature for 24 hours. After the reaction, aqueous NaHCO$_3$ was added thereto, and extracted with dichloromethane. The organic layer was washed with brine, then the product was dried with anhydrous sodium sulfate, and the solvent was removed. Column chromatography was conducted on the crude material to obtain trans-{4-[4-(3-{[5-trifluoromethyl-2-(2-trifluoromethylphenyl)oxazole-4-carbonyl]amino}propionylamino)phenyl]cyclohexyl}acetic acid methyl ester (461 mg, 87%).

Step 2: Preparation of trans-{4-[4-(3-{[5-trifluoromethyl-2-(2-trifluoromethylphenyl)oxazole-4-carbonyl]amino}propionylamino)phenyl]cyclohexyl}acetic acid

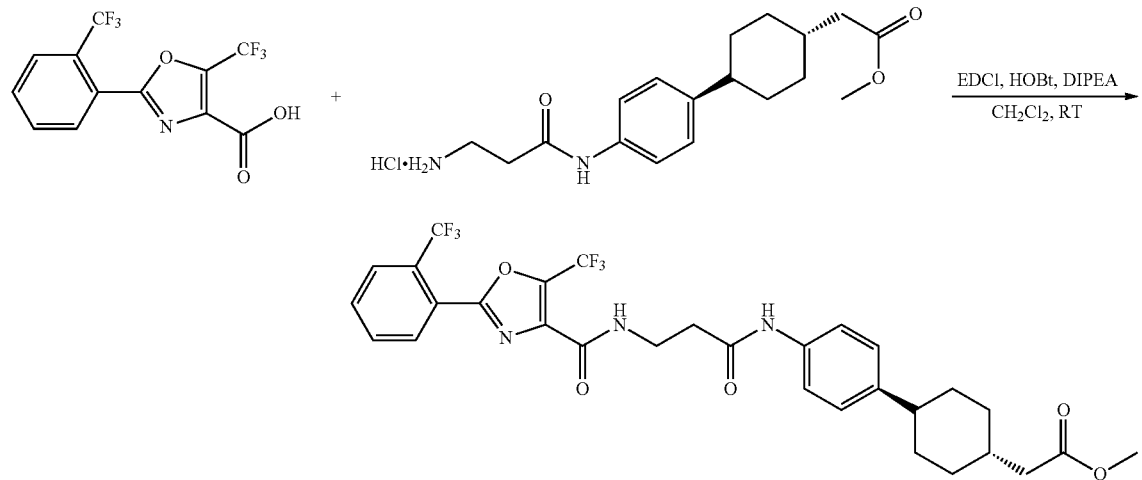

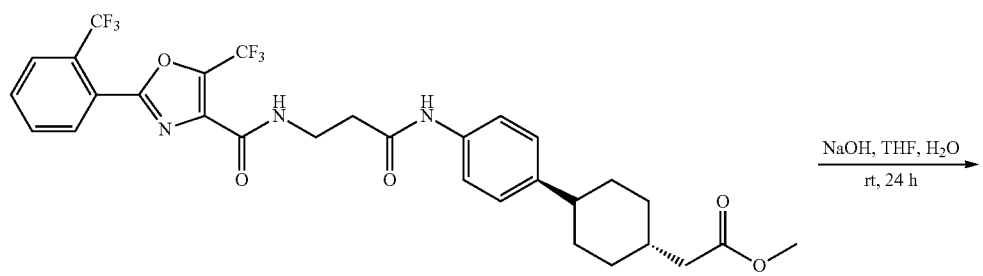

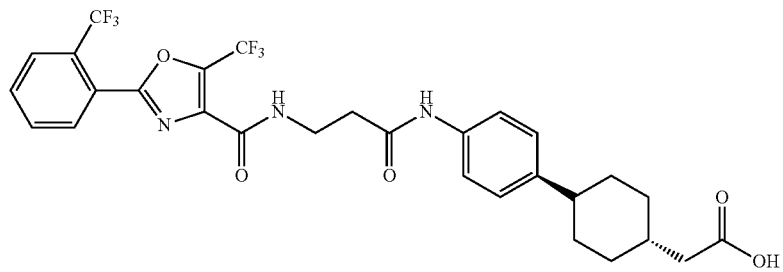

Trans-{4-[4-(3-{[5-trifluoromethyl-2-(2-trifluoromethylphenyl)oxazole-4-carbonyl]amino}propionylamino)phenyl]cyclohexyl}acetic acid methyl ester (455 mg, 0.727 mmol) was put into THF/water (50 mL, 3:1) solvent, and NaOH (145.47 mg, 3.637 mmol) was added thereto. The mixture was stirred at room temperature for 24 hours, THF was removed, and pH of the mixture was adjusted to be 2-3 with 1N hydrochloric acid. The reaction mixture was extracted with EtOAC (3×100 mL), washed with brine and dried with anhydrous sodium sulfate, and the solvent was removed. The obtained crude material was crystallized with acetonitrile to obtain the desired compound (435 mg, 98%) as a white solid.

Example 22

Preparation of trans-{4-[4-(3-{[2-(2,6-dichlorophenyl)-5-trifluoromethyloxazole-4-carbonyl]amino}propionylamino)phenyl]cyclohexyl}acetic acid (Compound 68)

Step 1: Preparation of trans-{4-[4-(3-{[2-(2,6-dichlorophenyl)-5-trifluoromethyloxazole-4-carbonyl]amino}propionylamino)phenyl]cyclohexyl}acetic acid methyl ester Trans-{4-[4-(3-aminopropionylamino)phenyl]cyclohexyl}acetic acid methyl ester HCl salt (380 mg, 1.071 mmol), EDCI (513.3 mg, 2.678 mmol), 2-(2,6-dichlorophenyl)-5-trifluoromethyloxazole-4-carboxylic acid (366.61 mg, 1.125 mmol), HOBt (217.09 mg, 1.607 mmol) and ethyldiisopropylamine (485.63 mg, 3.749 mmol) were put into dichloromethane solvent (10 mL) and stirred at room temperature for 24 hours. After the reaction, aqueous NaHCO$_3$ was added thereto, and extracted with dichloromethane. The organic layer was washed with brine, then the product was dried with anhydrous sodium sulfate, and solvent was removed. Column chromatography was conducted on the crude material to obtain trans-{4-[4-(3-{[2-(2,6-dichlorophenyl)-5-trifluoromethyloxazole-4-carbonyl]amino}propionylamino)phenyl]cyclohexyl}acetic acid methyl ester (609 mg, 91%).

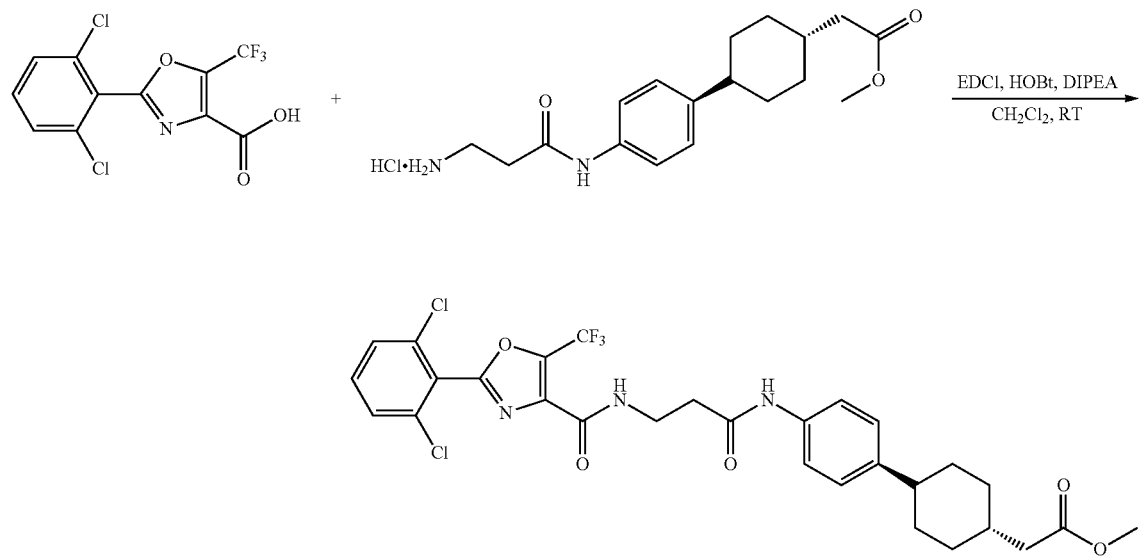

Step 2: Preparation of trans-{4-[4-(3-{[2-(2,6-dichlorophenyl)-5-trifluoromethyloxazole-4-carbonyl]amino}propionylamino)phenyl]cyclohexyl}acetic acid

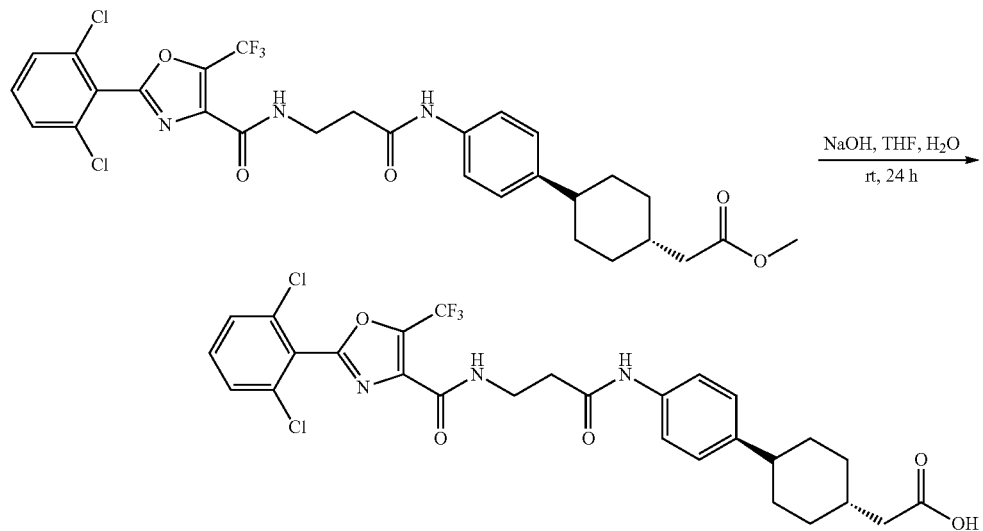

Trans-{4-[4-(3-{[2-(2,6-dichloro-phenyl)-5-trifluoromethyloxazole-4-carbonyl]amino}propionylamino)phenyl]cyclohexyl}acetic acid methyl ester (459 mg, 0.733 mmol) was put into THF/water (50 mL, 3:1) solvent, and NaOH (146.54 mg, 3.663 mmol) was added thereto. The mixture was stirred for 24 hours, THF was removed, and pH of the mixture was adjusted to be 2-3 with 1N hydrochloric acid. The reaction mixture was extracted with EtOAC (3×100 mL), washed with brine and dried with anhydrous sodium sulfate, and the solvent was removed. The obtained crude material was crystallized with acetonitrile to obtain the desired compound (434 mg, 97%) as a white solid.

Example 23

Preparation of trans-{4-[4-(3-{[2-(2,6-dichlorophenyl)-5-trifluoromethyloxazole-4-carbonyl]amino}propionylamino)phenyl]cyclohexyl}acetate sodium salt (Compound 69)

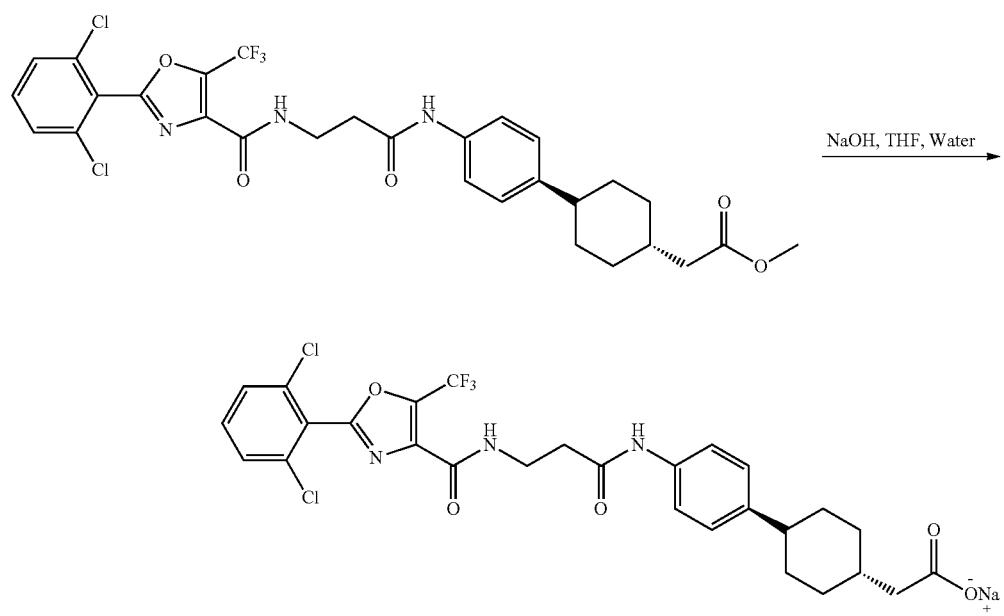

Trans-{4-[4-(3-{[2-(2,6-dichlorophenyl)-5-trifluoromethyloxazole-4-carbonyl]amino}propionylamino)phenyl]cyclohexyl}acetate methyl ester (150 mg, 0.239 mmol) was put into THF/water (20 mL, 3:1) solvent, then NaOH (14.37 mg, 1.437 mmol) was added thereto and stirred at room temperature for 24 hours. After THF was removed, a desired sodium salt solid was washed with water to obtain a final compound (150 mg, 98%).

Example 24

Preparation of trans-{4-[4-(3-{[2-(2-chlorophenyl)-5-methyloxazole-4-carbonyl]amino}propionylamino)phenyl]cyclohexyl}acetic acid (Compound 70)

Step 1: Preparation of trans-{4-[4-(3-{[2-(2-chlorophenyl)-5-methyloxazole-4-carbonyl]amino}propionylamino)phenyl]cyclohexyl}acetic acid methyl ester Trans-{4-[4-(3-aminopropionylamino)-phenyl]cyclohexyl}acetic acid methyl ester HCl salt (60 mg, 0.169 mmol), EDCI (81.05 mg, 0.423 mmol), 2-(2-chloro-phenyl)-5-methyl-oxazole-4-carboxylic acid (44.2 mg, 0.186 mmol), HOBt (34.28 mg, 0.254 mmol) and ethyldiisopropylamine (76.68 mg, 0.592 mmol) were put into dichloromethane solvent (10 mL) and stirred at room temperature for 24 hours. After the reaction, aqueous NaHCO₃ was added thereto, and extracted with dichloromethane. The organic layer was washed with brine, then the product was dried with anhydrous sodium sulfate, and the solvent was removed. Column chromatography was conducted on the crude material to obtain trans-{4-[4-(3-{[2-(2-chlorophenyl)-5-methyloxazole-4-carbonyl]amino}propionylamino)phenyl]cyclohexyl}acetic acid methyl ester (80 mg, 88%).

Step 2: Preparation of trans-{4-[4-(3-{[2-(2-chlorophenyl)-5-methyloxazole-4-carbonyl]amino}propionylamino)phenyl]cyclohexyl}acetic acid

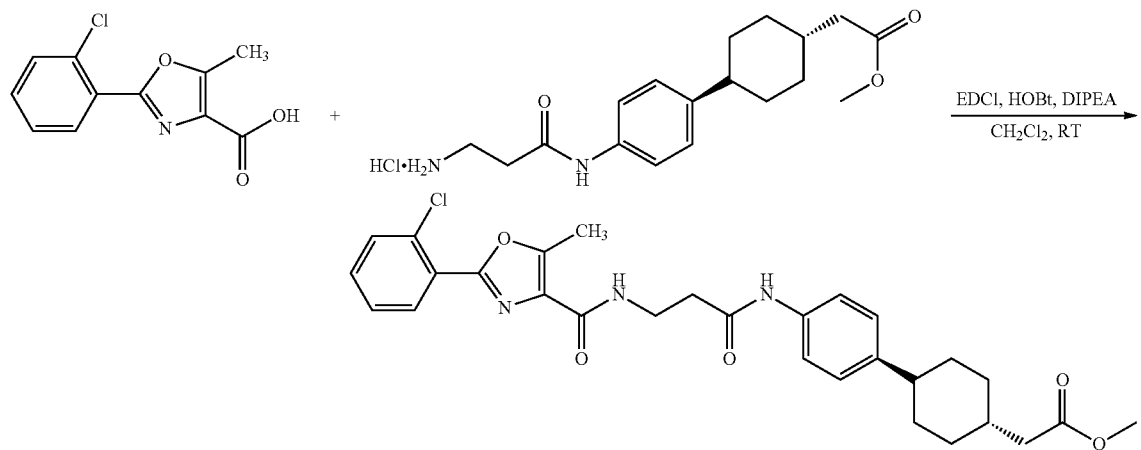

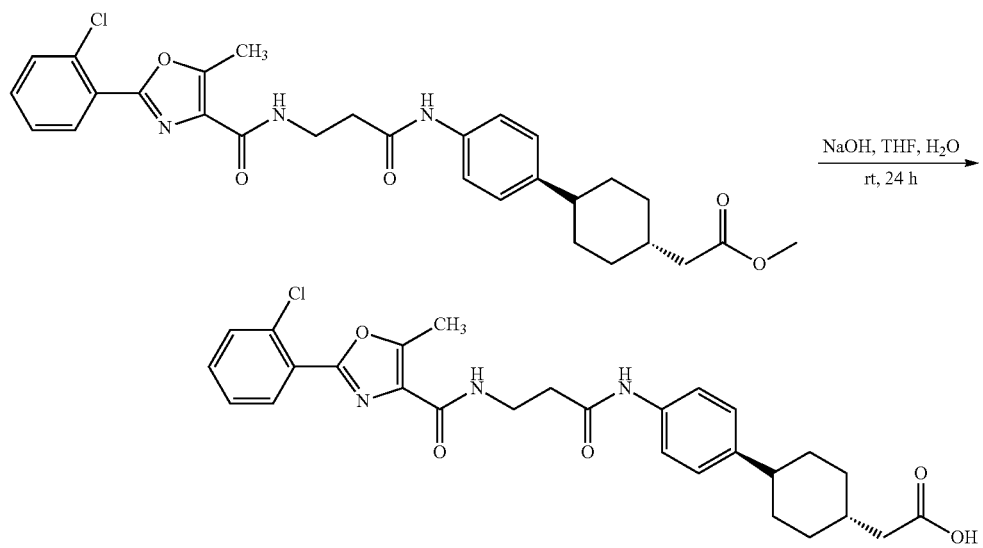

Trans-{4-[4-(3-{[2-(2-chlorophenyl)-5-methyloxazole-4-carbonyl]amino}propionylamino)phenyl]cyclohexyl}acetic acid methyl ester (80 mg, 0.149 mmol) was put into THF/water (20 mL, 3:1) solvent, and NaOH (44.61 mg, 1.115 mmol) was added thereto. The mixture was stirred for 24 hours, THF was removed, and pH of the mixture was adjusted to be 2-3 with 1N hydrochloric acid. The reaction mixture was extracted with EtOAC (3×100 mL), washed with brine and dried with anhydrous sodium sulfate, and the solvent was removed. The obtained crude material was crystallized with acetonitrile to obtain a compound (77 mg, 98%) as a white solid.

Example 25

Trans-[4-(4-{3-[(biphenyl-4-carbonyl)amino]propionylamino}phenyl)cyclohexyl]acetic acid (Compound 78)

Step 1: Preparation of trans-[4-(4-{3-[(biphenyl-4-carbonyl)amino]propionylamino}phenyl)cyclohexyl]acetic acid methyl ester mmol), EDCI (67.54 mg, 0.352 mmol), biphenyl-4-carboxylic acid (30.73 mg, 0.155 mmol), HOBt (28.56 mg, 0.211 mmol) and ethyldiisopropylamine (63.90 mg, 0.493 mmol) were put into dichloromethane solvent (10 mL) and stirred at room temperature for 24 hours. After the reaction, aqueous NaHCO$_3$ was added thereto, and extracted with dichloromethane. The organic layer was washed with brine, then the product was dried with anhydrous sodium sulfate, and the solvent was removed. A column chromatography was conducted on the crude material to obtain trans-[4-(4-{3-[(biphenyl-4-carbonyl)-amino]-propionylamino}-phenyl)-cyclohexyl]-acetic acid methyl ester (64 mg, 91%).

Step 2: Preparation of trans-[4-(4-{3-[(biphenyl-4-carbonyl)amino]propionylamino}phenyl)cyclohexyl] acetic acid

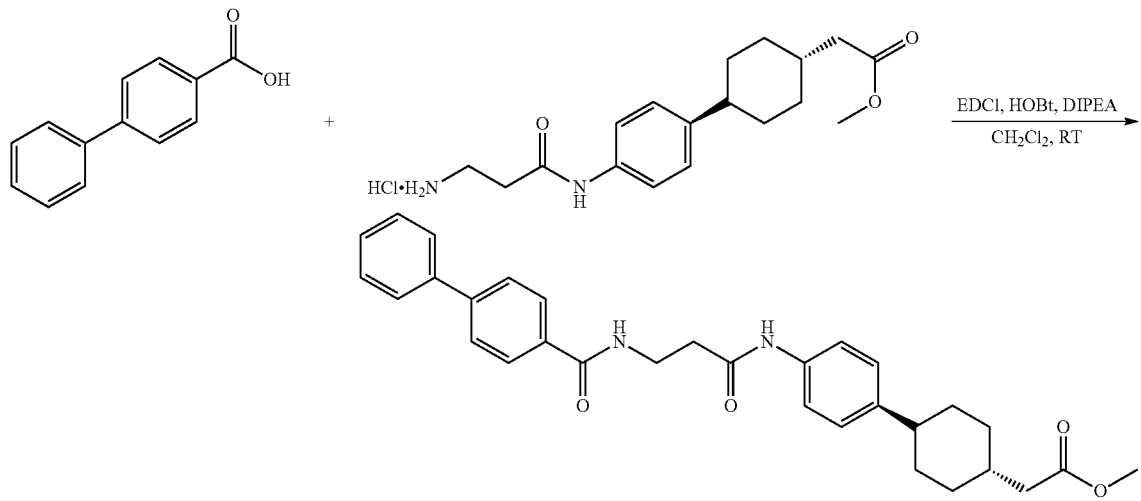

Trans-{4-[4-(3-aminopropionylamino)phenyl]cyclohexyl}acetic acid methyl ester HCl salt (50 mg, 0.141

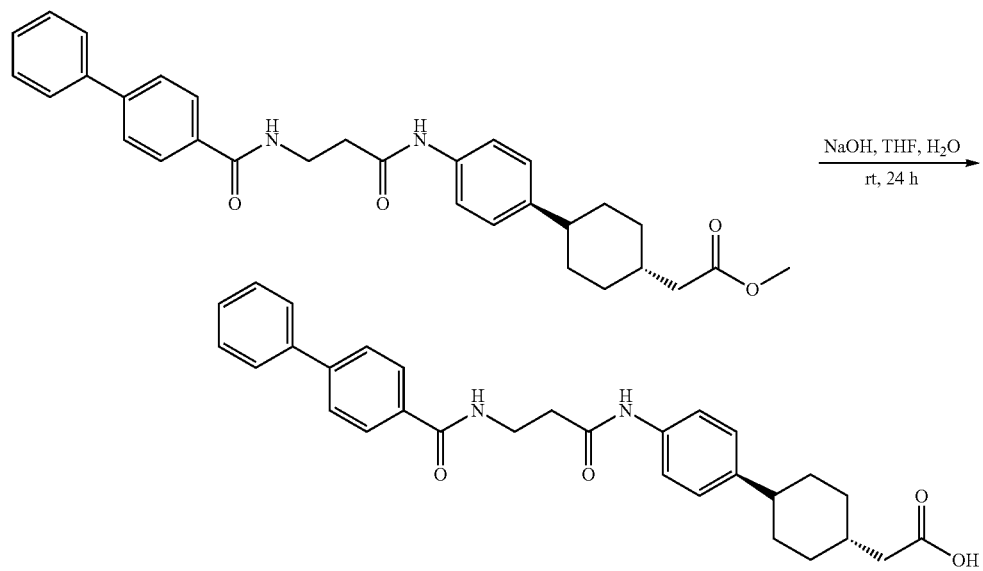

Trans-[4-(4-{3-[(biphenyl-4-carbonyl)amino]propionylamino}phenyl)cyclohexyl]acetic acid methyl ester (60 mg, 0.120 mmol) was put into THF/water (20 mL, 3:1) solvent, and NaOH (38.51 mg, 0.963 mmol) was added thereto. The mixture was stirred for 24 hours, THF was removed, and pH of the mixture was adjusted to be 2-3 with 1N hydrochloric acid. The reaction mixture was extracted with EtOAC (3×100 mL), washed with brine and dried with anhydrous sodium sulfate, and the solvent was removed. The obtained crude material was crystallized with acetonitrile to obtain the desired compound (56 mg, 96%) as a white solid.

Example 26

Preparation of trans-{4-[4-(3-{[2-(2-chlorophenyl)-5-trifluoromethyloxazole-4-carbonyl]amino}propionylamino)phenyl]cyclohexyl}acetate sodium salt (Compound 79)

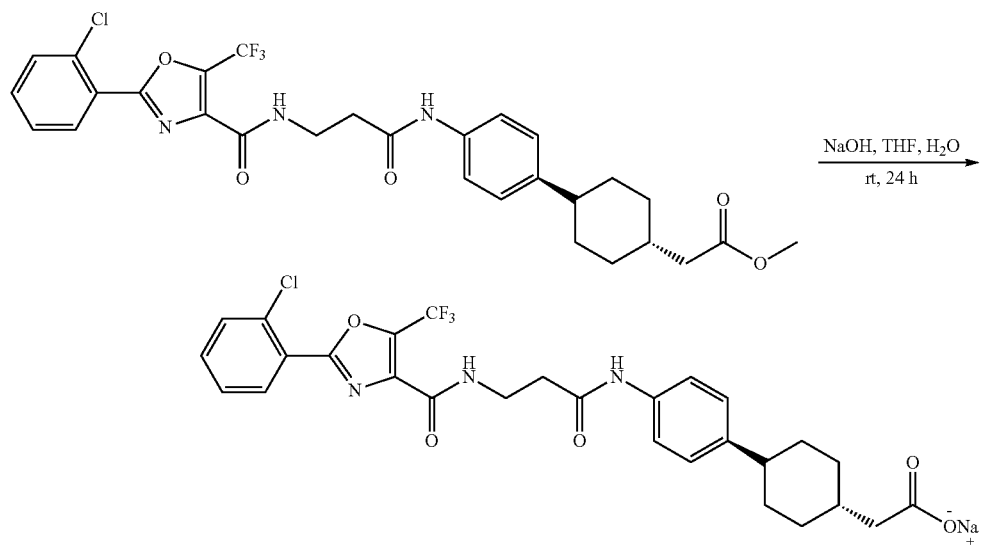

Trans-{4-[4-(3-{[2-(2-dichlorophenyl)-5-trifluoromethyloxazole-4-carbonyl]amino}propionylamino)phenyl]cyclohexyl}acetic acid methyl ester (226 mg, 0.382 mmol) was put into THF/water (20 mL, 3:1) solvent, then NaOH (73.30 mg, 1.832 mmol) was added thereto and stirred at room temperature for 24 hours. After THF was removed, a desired sodium salt solid was washed with water to obtain a final compound (225 mg, 98%). Chemical structures and NMR (or LC/MS data) values of specific compounds manufactured by Examples above are shown as follows.

No. 1

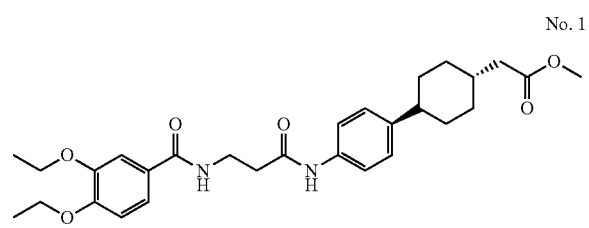

$^1$H NMR (300 MHz, CDCl$_3$): δ 7.72 (s, 1H), 7.46-7.34 (m, 3H), 7.24 (s, 1H), 7.14 (d, J=8.2 Hz, 2H), 7.01-6.93 (m, 1H), 6.82 (d, J=8.4 Hz, 1H), 4.18-4.04 (m, 4H), 3.84-3.74 (m, 2H), 3.68 (s, 3H), 2.74-2.65 (m, 2H), 2.50-2.36 (m, 1H), 2.25 (d, J=6.6 Hz, 2H), 1.93-1.77 (m, 5H), 1.54-1.36 (m, 8H), 1.22-1.05 (m, 2H).

No. 2

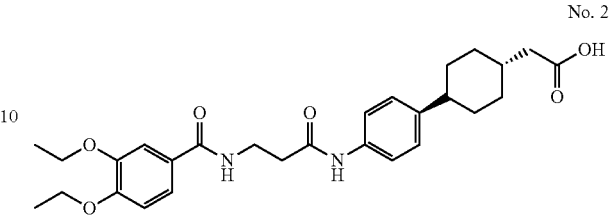

$^1$H NMR (300 MHz, DMSO-d$_6$): δ9.8 (s, 1H), 8.47-8.37 (m, 1H), 7.52-7.37 (m, 4H), 7.12 (d, J=8.5 Hz, 2H), 6.98 (d, J=8.6 Hz, 1H), 4.10-3.98 (m, 4H), 3.53-3.45 (m, 2H), 2.62-2.52 (m, 2H), 2.44-2.29 (m, 1H), 2.12 (d, J=6.4 Hz, 2H), 1.85-1.64 (m, 5H), 1.45-1.27 (m, 8H), 1.17-1.01 (m, 2H).

No. 3

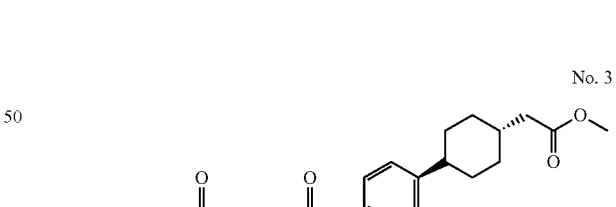

$^1$H NMR (300 MHz, CDCl$_3$): δ 7.76-7.65 (m, 3H), 7.42 (d, J=8.0 Hz, 2H), 7.25 (s, 1H), 7.15 (d, J=8.4 Hz, 2H), 7.01 6.93 (m, 1H), 6.88 (d, J=8.4 Hz, 2H), 4.05 (q, J=7.0 Hz, 2H), 3.85-3.75 (m, 2H), 3.68 (s, 3H), 2.74-2.65 (m, 2H), 2.49-2.36 (m, 1H), 2.25 (d, J=6.5 Hz, 2H), 1.94-1.77 (m, 5H), 1.5-1.36 (m, 5H), 1.22-1.05 (m, 1H).

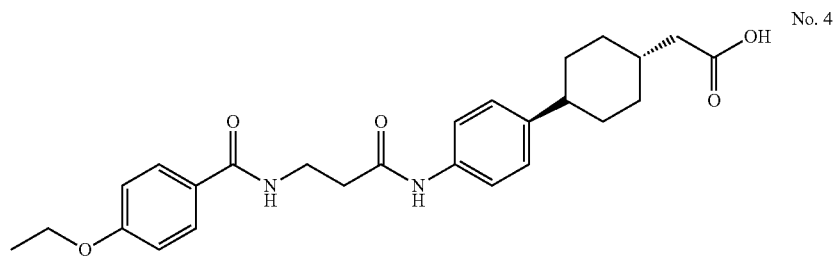
No. 4
$^1$H NMR (300 MHz, DMSO-d$_6$): δ 11.7 (s, 1H), 9.86 (s, 1H), 8.47-8.36 (m, 1H), 7.79 (d, J=8.6 Hz, 2H), 7.48 (d, J=8.2 Hz, 2H), 7.12 (d, J=8.2 Hz, 2H), 6.95 (d, J=8.5 Hz, 2H), 4.06 (q, J=7.0 Hz, 2H), 3.56-3.46 (m, 2H), 2.61-2.53 (m, 2H), 2.43-2.31 (m, 1H), 2.12 (d, J=7.0 Hz, 2H), 1.85-1.64 (m, 5H), 1.49-1.37 (m, 2H), 1.32 (t, J=7.0 Hz, 2H), 1.17-1.00 (m, 2H).
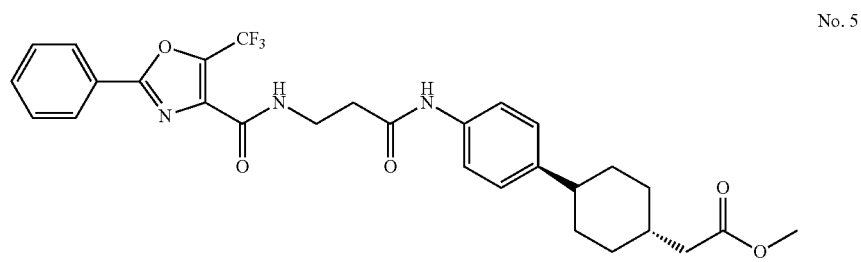
No. 5
$^1$H NMR (300 MHz, CDCl$_3$): δ 8.07 (d, J=6, 7 Hz, 2H), 7.88-7.79 (m, 1H), 7.62-7.47 (m, 4H), 7.43 (d, J=8.3 Hz, 2H), 7.15 (d, J=8.2 Hz, 2H), 3.88-3.78 (m, 2H), 3.68 (s, 3H), 2.75 (t, J=5.6 Hz, 2H), 2.48-2.36 (m, 1H), 2.24 (d, J=6.5 Hz, 2H), 1.93-1.78 (m, 5H), 1.56-1.37 (m, 2H), 1.22-1.04 (m, 2H).
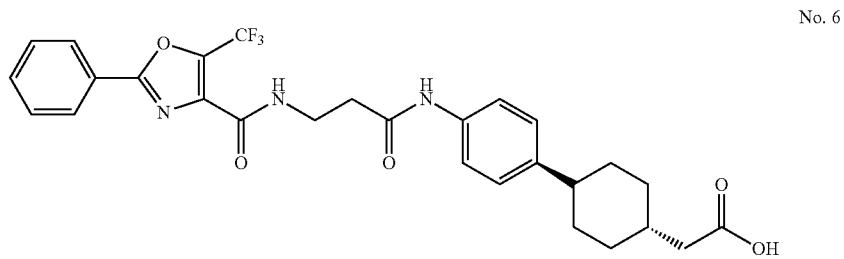
No. 6

$^1$H NMR (500 MHz, DMSO-d$_6$): δ11.99 (s, 1H), 9.91 (s, 1H), 8.76 (t, J=5.4 Hz, 1H), 8.08-8.04 (m, 2H), 7.69-7.59 (m, 3H), 7.48 (d, J=8.7 Hz, 2H), 7.13 (d, J=8.7 Hz, 2H), 3.56 (q, J=6.7 Hz, 2H), 2.63 (t, J=6.9 Hz, 2H), 2.43-2.35 (m, 1H), 2.13 (d, J=7.0 Hz, 2H), 1.83-1.65 (m, 5H), 1.47-1.36 (m, 2H), 1.15-1.03 (m, 2H).
No. 7
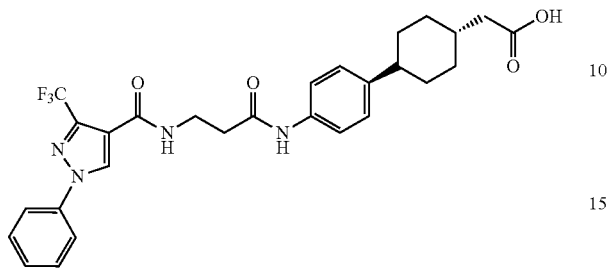
$^1$H NMR (500 MHz, DMSO-d$_6$): δ12.02 (s, 1H), 9.91 (s, 1H), 9.07 (s, 1H), 8.50-8.44 (m, 1H), 7.80 (d, J=7.7 Hz, 2H), 7.61-7.56 (m, 2H), 7.51-7.43 (m, 3H), 7.13 (d, J=8.5 Hz, 2H), 3.53-3.48 (m, 2H), 2.59 (t, J=6.8 Hz, 2H), 2.41-2.34 (m, 1H), 2.11 (d, J=6.8 Hz, 2H), 1.83-1.66 (m, 5H), 1.45-1.35 (m, 2H), 1.13-1.03 (m, 2H).
No. 8
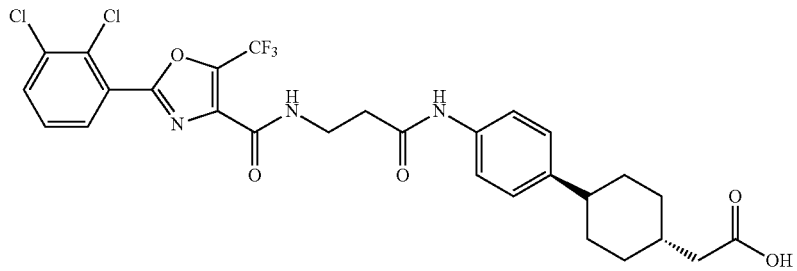
LC-MS (m/z): 612 (MH$^+$)
$^1$H NMR (300 MHz, DMSO-d$_6$) δ: 12.05 (s, 1H), 9.91 (s, 1H), 8.79 (t, J=5.76 Hz, 1H), 8.02 (d, J=8.33 Hz, 1H), 7.95 (d, J=8.33 Hz, 1H), 7.60 (t, J=8.11 Hz, 1H), 7.48 (d, J=8.54 Hz, 2H), 7.13 (d, J=8.29 Hz, 2H), 3.62-3.51 (m, 2H), 2.62 (t, J=6.75 Hz, 2H), 2.44-2.31 (m, 1H), 2.12 (d, J=7.29 Hz, 2H), 1.85-1.65 (m, 5H), 1.50-1.32 (m, 2H), 1.18-1.00 (m, 2H).
No. 9
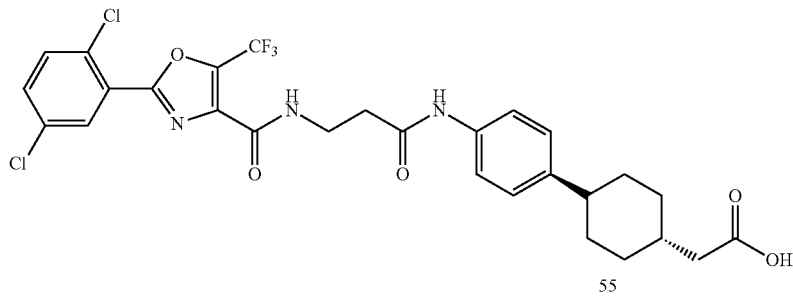
LC-MS (m/z): 612 (MH$^+$)
No. 10
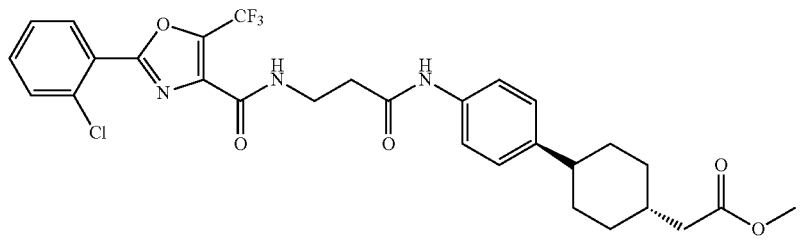

¹H NMR (300 MHz, CDCl₃): δ 8.02 (d, J=7.2 Hz, 1H), 7.88-7.78 (m, 1H), 7.59-7.36 (m, 6H), 7.14 (d, J=8.2 Hz, 2H), 3.89-3.78 (m, 2H), 3.68 (s, 3H), 2.74 (t, J=5.5 Hz, 2H), 2.49-2.34 (m, 1H), 2.24 (d, J=6.5 Hz, 2H), 1.93-1.79 (m, 5H), 1.56-1.37 (m, 2H), 1.22-1.04 (m, 2H).
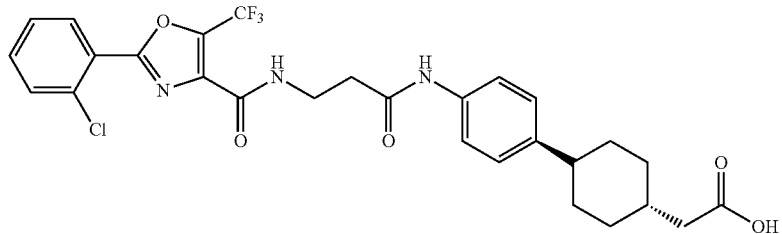
No. 11
¹H NMR (500 MHz, DMSO-d₆): δ12.03 (s, 1H), 9.92 (s, 1H), 8.80-8.74 (m, 1H), 8.06 (d, J=7.5 Hz, 1H), 7.72 (d, J=7.9 Hz, 1H), 7.66 (t, J=7.5 Hz, 1H), 7.58 (t, J=7.6 Hz, 1H), 7.48 (d, J=8.3 Hz, 2H), 7.13 (d, J=8.3 Hz, 2H), 3.60-3.5.2 (m, 2H), 2.62 (t, J=6.9 Hz, 2H), 2.42-2.34 (m, 1H), 2.12 (d, J=6.8 Hz, 2H), 1.83-1.65 (m, 5H), 1.46-1.35 (m, 2H), 1.14-1.03 (m, 2H).
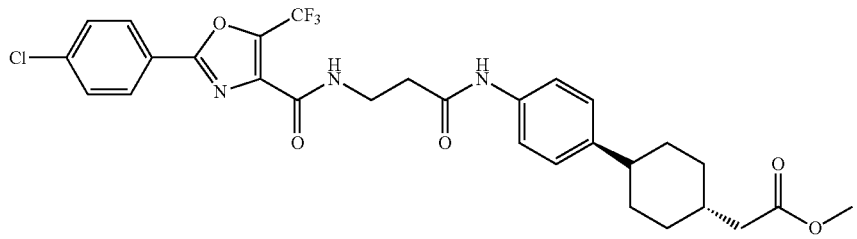
No. 12
¹H NMR (300 MHz, CDCl₃): δ 8.01 (d, J=7.5 Hz, 2H), 7.87-7.78 (m, 1H), 7.53-7.38 (m, 5H), 7.15 (d, J=7.5 Hz, 2H), 3.88-3.77 (m, 2H), 3.68 (s, 3H), 2.78-2.70 (m, 2H), 2.49-2.37 (m, 1H), 2.25 (d, J=6.7 Hz, 2H), 1.92-1.75 (m, 5H), 1.55-1.37 (m, 2H), 1.22-1.04 (m, 2H).
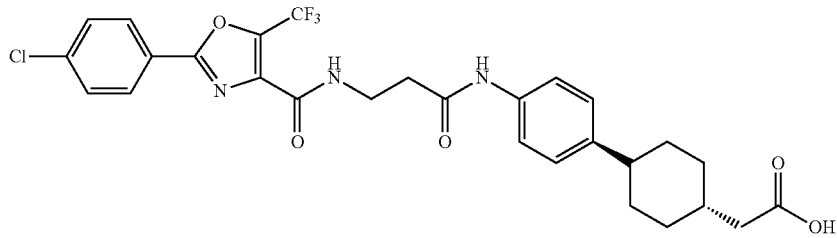
No. 13
¹H NMR (300 MHz, DMSO-d₆): δ11.91 (s, 1H), 9.92 (s, 1H), 8.82-8.74 (m, 1H), 8.06 (d, J=8.6 Hz, 2H), 7.69 (d, J=8.6 Hz, 2H), 7.48 (d, J=8.6 Hz, 2H), 7.13 (d, J=8.3 Hz, 2H), 3.61-3.50 (m, 2H), 2.67-2.57 (m, 2H), 2.44-2.31 (m, 1H), 2.12 (d, J=6.9 Hz, 2H), 1.84-1.62 (m, 5H), 1.49-1.32 (m, 2H), 1.18-0.99 (m, 2H).

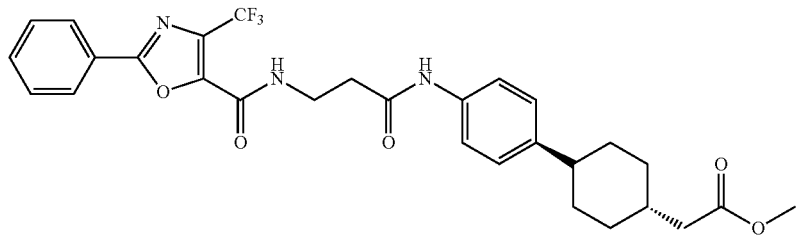
No. 14
¹H NMR (300 MHz, CDCl₃): δ 8.1 (d, J=6.9 Hz, 2H), 7.60-7.35 (m, 7H), 7.16 (d, J=8.5 Hz, 2H), 3.90-3.80 (m, 2H), 3.90-3.80 (m, 2H), 3.68 (s, 3H), 2.80-2.71 (m, 2H), 2.49-2.36 (m, 1H), 2.24 (d, J=6.4 Hz, 2H), 1.94-1.79 (m, 5H), 1.55-1.35 (m, 2H), 1.22-1.05 (m, 2H).
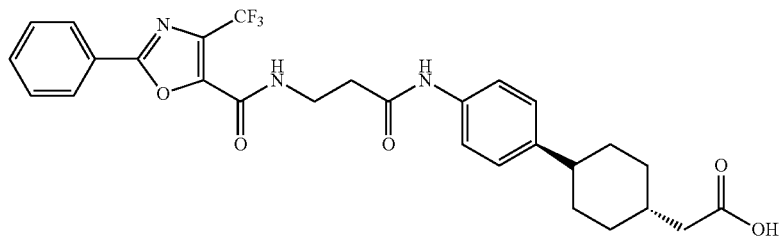
No. 15
¹H NMR (500 MHz, DMSO-d₆): δ12.03 (s, 1H), 9.94 (s, 1H), 9.28-9.17 (m, 1H), 8.17 (d, J=6.9 Hz, 2H), 7.69-7.55 (m, 3H), 7.49 (d, J=8.1 Hz, 2H), 7.13 (d, J=8.2 Hz, 2H), 3.63-3.52 (m, 2H), 2.64 (t, J=6.3 Hz, 2H), 2.45-2.31 (m, 1H), 2.12 (d, J=6.7 Hz, 2H), 1.85-1.63 (m, 5H), 1.5-1.32 (m, 2H), 1.17-1.00 (m, 2H).
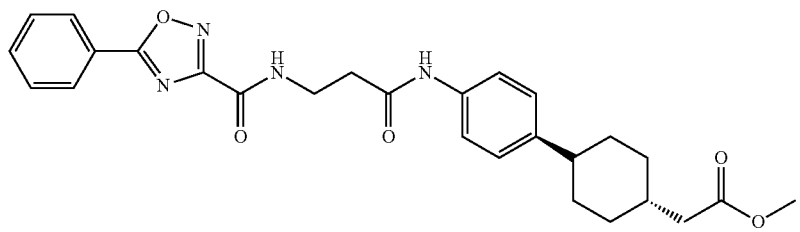
No. 16
¹H NMR (300 MHz, CDCl₃): δ8.16 (d, J=7.0 Hz, 2H), 7.89-7.80 (m, 1H), 7.64-7.47 (m, 4H), 7.43 (d, J=8.4 Hz, 2H), 7.15 (d, J=8.3 Hz, 2H), 3.93-3.83 (m, 2H), 3.68 (s, 3H), 2.77 (t, J=5.6 Hz, 2H), 2.50-2.36 (m, 1H), 2.24 (d, J=6.7 Hz, 2H), 1.92-1.79 (m, 5H), 1.54-1.37 (m, 2H), 1.22-1.05 (m, 2H).
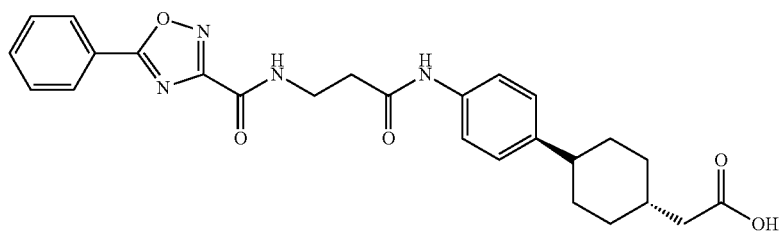
No. 17

¹H NMR (300 MHz, DMSO-d₆): δ 12.03 (s, 1H), 9.93 (s, 1H), 9.15-9.07 (m, 1H), 8.15 (d, J=7.5 Hz, 2H), 7.79-7.61 (m, 3H), 7.48 (d, J=8.2 Hz, 2H), 7.13 (d, J=8.2 Hz, 2H), 3.64-3.52 (m, 2H), 2.63 (t, J=6.8 Hz, 2H), 2.45-2.31 (m, 1H), 2.12 (d, J=6.5 Hz, 2H), 1.85-1.65 (m, 5H), 1.51-1.30 (m, 2H), 1.18-0.98 (m, 2H).
No. 18
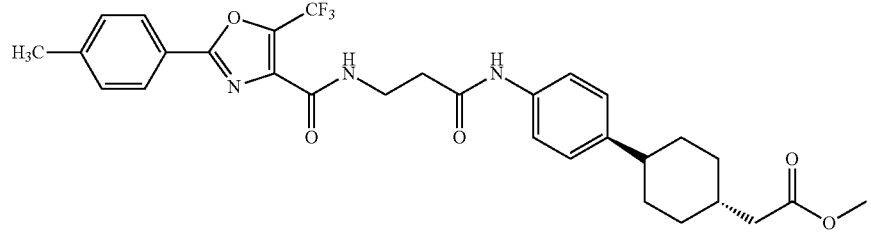
¹H NMR (300 MHz, CDCl₃): δ 7.95 (d, J=8.1 Hz, 2H), 7.85-7.77 (m, 1H), 7.53 (s, 1H), 7.43 (d, J=8.1 Hz, 2H), 7.30 (d, J=8.1 Hz, 2H), 7.15 (d, J=8.4 Hz, 2H), 3.88-3.78 (m, 2H), 3.68 (s, 3H), 2.75 (t, J=5.5 Hz, 2H), 2.48-2.36 (m, 4H), 2.24 (d, J=6.5 Hz, 2H), 1.92-1.79 (m, 5H), 1.53-1.38 (m, 2H), 1.22-1.05 (m, 2H).
No. 19
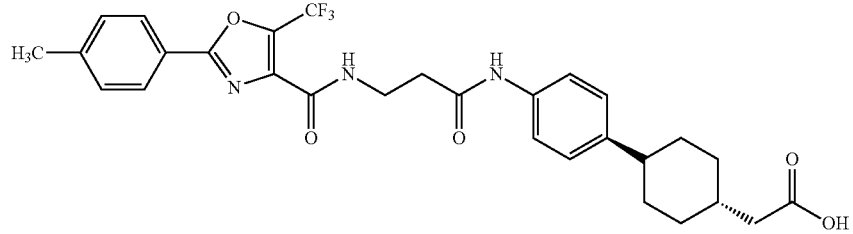
¹H NMR (300 MHz, DMSO-d₆): δ12.05 (s, 1H), 10.00 (s, 1H), 8.81-8.71 (m, 1H), 7.95 (d, J=8.2 Hz, 2H), 7.49 (d, J=8.4 Hz, 2H), 7.42 (d, J=8.0 Hz, 2H), 7.13 (d, J8.2 Hz, 2H), 3.61-3.49 (m, 2H), 2.63 (t, J=6.5 Hz, 2H), 2.44-2.31 (m, 4H), 2.12 (d, J=6.5 Hz, 2H), 1.85-1.64 (m, 5H), 1.49-1.32 (m, 2H), 1.17-0.99 (m, 2H).
No. 20
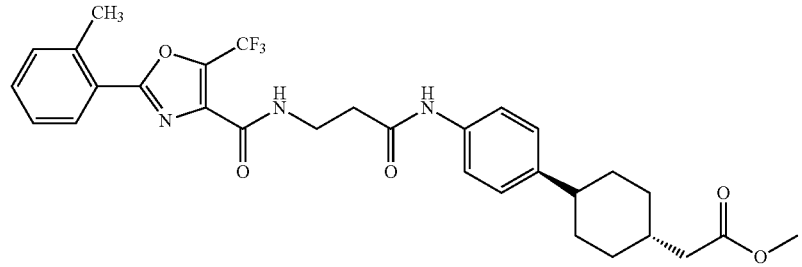

¹H NMR (300 MHz, CDCl₃-d₆): δ8.01 (d, J=7.7 Hz, 1H), 7.88-7.77 (m, 1H), 7.59 (s, 1H), 7.47-7.38 (m, 3H), 7.37-7.29 (m, 2H), 7.14 (d, J=8.0 Hz, 2H), 3.88-3.78 (m, 2H), 3.68 (s, 3H), 2.78-2.68 (m, 5H), 2.48-2.35 (m, 1H), 2.24 (d, J=6.3 Hz, 2H), 1.92-1.79 (m, 5H), 1.53-1.37 (m, 2H), 1.22-1.04 (m, 2H).

No. 21

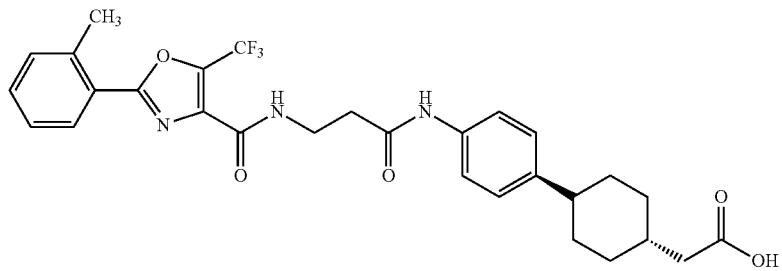

¹H NMR (500 MHz, DMSO-d₆): δ12.04 (s, 1H), 9.93 (s, 1H), 8.76-8.71 (m, 1H), 7.97 (d, J=7.8 Hz, 1H), 7.55-7.37 (m, 5H), 7.13 (d, J=8.2 Hz, 2H), 3.61-3.53 (m, 2H), 2.67-2.60 (m, 5H), 2.42-2.34 (m, 1H), 2.12 (d, J=6.8 Hz, 2H), 1.83-1.65 (m, 5H), 1.46-1.35 (m, 2H), 1.14-1.03 (m, 2H).

No. 22

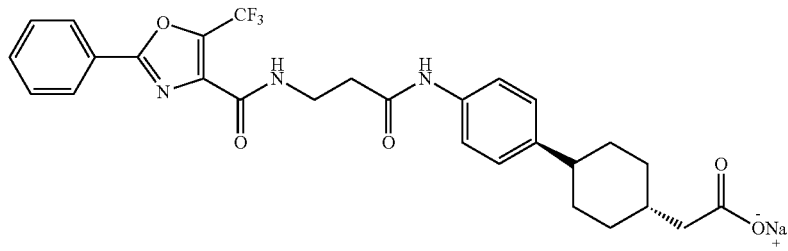

¹H NMR (300 MHz, DMSO-d₆): δ10.15 (s, 1H), 8.93-8.84 (m, 1H), 8.06 (d, J=7.0 Hz, 2H), 7.70-7.56 (m, 3H), 7.49 (d, J=8.0 Hz, 2H), 7.11 (d, J=8.2 Hz, 2H), 3.61-3.51 (m, 2H), 2.68-2.59 (m, 2H), 2.40-2.27 (m, 1H), 1.86-1.63 (m, 7H), 1.43-1.47 (m, 2H), 1.04-0.88 (m, 2H).

¹H NMR (500 MHz, DMSO-d₆): δ12.04 (s, 1H), 9.83 (s, 1H), 7.47 (d, J=8.0 Hz, 2H), 7.12 (d, J=8.0 Hz, 2H), 6.88-6.82 (m, 1H), 3.19 (q, J=6.3 Hz, 2H), 2.43 (t, J=7.1 Hz, 2H), 2.40-2.33 (m, 1H), 2.12 (d, J=6.8 Hz, 2H), 1.84-1.64 (m, 5H), 1.47-1.33 (m, 11H), 1.14-1.02 (m, 2H).

No. 23

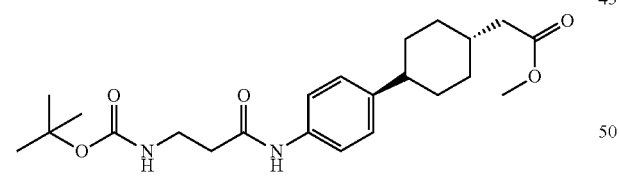

¹H NMR (300 MHz, CDCl₃): δ7.48 (s, 1H), 7.42 (d, J=8.2 Hz, 2H), 7.15 (d, J=8.2 Hz, 2H), 5.19-5.10 (m, 1H), 3.68 (s, 3H), 3.53-3.44 (m, 2H), 2.58 (t, J=5.5 Hz, 2H), 2.50-2.37 (m, 1H), 2.25 (d, J=6.5 Hz, 2H), 1.97-1.79 (m, 5H), 1.51-1.37 (m, 11H), 1.23-1.05 (m, 2H).

No. 24

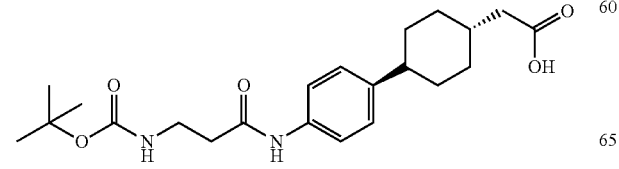

No. 25

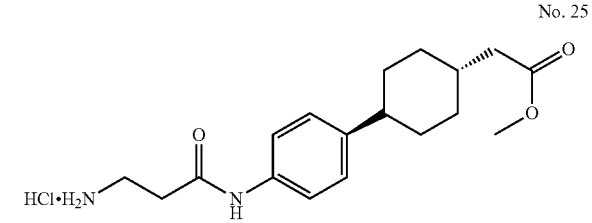

¹H NMR (500 MHz, DMSO-d₆): δ10.14 (s, 1H), 7.86 (s, 3H), 7.49 (d, J=8.0 Hz, 2H), 7.15 (d, J=8.0 Hz, 2H), 3.59 (s, 3H), 3.05 (t, J=6.7 Hz, 2H), 2.69 (t, J=6.7 Hz, 2H), 2.43-2.34 (m, 1H), 2.23 (d, J=6.7 Hz, 2H), 1.81-1.68 (m, 5H), 1.47-1.36 (m, 2H), 1.16-1.05 (m, 2H).

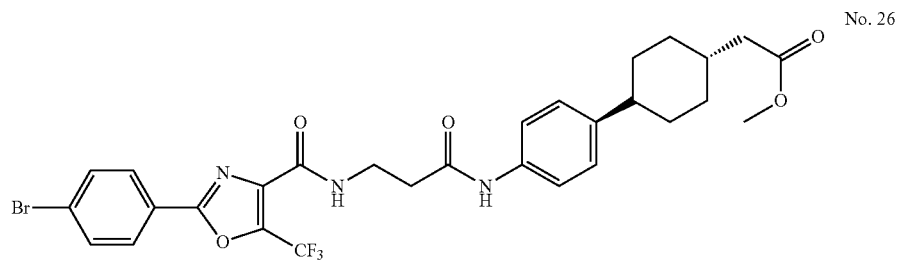
No. 26
¹H NMR (300 MHz, CDCl₃): δ 7.93 (d, J=8.3 Hz, 2H), 7.86-7.77 (m, 1H), 7.65 (d, J=8.6 Hz, 2H), 7.48-7.37 (m, 3H), 7.15 (d, J=8.2 Hz, 2H), 3.88-3.78 (m, 2H), 3.68 (s, 3H), 2.79-2.70 (m, 2H), 2.49-2.37 (m, 1H), 2.24 (d, J=6.6 Hz, 2H), 1.92-1.78 (m, 5H), 1.54-1.38 (m, 2H), 1.21-1.09 (m, 2H).
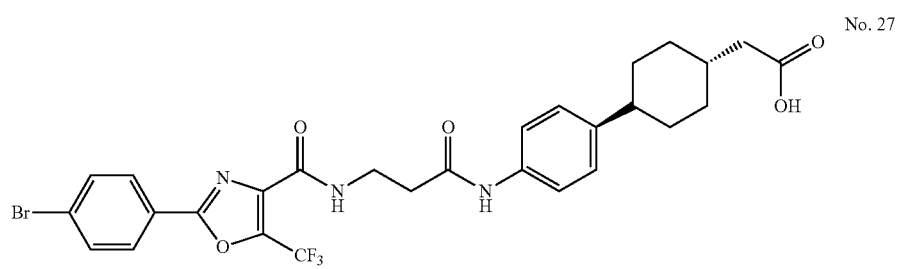
No. 27
¹H NMR (300 MHz, DMSO-d₆): δ12.04 (s, 1H), 9.92 (s, 1H), 8.83-8.73 (m, 1H), 7.98 (d, J=8.7 Hz, 2H), 7.83 (d, J=8.5 Hz, 2H), 7.48 (d, J=8.3 Hz, 2H), 7.13 (d, J=8.4 Hz, 2H), 3.60-3.50 (m, 2H), 2.62 (t, J6.4 Hz, 2H), 2.44-2.32 (m, 1H), 2.12 (d, J=6.5 Hz, 2H), 1.84-1.68 (m, 5H), 1.49-1.33 (m, 2H), 1.18-1.00 (m, 2H).
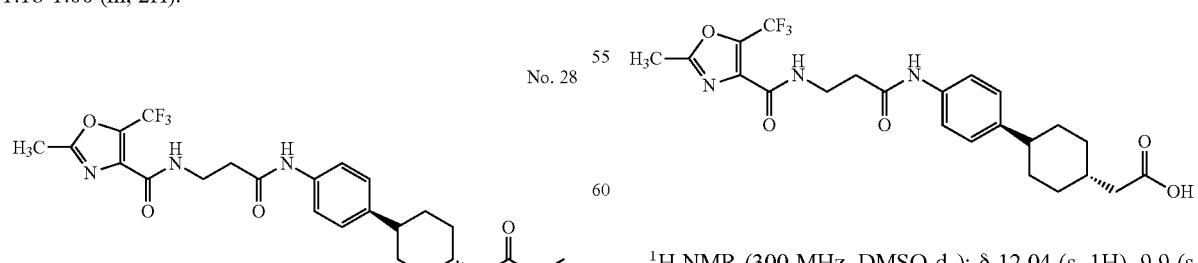
No. 28
No. 29
¹H NMR (300 MHz, CDCl₃): δ 7.77-7.66 (m, 2H), 7.43 (d, J=8.3 Hz, 2H), 7.14 (d, J=8.2 Hz, 2H), 3.81-3.71 (m, 2H), 3.68 (s, 3H), 2.69 (t, J=5.6 Hz, 2H), 2.5 (s, 3H), 2.48-2.36 (m, 1H), 2.25 (d, J=6.5 Hz, 2H), 1.92-1.76 (m, 5H), 1.55-1.37 (m, 2H), 1.22-1.05 (m, 2H).
¹H NMR (300 MHz, DMSO-d₆): δ 12.04 (s, 1H), 9.9 (s, 1H), 8.68-8.58 (m, 1H), 7.47 (J=8.3 Hz, 2H), 7.13 (d, J=8.2 Hz, 2H), 3.55-3.44 (m, 2H), 2.62-2.51 (m, 5H), 2.44-2.32 (m, 1H), 2.21 (d, J=6.5 Hz, 2H), 1.85-1.64 (m, 5H), 1.49-1.32 (m, 2H), 1.16-1.00 (m, 2H).

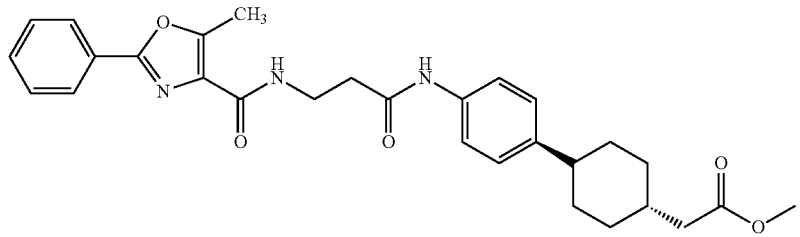
No. 30
$^1$H NMR (300 MHz, CDCl$_3$): δ 8.16-8.08 (m, 1H), 8.03-7.93 (m, 2H), 7.75 (s, 1H), 7.49-7.41 (m, 5H), 7.14 (d, J=8.3 Hz, 2H), 3.85-3.76 (m, 2H), 3.68 (s, 3H), 2.76-2.68 (m, 5H), 2.49-2.36 (m, 1H), 2.24 (d, J=6.6 Hz, 2H), 1.92-1.80 (m, 5H), 1.54-1.37 (m, 2H), 1.21-1.05 (m, 2H).
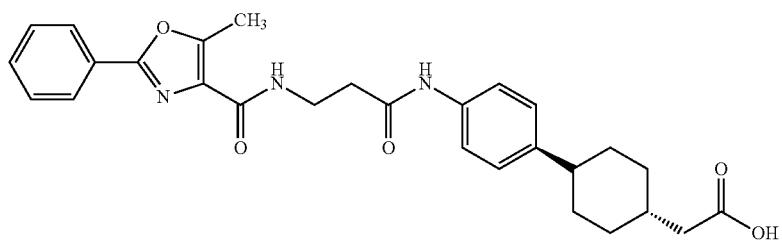
No. 31
$^1$H NMR (300 MHz, DMSO-d$_6$): δ12.05 (s, 1H), 9.91 (s, 1H), 8.25-8.17 (m, 1H), 8.01-7.93 (m, 2H), 7.59-7.51 (m, 3H), 7.48 (d, J=8.4 Hz, 2H), 7.13 (d, J=8.4 Hz, 2H), 3.58-3.49 (m, 2H), 2.65 (s, 3H), 2.60 (t, 7.4 Hz, 2H), 2.44-2.31 (m, 1H), 2.12 (d, J=6.6 Hz, 2H), 1.85-1.64 (m, 5H), 1.49-1.32 (m, 2H), 1.16-0.99 (m, 2H).
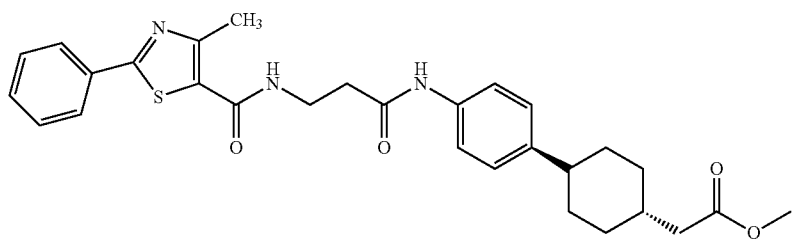
No. 32
$^1$H NMR (300 MHz, CDCl$_3$): δ 7.96-7.87 (m, 2H), 7.48-7.36 (m, 6H), 7.16 (d, J=8.3 Hz, 2H), 6.92-6.85 (m, 1H), 3.84-3.75 (m, 2H), 3.68 (s, 3H), 2.77-2.67 (m, 5H), 2.52-2.37 (m, 1H), 2.24 (d, J=6.5 Hz, 2H), 1.92-1.80 (m, 5H), 1.55-1.38 (m, 2H), 1.23-1.05 (m, 2H).
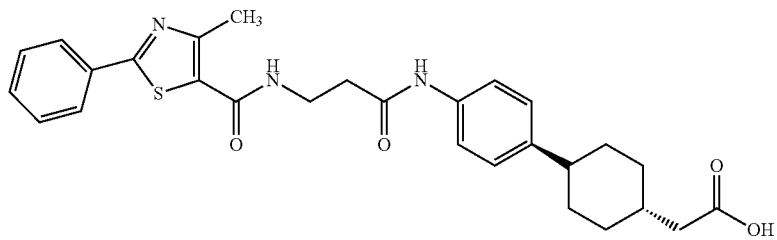
No. 33

¹H NMR (300 MHz, DMSO-d₆): δ12.04 (s, 1H), 9.92 (s, 1H), 8.43-8.35 (m, 1H), 7.96-7.87 (m, 2H), 7.55-7.44 (m, 5H), 7.13 (d, J=8.3 Hz, 2H), 3.57-3.46 (m, 2H), 2.64-2.54 (m, 5H), 2.44-2.32 (m, 1H), 2.12 (d, J=6.7 Hz, 2H), 1.85-1.64 (m, 5H), 1.49-1.33 (m, 2H), 1.18-1.00 (m, 2H).
No. 34
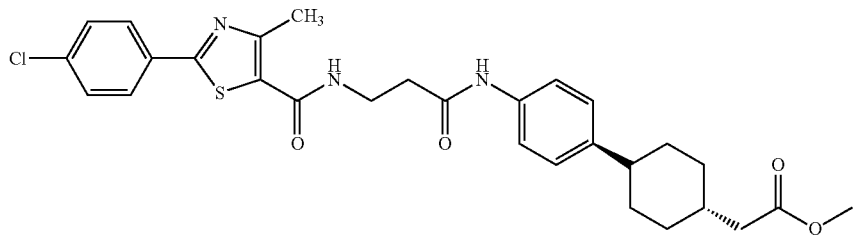
¹H NMR (300 MHz, DMSO-d₆): δ 9.92 (s, 1H), 8.45-8.38 (m, 1H), 7.93 (d, J=8.6 Hz, 2H), 7.57 (d, J=8.6 Hz, 2H), 7.48 (d, J=8.3 Hz, 2H), 7.13 (d, J=8.1 Hz, 2H), 3.59 (s, 3H), 3.55-3.46 (m, 2H), 2.64-2.54 (m, 5H), 2.44-2.32 (m, 1H), 2.23 (d, J=6.4 Hz, 2H), 1.82-1.66 (m, 5H), 1.5-1.32 (m, 2H), 1.2-1.01 (m, 2H).
No. 35
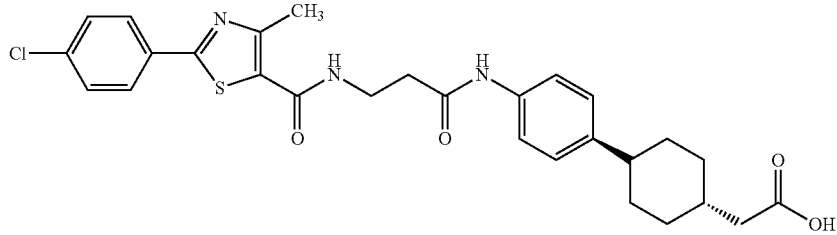
¹H NMR (300 MHz, DMSO-d₆): δ12.05 (s, 1H), 9.95 (s, 1H), 8.47-8.39 (m, 1H), 7.93 (d, J=8.5 Hz, 2H), 7.57 (d, J=8.5 Hz, 2H), 7.49 (d, J=8.4 Hz, 2H), 7.13 (d, J=8.4 Hz, 2H), 3.55-3.47 (m, 2H), 2.62-2.56 (m, 5H), 2.44-2.32 (m, 1H), 2.12 (d, J=6.7 Hz, 2H), 1.85-1.68 (m, 5H), 1.49-1.33 (m, 2H), 1.17-1.03 (m, 2H).
No. 36
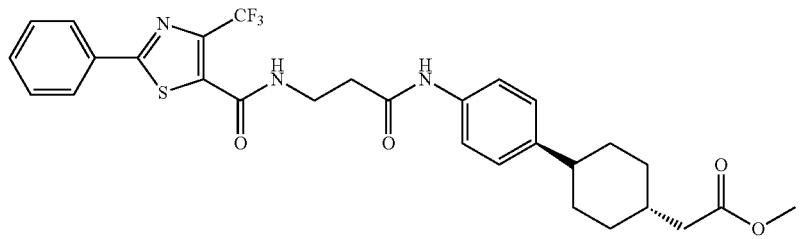
¹H NMR (300 MHz, CDCl₃): δ 9.93 (s, 1H), 9.16-9.09 (m, 1H), 7.93 (d, J=7.70 Hz, 2H), 7.52-7.42 (m, 3H), 7.39 (d, J=8.2 Hz, 2H), 7.16 (d, J=8.1 Hz, 2H), 3.86-3.78 (m, 2H), 3.68 (s, 3H), 2.75-2.68 (m, 2H), 2.50-2.37 (m, 1H), 2.24 (d, J=6.5 Hz, 2H), 1.92-1.82 (m, 5H), 1.56-1.38 (m, 2H), 1.21-1.09 (m, 2H).

No. 37
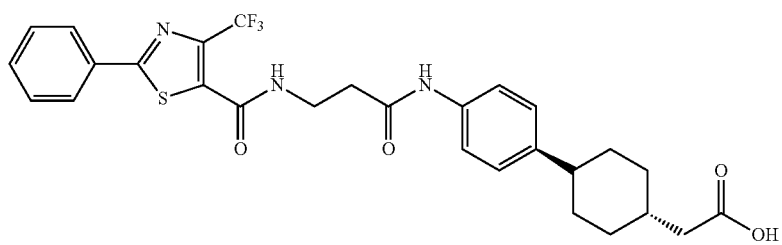
¹H NMR (300 MHz, DMSO-$d_6$): δ12.02 (s, 1H), 9.93 (s, 1H), 9.16-9.09 (m, 1H), 7.97 (d, J=7.7 Hz, 2H), 7.63-7.44 (m, 5H), 7.14 (d, J=8.4 Hz, 2H), 3.56-3.47 (m, 2H), 2.59 (t, J=6.8 Hz, 2H), 2.45-2.32 (m, 1H), 2.12 (d, J=6.7 Hz, 2H), 1.85-1.63 (m, 5H), 1.50-1.33 (m, 2H), 1.17-1.00 (m, 2H).
¹H NMR (300 MHz, DMSO-$d_6$): δ 12.03 (s, 1H), 11.37 (s, 1H), 9.90 (s, 1H), 8.95-8.73 (m, 2H), 8.45-8.30 (m, 1H), 7.94 (s, 1H), 7.48 (d, J=8.3 Hz, 2H), 7.13 (d, J=8.3 Hz, 2H), 3.61-3.40 (m, 2H), 2.69-2.54 (m, 2H), 2.45-2.32 (m, 1H), 2.13 (d, J=6.7 Hz, 2H), 1.93-1.64 (m, 5H), 1.57-1.30 (m, 2H), 1.19-0.98 (m, 2H).
No. 38
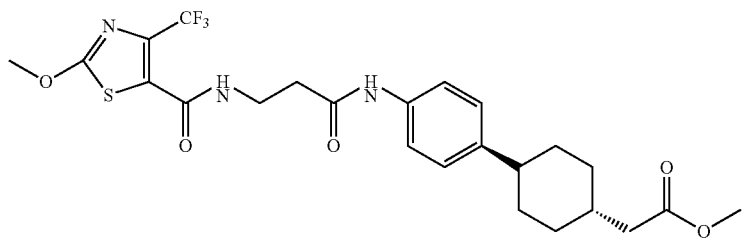
LC-MS (m/z): 528 (MH⁺)
No. 39
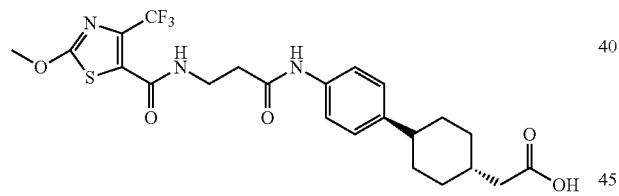
¹H NMR (300 MHz, DMSO-$d_6$): δ12.02 (s, 1H), 9.90 (s, 1H), 8.98-8.87 (m, 1H), 7.47 (d, J=8.7 Hz, 2H), 7.13 (d, J=8.6 Hz, 2H), 4.07 (s, 3H), 3.50-3.40 (m, 2H), 2.54 (t, J=6.8 Hz, 2H), 2.45-2.32 (m, 1H), 2.12 (d, J=6.7 Hz, 2H), 1.85-1.66 (m, 5H), 1.50-1.33 (m, 2H), 1.17-1.00 (m, 2H).
No. 40
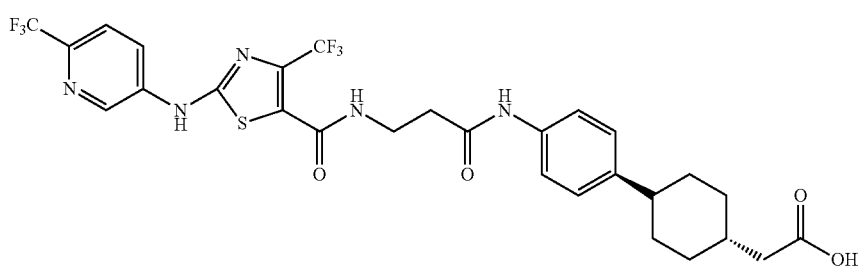

No. 41
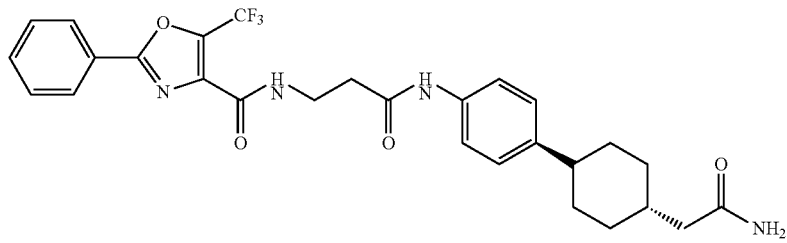
¹H NMR (300 MHz, DMSO-d₆) δ9.93 (s, 1H), 8.83-8.74 (m, 1H), 8.11-8.03 (m, 2H), 7.72-7.56 (m, 3H), 7.48 (d, J=8.3 Hz, 2H), 7.13 (d, J=8.3 Hz, 2H), 3.61-3.51 (m, 2H), 2.68-2.59 (m, 2H), 2.45-2.31 (m, 1H), 2.19 (d, J=6.3 Hz, 2H), 1.86-1.66 (m, 5H), 1.50-1.31 (m, 2H), 1.18-0.99 (m, 2H).
No. 42
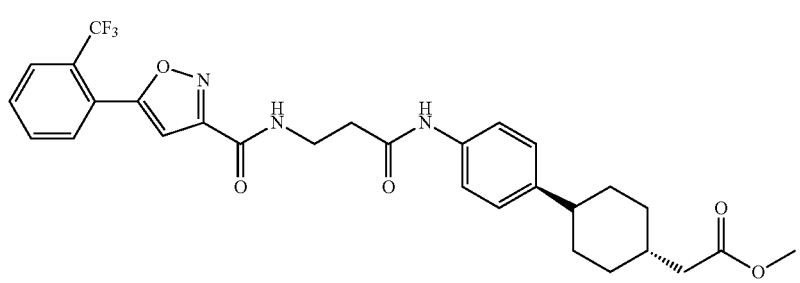
LC-MS (m/z): 558 (MH⁺)
No. 43
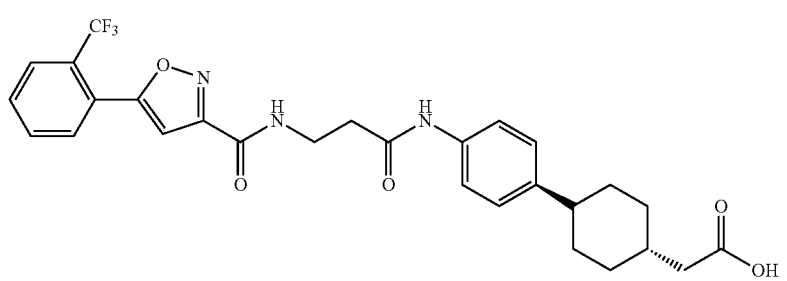
¹H NMR (300 MHz, DMSO-d₆) δ12.01 (s, 1H), 9.91 (s, 1H), 8.97 (t, J=5.5 Hz, 1H), 7.98 (d, J=7.4 Hz, 1H), 7.90-7.77 (m, 3H), 7.48 (d, J=8.4 Hz, 2H), 7.17-7.10 (m, 3H), 3.60-3.51 (m, 2H), 2.62 (t, J=6.8 Hz, 2H), 2.45-2.32 (m, 1H), 2.12 (d, J=6.6 Hz, 2H), 1.85-1.64 (m, 5H), 1.50-1.32 (m, 2H), 1.16-1.00 (m, 2H).
No. 44
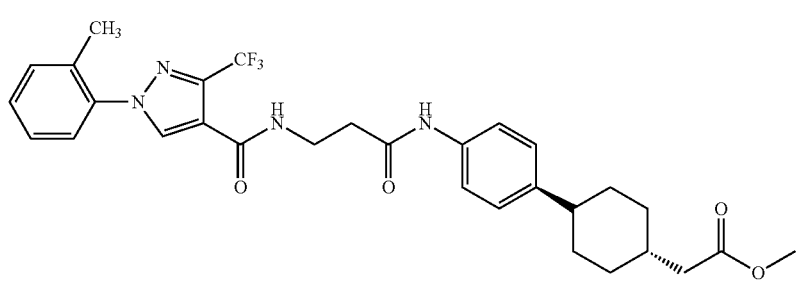
LC-MS (m/z): 571 (MH+)

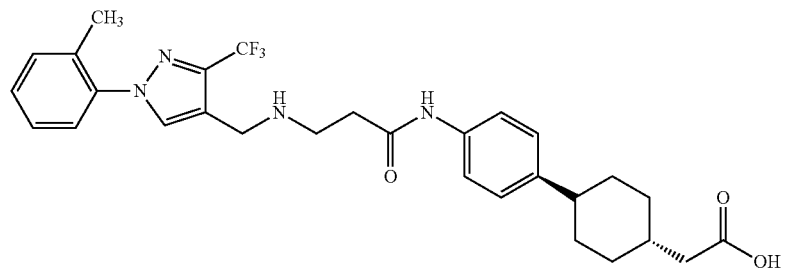
No. 45
¹H NMR (300 MHz, DMSO-d₆) δ12.04 (s, 1H), 9.91 (s, 1H), 8.62 (s, 1H), 8.51-8.43 (m, 1H), 7.53-7.35 (m, 6H), 7.12 (d, J=8.5 Hz, 2H), 3.54-3.44 (m, 2H), 2.62-2.54 (m, 2H), 2.44-2.31 (m, 1H), 2.19 (s, 3H), 2.12 (d, J=6.6 Hz, 2H), 1.84-1.61 (m, 5H), 1.49-1.31 (m, 2H), 1.17-0.99 (m, 2H).
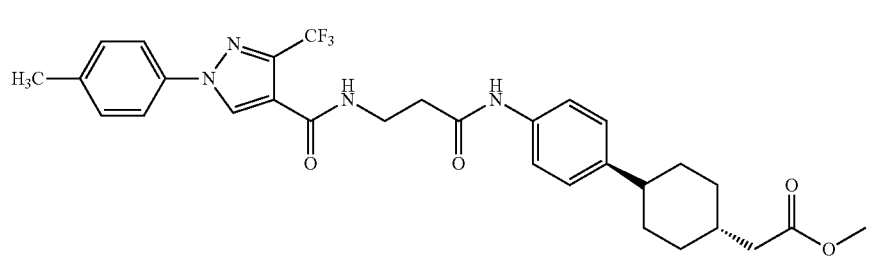
No. 46
LC-MS (m/z): 571 (MH⁺)
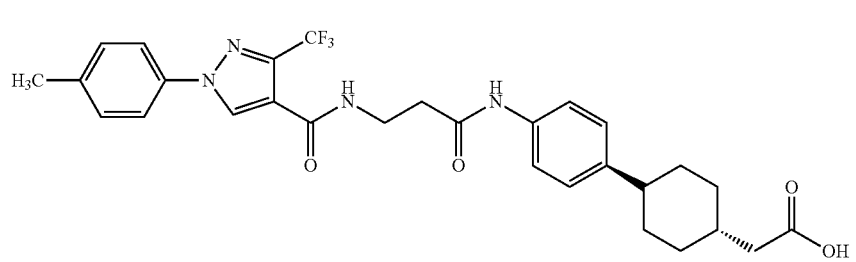
No. 47
¹H NMR (300 MHz, DMSO-d₆) δ12.05 (s, 1H), 10.01 (s, 1H), 9.16 (s, 1H), 8.60-8.53 (m, 1H), 7.68 (d, J=8.4 Hz, 2H), 7.50 (d, J=8.4 Hz, 2H), 7.38 (d, J=8.4 Hz, 2H), 7.12 (d, J=8.5 Hz, 2H), 3.54-3.45 (m, 2H), 2.64-2.55 (m, 2H), 2.39-2.32 (m, 4H), 2.12 (d, J=6.8 Hz, 2H), 1.84-1.65 (m, 5H), 1.49-1.32 (m, 2H), 1.16-0.99 (m, 2H).
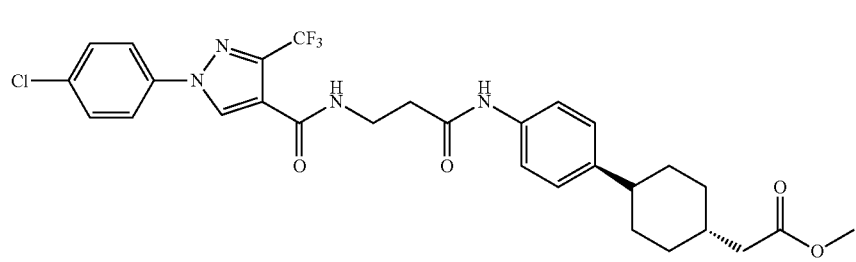
No. 48
LC-MS (m/z): 591 (MH⁺)

No. 49
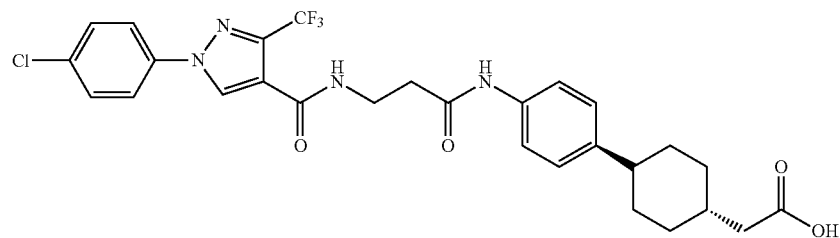
¹H NMR (300 MHz, DMSO-d₆) δ12.03 (s, 1H), 9.91 (s, 1H), 9.09 (s, 1H), 8.51-8.43 (m, 1H), 7.83 (d, J=8.9 Hz, 2H), 7.66 (d, J=8.8 Hz, 2H), 7.49 (d, J=8.5 Hz, 2H), 7.13 (d, J=8.6 Hz, 2H), 3.55-3.45 (m, 2H), 2.63-2.54 (m, 2H), 2.44-2.31 (m, 1H), 2.12 (d, J=6.7 Hz, 2H), 1.85-1.64 (m, 5H), 1.49-1.32 (m, 2H), 1.17-0.99 (m, 2H).
No. 50
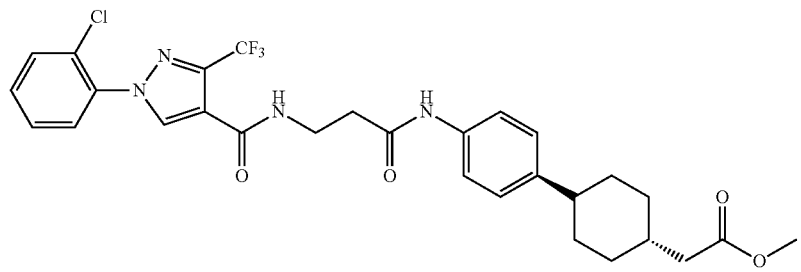
LC-MS (m/z): 591 (MH⁺)
No. 51
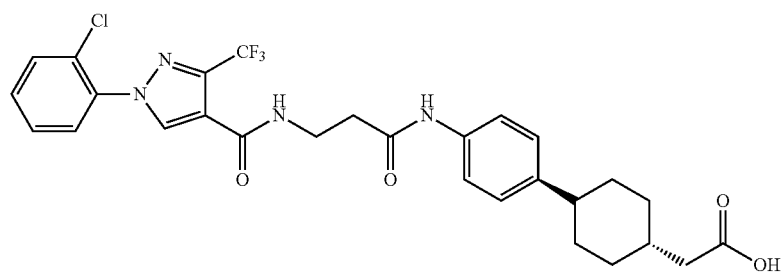
¹H NMR (300 MHz, DMSO-d₆) δ11.99 (s, 1H), 9.90 (s, 1H), 8.73 (s, 1H), 8.55-8.47 (m, 1H), 7.78-7.66 (m, 2H), 7.65-7.52 (m, 2H), 7.48 (d, J=8.3 Hz, 2H), 7.12 (d, J=8.3 Hz, 2H), 3.55-3.44 (m, 2H), 2.62-2.54 (m, 2H), 2.44-2.31 (m, 1H), 2.12 (d, J=6.8 Hz, 2H), 1.85-1.61 (m, 5H), 1.50-1.31 (m, 2H), 1.18-0.99 (m, 2H).
No. 52
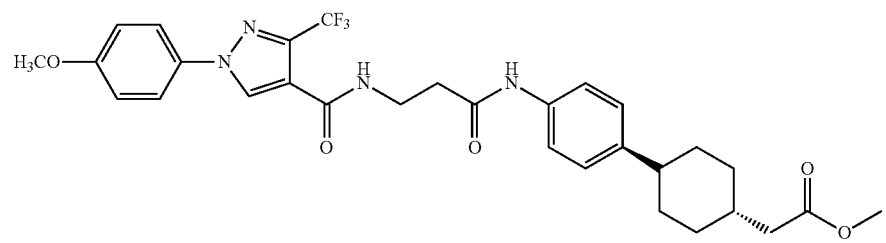
LC-MS (m/z): 587 (MH⁺)

No. 53
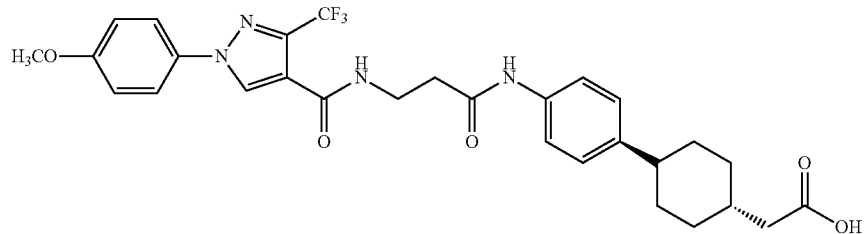
¹H NMR (300 MHz, DMSO-d₆) δ12.02 (s, 1H), 9.91 (s, 1H), 8.94 (s, 1H), 8.47-8.39 (m, 1H), 7.70 (d, J=9.4 Hz, 2H), 7.49 (d, J=8.6 Hz, 2H), 7.17-7.08 (m, 4H), 3.81 (s, 3H), 3.55-3.44 (m, 2H), 2.63-2.54 (m, 2H), 2.44-2.31 (m, 1H), 2.12 (d, J=6.9 Hz, 2H), 1.84-1.60 (m, 5H), 1.49-1.31 (m, 2H), 1.17-0.99 (m, 2H).
No. 54
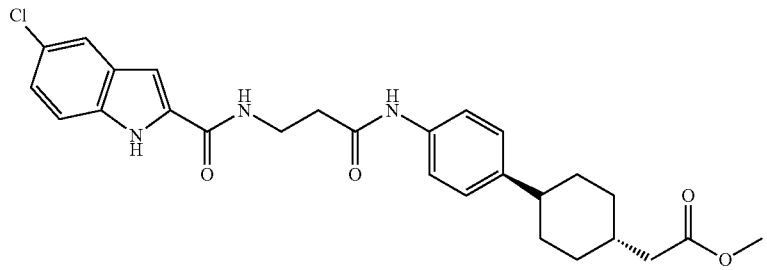
LC-MS (m/z): 496 (MH⁺)
No. 55
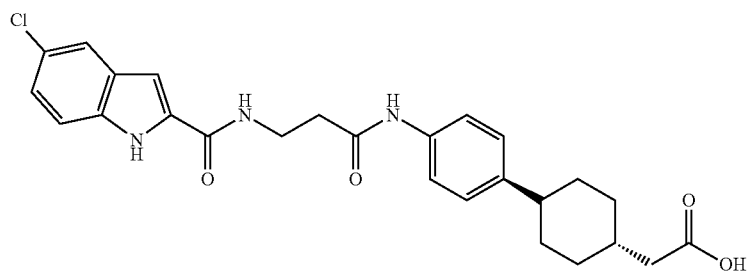
¹H NMR (300 MHz, DMSO-d₆) δ12.03 (s, 1H), 11.78 (s, 1H), 9.90 (s, 1H), 8.72-8.65 (m, 1H), 7.69-7.66 (m, 1H), 7.48 (d, J=8.2 Hz, 2H), 7.41 (d, J=8.7 Hz, 2H), 7.19-7.05 (m, 4H), 3.62-3.50 (m, 2H), 2.66-2.55 (m, 2H), 2.45-2.31 (m, 1H), 2.12 (d, J=6.8 Hz, 2H), 1.85-1.61 (m, 5H), 1.50-1.32 (m, 2H), 1.17-0.99 (m, 2H).
No. 56
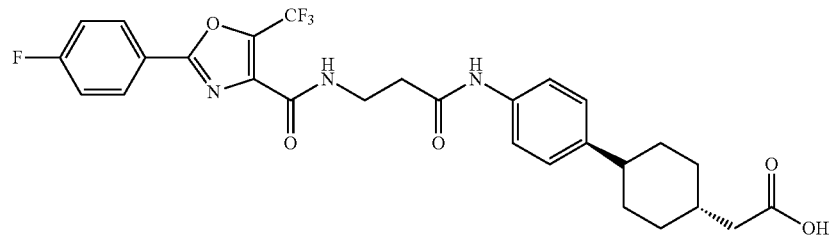

¹H NMR (300 MHz, DMSO-d₆) δ12.02 (s, 1H), 9.92 (s, 1H), 8.81-8.72 (m1H), 8.16-8.07 (m, 2H), 7.53-7.42 (m, 4H), 7.13 (d, J=8.0 Hz, 2H), 3.61-3.51 (m, 2H), 2.67-2.58 (m, 2H), 2.45-2.31 (m, 1H), 2.13 (d, J=6.8 Hz, 2H), 1.85-1.62 (m, 5H), 1.49-1.32 (m, 2H), 1.18-1.00 (m, 2H).
No. 57
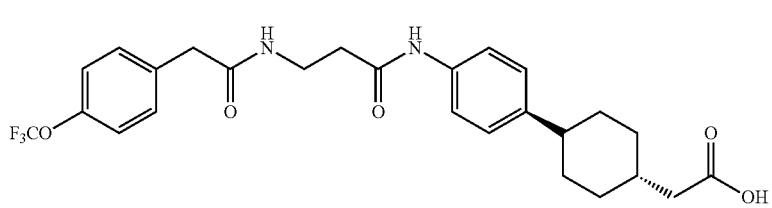
¹H NMR (300 MHz, DMSO-d₆) δ12.03 (s, 1H), 9.83 (s, 1H), 8.32-8.24 (m, 1H), 7.56 (d, J=8.1 Hz, 2H), 7.48 (d, J=8.1 Hz, 2H), 7.43 (d, J=8.3 Hz, 2H), 7.13 (d, J=8.3 Hz, 2H), 3.5 (s, 2H), 3.38-3.27 (m, 2H), 2.47-2.32 (m, 3H), 2.13 (d, J=6.9 Hz, 2H), 1.85-1.65 (m, 5H), 1.50-1.33 (m, 2H), 1.17-1.00 (m, 2H).
No. 58
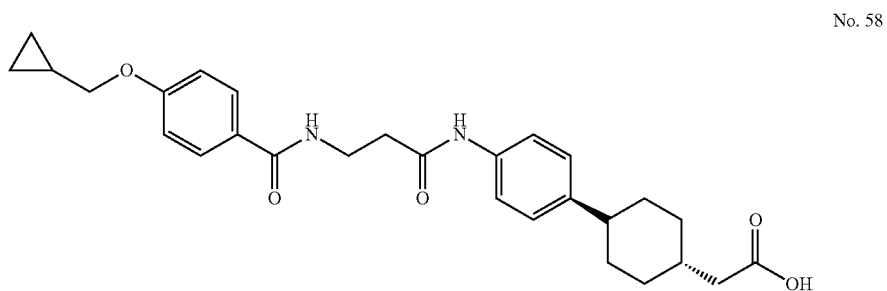
¹H NMR (300 MHz, DMSO-d₆) δ12.02 (s, 1H), 9.87 (s, 1H), 8.47-8.38 (m, 1H), 7.79 (d, J=8.6 Hz, 2H), 7.48 (d, J=7.5 Hz, 2H), 7.12 (d, J=8.3 Hz, 2H), 6.95 (d, J=8.9 Hz, 2H), 3.85 (d, J=7.2 Hz, 2H), 3.55-3.45 (m, 2H), 2.57 (t, J=7.2 Hz, 2H), 2.44-2.31 (m, 1H), 2.12 (d, J=6.7 Hz, 2H), 1.85-1.61 (m, 5H), 1.50-1.32 (m, 2H), 1.28-0.99 (m, 3H), 0.61-0.52 (m, 2H), 0.35-0.27 (m, 2H).
No. 59
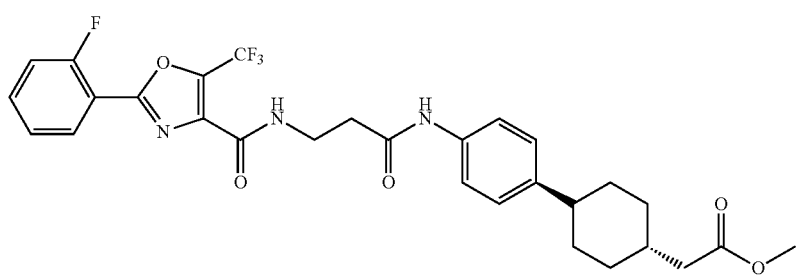
¹H NMR (300 MHz, CDCl₃): δ 8.06 (t, J=7.4 Hz, 1H), 7.86-7.77 (m, 1H), 7.60-7.39 (m, 4H), 7.34-7.20 (m, 2H), 7.15 (d, J=8.0 Hz, 2H), 3.89-3.79 (m, 2H), 3.68 (s, 3H), 2.79-2.71 (m, 2H), 2.50-2.36 (m, 1H), 2.24 (d, J=6.4 Hz, 2H), 1.92-1.77 (m, 5H), 1.54-1.37 (m, 2H), 1.22-1.04 (m, 2H).

No. 60
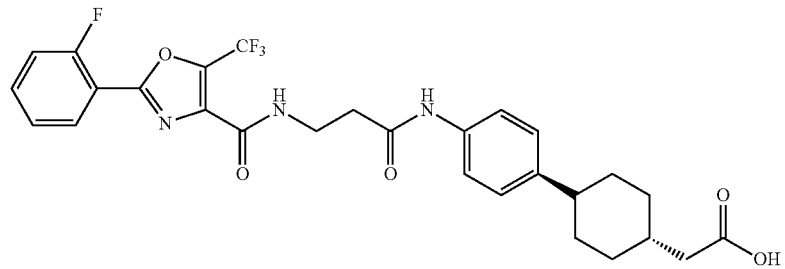
¹H NMR (300 MHz, DMSO-d₆) δ11.93 (s, 1H), 9.91 (s, 1H), 8.78-8.69 (m, 1H), 8.15-8.05 (m, 1H), 7.77-7.65 (m, 1H), 7.54-7.39 (m, 4H), 7.13 (d, J=7.6 Hz, 2H), 3.62-3.49 (m, 2H), 2.65-2.57 (m, 2H), 2.45-2.31 (m, 1H), 2.12 (d, J=6.8 Hz, 2H), 1.85-1.61 (m, 5H), 1.50-1.32 (m, 2H), 1.16-0.99 (m, 2H).
No. 61
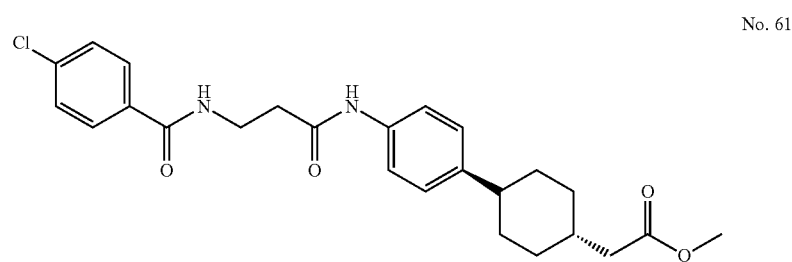
¹H NMR (300 MHz, CDCl₃): δ 7.71 (d, J=8.5 Hz, 2H), 7.50 (s, 1H), 7.44-7.34 (m, 4H), 7.21-7.11 (m, 3H), 3.86-3.76 (m, 2H), 3.68 (s, 3H), 2.75-2.66 (m, 2H), 2.50-2.37 (m, 1H), 2.25 (d, J=6.6 Hz, 2H), 1.93-1.79 (m, 5H), 1.56-1.37 (m, 2H), 1.22-1.04 (m, 2H).
No. 62
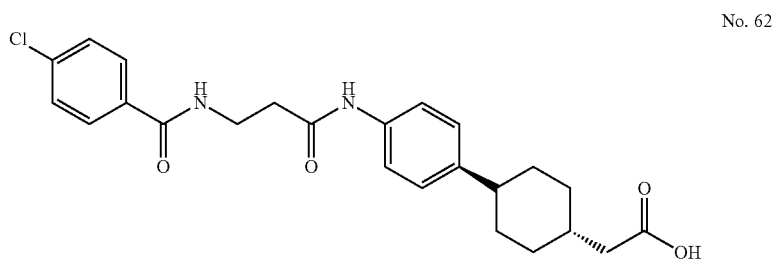
¹H NMR (300 MHz, DMSO-d₆): δ9.93 (s, 1H), 8.76-8.67 (m, 1H), 7.85 (d, J=8.18 Hz, 2H), 7.55-7.44 (m, 4H), 7.12 (d, J=8.4 Hz, 2H), 3.57-3.48 (m, 2H), 2.63-2.54 (m, 2H), 2.44-2.30 (m, 1H), 2.08 (d, J=6.6 Hz, 2H), 1.86-1.62 (m, 5H), 1.49-1.31 (m, 2H), 1.15-0.97 (m, 2H).
No. 63
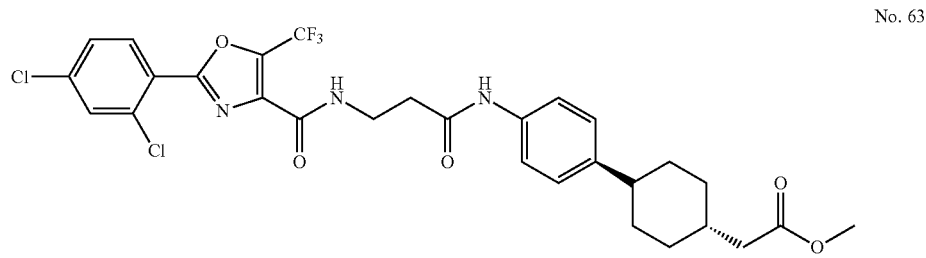

¹H NMR (300 MHz, CDCl₃): δ 8.01-7.95 (m, 1H), 7.86-7.78 (m, 1H), 7.57 (s, 1H), 7.49-7.36 (m, 4H), 7.14 (d, J=7.7 Hz, 2H), 3.87-3.78 (m, 2H), 3.68 (s, 3H), 2.78-2.70 (m, 2H), 2.49-2.36 (m, 1H), 2.25 (d, J=7.0 Hz, 2H), 1.92-1.78 (m, 5H), 1.54-1.37 (m, 2H), 1.22-1.05 (m, 2H).
No. 64
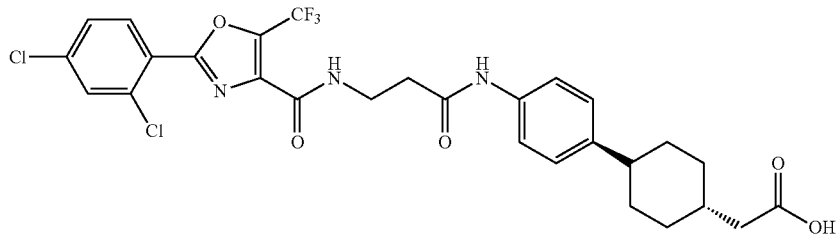
¹H NMR (300 MHz, DMSO-d₆): δ12.01 (s, 1H), 9.91 (s, 1H), 8.81-8.73 (m, 1H), 8.08 (d, J=8.6 Hz, 1H), 7.93 (d, J=2 Hz, 1H), 7.69 (dd, J=8.6, 2.0 Hz, 1H), 7.47 (d, J=8.6 Hz, 2H), 7.13 (d, J=8.4 Hz, 2H), 3.62-3.49 (m, 2H), 2.66-2.57 (m, 2H), 2.45-2.31 (m, 1H), 2.12 (d, J=6.7 Hz, 2H), 1.85-1.64 (m, 5H), 1.50-1.32 (m, 2H), 1.18-1.00 (m, 2H).
No. 65
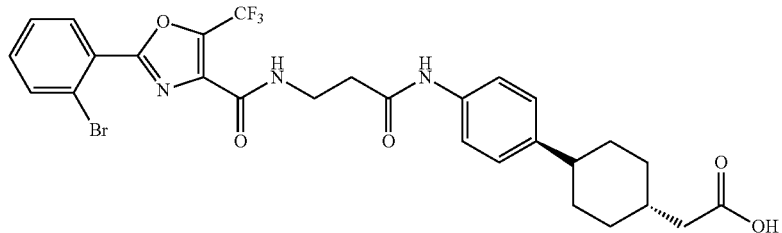
¹H NMR (300 MHz, DMSO-d₆): δ12.07 (s, 1H), 9.91 (s, 1H), 8.79-8.72 (m, 1H), 8.02-7.97 (m, 1H), 7.90-7.85 (m, 1H), 7.65-7.54 (m, 2H), 7.47 (d, J=8.4 Hz, 2H), 7.13 (d, J=8.4 Hz, 2H), 3.61-3.51 (m, 2H), 2.66-2.58 (m, 2H), 2.45-2.32 (m, 1H), 2.11 (d, J=6.9 Hz, 2H), 1.85-1.65 (m, 5H), 1.49-1.32 (m, 2H), 1.17-1.00 (m, 2H).
No. 66
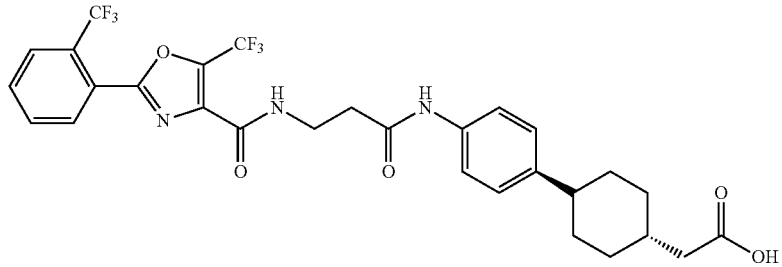
¹H NMR (300 MHz, DMSO-d₆): 12.03 (s, 1H), 9.90 (s, 1H), 8.79 (t, J=5.97 Hz, 1H), 8.15-8.10 (m, 1H), 8.06-8.00 (m, 1H), 7.97-7.86 (m, 2H), 7.47 (d, J=8.38 Hz, 2H), 7.13 (d, J=8.51 Hz, 2H), 3.61-3.50 (m, 2H), 2.62 (t, J=7.24 Hz, 2H), 2.45-2.31 (m, 1H), 2.12 (d, J=6.85 Hz, 2H), 1.85-1.63 (m, 5H), 1.49-1.32 (m, 2H), 1.18-0.99 (m, 2H).

No. 67
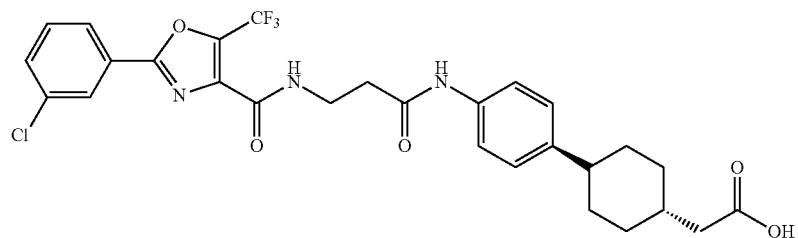
¹H NMR (300 MHz, DMSO-d₆): 12.05 (s, 1H), 9.92 (s, 1H), 8.82 (t, J=5.64 Hz, 1H), 8.07 (s, 1H), 8.01 (d, J=7.72 Hz, 1H), 7.74 (d, J=7.93 Hz, 1H), 7.65 (t, J=7.86 Hz, 1H), 7.48 (d, J=8.30 Hz, 2H), 7.13 (d, J=8.30 Hz, 2H), 3.61-3.51 (m, 2H), 2.62 (t, J=6.70 Hz, 2H), 2.45-2.31 (m, 1H), 2.12 (d, J=6.48 Hz, 2H), 1.85-1.65 (m, 5H), 1.50-1.30 (m, 2H), 1.18-0.99 (m, 2H).
No. 68
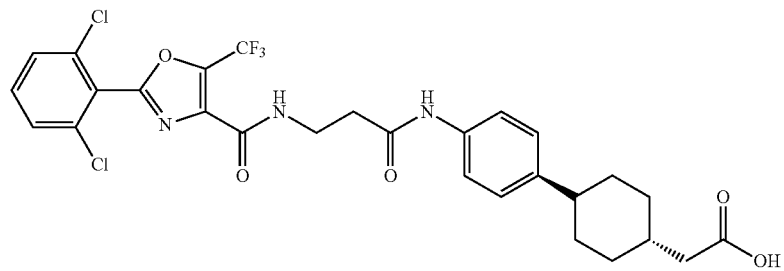
¹H NMR (300 MHz, DMSO-d₆): 12.07 (s, 1H), 9.89 (s, 1H), 8.94 (t, J=5.83 Hz, 1H), 7.78-7.73 (m, 3H), 7.46 (d, J=8.35 Hz, 2H), 7.12 (d, J=8.48 Hz, 2H), 3.60-3.49 (m, 2H), 2.61 (t, J=6.76 Hz, 2H), 2.44-2.31 (m, 1H), 2.12 (d, J=6.89 Hz, 2H), 1.85-1.62 (m, 5H), 1.49-1.31 (m, 2H), 1.20-0.99 (m, 2H).
No. 69
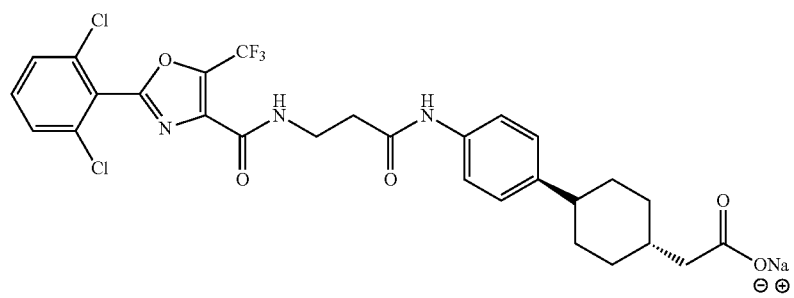

¹H NMR (300 MHz, DMSO-d₆): 10.15 (s, 1H), 9.06 (t, J=5.63 Hz, 1H), 7.79-7.72 (m, 3H), 7.47 (d, J=8.43 Hz, 2H), 7.10 (d, J=8.49 Hz, 2H), 3.60-3.49 (m, 2H), 2.63 (t, J=6.93 Hz, 2H), 2.39-2.25 (m, 1H), 1.85-1.54 (m, 7H), 1.43-1.22 (m, 2H), 1.03-0.84 (m, 2H).
No. 70
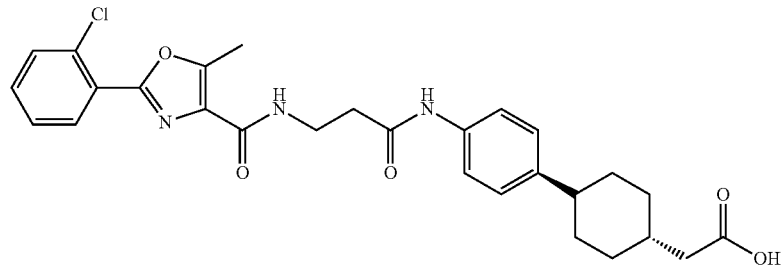
¹H NMR (300 MHz, DMSO-d₆): 12.03 (s, 1H), 9.89 (s, 1H), 8.19 (t, J=5.91 Hz, 1H), 7.94 (dd, J=7.34, 1.62 Hz, 1H), 7.65 (dd, J=7.96, 1.16 Hz, 1H), 7.60-7.50 (m, 2H), 7.47 (d, J=8.12 Hz, 2H), 7.13 (d, J=8.44 Hz, 2H), 3.62-3.48 (m, 2H), 2.65 (s, 3H), 2.59 (t, J=6.94 Hz, 2H), 2.45-2.31 (m, 1H), 2.12 (d, J=6.73 Hz, 2H), 1.84-1.61 (m, 5H), 1.49-1.32 (m, 2H), 1.17-1.00 (m, 2H).
No. 71
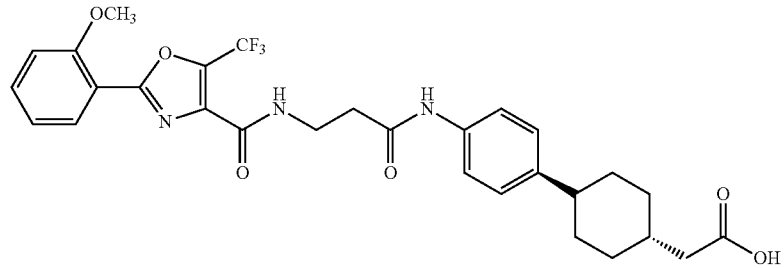
¹H NMR (300 MHz, DMSO-d₆): 12.03 (s, 1H), 9.91 (s, 1H), 8.72 (t, J=5.91 Hz, 1H), 7.93 (dd, J=7.72, 1.57 Hz, 1H), 7.67-7.58 (m, 1H), 7.48 (d, J=8.56 Hz, 2H), 7.27 (d, J=8.47 Hz, 1H), 7.17-7.09 (m, 3H), 3.89 (s, 3H), 3.60-3.50 (m, 2H), 2.62 (t, J=7.06 Hz, 2H), 2.44-2.30 (m, 1H), 2.12 (d, J=6.73 Hz, 2H), 1.85-1.63 (m, 5H), 1.50-1.32 (m, 2H), 1.17-0.99 (m, 2H).
No. 72
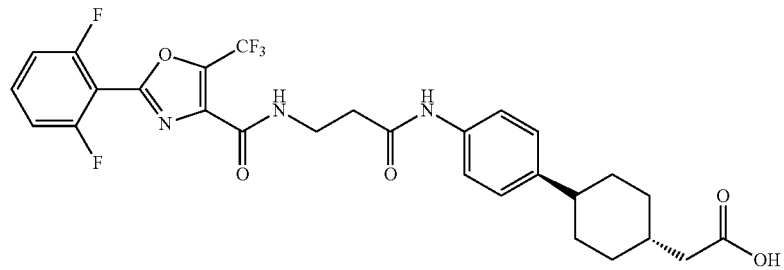
¹H NMR (300 MHz, DMSO-d₆): 12.07 (s, 1H), 9.91 (s, 1H), 8.74 (t, J=6.071H), 7.84-7.61 (m, 1H), 7.47 (d, J=7.69 Hz, 2H), 7.44-7.35 (m, 1H), 7.13 (d, J=7.69 Hz, 2H), 7.09-6.98 (m, 1H), 3.62-3.48 (m, 2H), 2.66-2.56 (m, 2H), 2.45-2.31 (m, 1H), 2.12 (d, J=6.75 Hz, 2H), 1.85-1.61 (m, 5H), 1.51-1.32 (m, 2H), 1.77-0.98 (m, 2H).

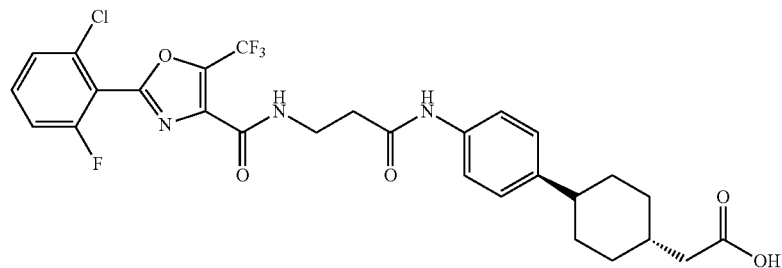
No. 73
$^1$H NMR (300 MHz, DMSO-d$_6$): 12.03 (s, 1H), 9.90 (s, 1H), 8.86 (t, J=5.32 Hz, 1H), 7.83-7.72 (m, 1H), 7.63 (d, J=8.09 Hz, 1H), 7.54 (t, J=9.14 Hz, 1H), 7.47 (d, J=8.34 Hz, 2H), 7.12 (d, J=8.39 Hz, 2H), 3.55 (q, J=6.60 Hz, 2H), 2.61 (t, J=6.77 Hz, 2H), 2.44-2.31 (m, 1H), 2.12 (d, J=6.90 Hz, 2H), 1.85-1.61 (m, 5H), 1.49-1.31 (m, 2H), 1.17-0.99 (m, 2H).
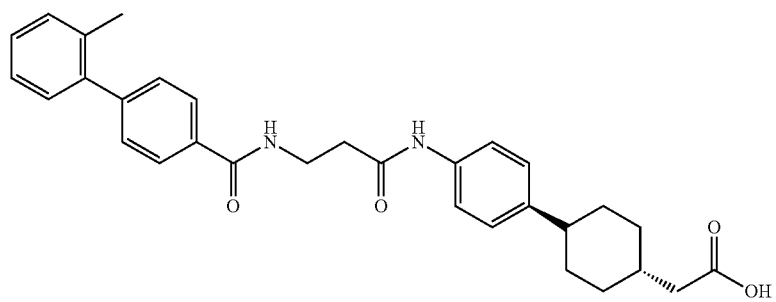
No. 74
$^1$H NMR (300 MHz, DMSO-d$_6$): 12.03 (s, 1H), 9.89 (s, 1H), 8.64 (t, J=5.91 Hz, 1H), 7.90 (d, J=8.28 Hz, 2H), 7.49 (d, J=8.15 Hz, 2H), 7.41 (d, J=8.28 Hz, 2H), 7.35-7.18 (m, 4H), 7.13 (d, J=8.37 Hz, 2H), 3.62-3.51 (m, 2H), 2.61 (t, J=6.71 Hz, 2H), 2.45-2.32 (m, 1H), 2.20 (s, 3H), 2.12 (d, J=6.82 Hz, 2H), 1.86-1.61 (m, 5H), 1.50-1.32 (m, 2H), 1.20-0.99 (m, 2H).
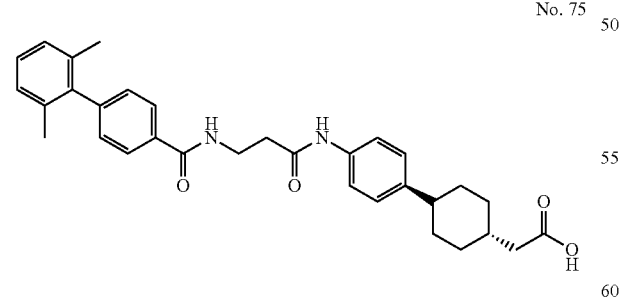
No. 75
$^1$H NMR (300 MHz, DMSO-d$_6$): 12.03 (s, 1H), 9.90 (s, 1H), 8.64 (t, J=5.04 Hz, 1H), 7.91 (d, J=8.28 Hz, 2H), 7.50 (d, J=8.53 Hz, 2H), 7.22 (d, J=8.15 Hz, 2H), 7.19-7.08 (m, 5H), 3.62-3.51 (m, 2H), 2.61 (t, J=6.91 Hz, 2H), 2.45-2.31 (m, 1H), 2.12 (d, J=6.76 Hz, 2H), 1.95 (s, 6H), 1.85-1.61 (m, 5H), 1.50-1.32 (m, 2H), 1.18-1.00 (m, 2H).

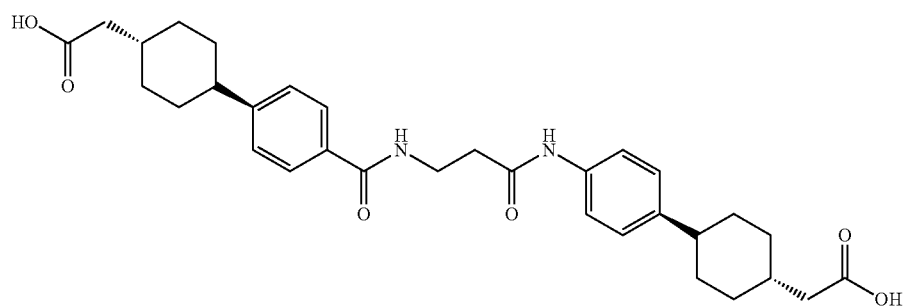
No. 76
¹H NMR (300 MHz, DMSO-d₆): 12.05 (s, 2H), 9.87 (s, 1H), 8.49 (t, J=5.17 Hz, 1H), 7.74 (d, J=8.24 Hz, 2H), 7.48 (d, J=8.24 Hz, 2H), 7.29 (d, J=7.98 Hz, 2H), 7.12 (d, J=8.29 Hz, 2H), 3.56-3.45 (m, 2H), 2.57 (t, J=7.00 Hz, 2H), 2.43-2.30 (m, 2H), 2.18-2.06 (m, 4H), 1.89-1.61 (m, 10H), 1.56-1.31 (m, 4H), 1.20-0.97 (m, 4H).
No. 77
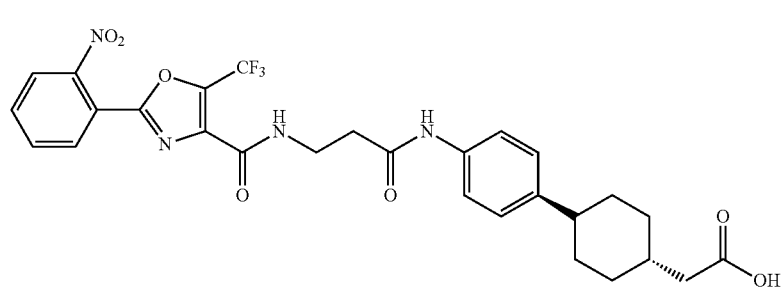
¹H NMR (300 MHz, DMSO-d₆): 12.03 (s, 1H), 9.90 (s, 1H), 8.83-8.76 (m, 1H), 8.25-8.20 (m, 1H), 8.12-8.06 (m, 1H), 7.99-7.93 (m, 2H), 7.45 (d, J=8.49 Hz, 2H), 7.13 (d, J=8.64 Hz, 2H), 3.60-3.50 (m, 2H), 2.61 (t, J=7.03 Hz, 2H), 2.44-2.30 (m, 1H), 2.11 (d, J=6.84 Hz, 2H), 1.84-1.62 (m, 5H), 1.50-1.31 (m, 2H), 1.17-0.99 (m, 2H).
No. 78
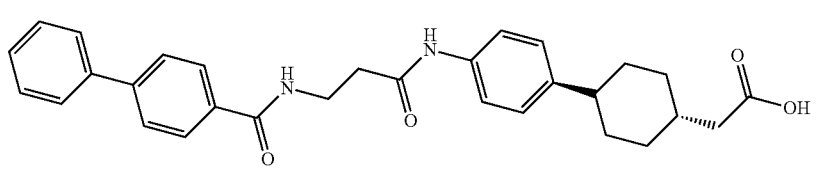
¹H NMR (300 MHz, DMSO-d₆): 12.04 (s, 1H), 9.89 (s, 1H), 8.65 (t, J=5.32 Hz, 1H), 7.93 (d, J=8.24 Hz, 2H), 7.75 (d, J=8.58 Hz, 2H), 7.72 (d, J=7.72 Hz, 2H), 7.53-7.44 (m, 4H), 7.43-7.36 (m, 1H), 7.13 (d, J=8.58 Hz, 2H), 3.63-3.49 (m, 2H), 2.61 (t, J=6.89 Hz, 2H), 2.44-2.31 (m, 1H), 2.12 (d, J=6.89 Hz, 2H), 1.84-1.62 (m, 5H), 1.50-1.32 (m, 2H), 1.17-0.99 (m, 2H).
No. 79
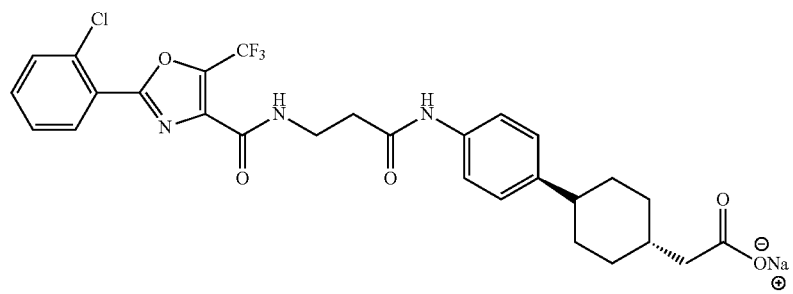

¹H NMR (300 MHz, DMSO-d₆): 10.19 (s, 1H), 8.89 (t, J=6.19 Hz, 1H), 8.06 (dd, J=7.66, 1.02 Hz, 1H), 7.74-7.61 (m, 2H), 7.61-7.53 (m, 1H), 7.49 (d, J=8.42 Hz, 2H), 7.09 (d, J=8.38 Hz, 2H), 3.62-3.51 (m, 2H), 2.64 (t, J=7.17 Hz, 2H), 2.40-2.25 (m, 1H), 1.87-1.56 (m, 7H), 1.44-1.24 (m, 2H), 1.05-0.86 (m, 2H).
¹H NMR (300 MHz, DMSO-d₆): 12.08 (s, 2H), 9.86 (s, 1H), 8.41 (t, J=5.83 Hz, 1H), 7.78 (d, J=8.57 Hz, 2H), 7.48 (d, J=8.23 Hz, 2H), 7.12 (d, J=8.40 Hz, 2H), 6.97 (d, J=8.57 Hz, 2H), 4.64-4.50 (m, 1H), 3.56-3.45 (m, 2H), 2.57 (t, J=7.03 Hz, 2H), 2.44-2.30 (m, 2H), 2.12 (d, J=6.68 Hz, 2H), 1.86-1.58 (m, 13H), 1.49-1.32 (m, 2H), 1.19-0.99 (m, 2H).
No. 80
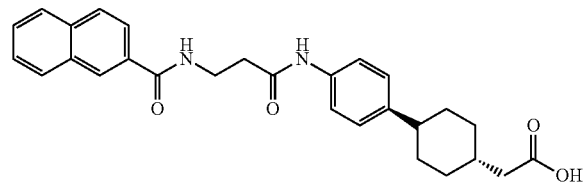
No. 83
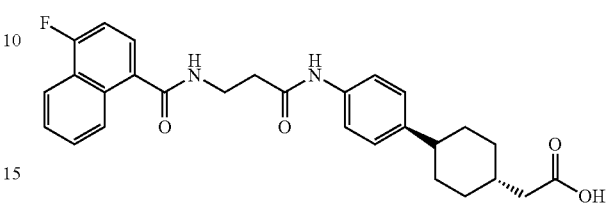
¹H NMR (300 MHz, DMSO-d₆): 12.04 (s, 1H), 9.90 (s, 1H), 8.76 (t, J=5.89 Hz, 1H), 8.43 (s, 1H), 8.02-7.88 (m, 4H), 7.64-7.54 (m, 2H), 7.49 (d, J=8.25 Hz, 2H), 7.13 (d, J=8.39 Hz, 2H), 3.65-3.55 (m, 2H), 2.64 (t, J=6.68 Hz, 2H), 2.45-2.31 (m, 1H), 2.12 (d, J=6.68 Hz, 2H), 1.85-1.64 (m, 5H), 1.50-1.32 (m, 2H), 1.18-0.99 (m, 2H).
¹H NMR (300 MHz, DMSO-d₆): 12.13 (s, 1H), 9.94 (s, 1H), 8.70-8.63 (m, 1H), 8.28 (d, J=8.27 Hz, 1H), 8.09 (d, J=8.04 Hz, 1H), 7.70-7.54 (m, 3H), 7.51 (d, J=8.27 Hz, 2H), 7.41-7.32 (m, 1H), 7.14 (d, J=8.19 Hz, 2H), 3.65-3.55 (m, 2H), 2.65 (t, J=6.73 Hz, 2H), 2.45-2.32 (m, 1H), 2.12 (d, J=6.81 Hz, 2H), 1.86-1.61 (m, 5H), 1.52-1.33 (m, 2H), 1.20-1.00 (m, 2H).
No. 81
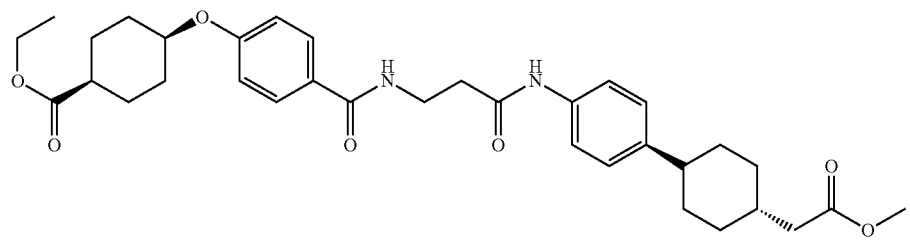
LC-MS (m/z): 593 (MH⁺)
No. 82
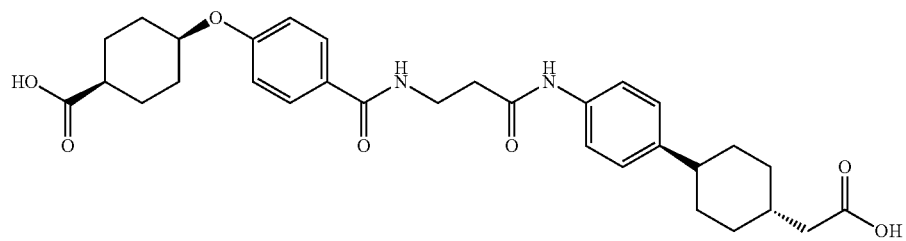

No. 84
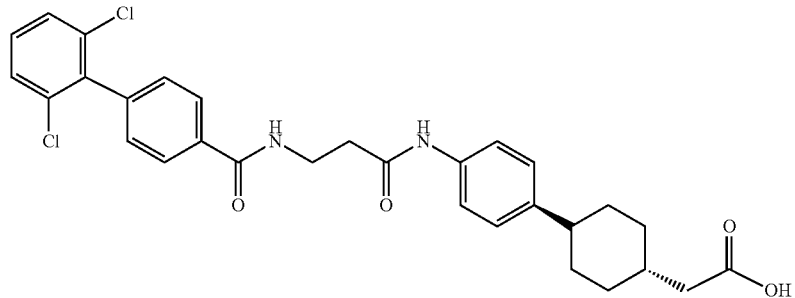
¹H NMR (300 MHz, DMSO-d₆): 12.08 (s, 1H), 9.90 (s, 1H), 8.70 (t, J=5.75 Hz, 1H), 7.93 (d, J=8.18 Hz, 2H), 7.60 (d, J=8.31 Hz, 2H), 7.53-7.41 (m, 3H), 7.35 (d, J=8.18 Hz, 2H), 7.13 (d, J=8.18 Hz, 2H), 3.62-3.51 (m, 2H), 2.61 (t, J=7.16 Hz, 2H), 2.45-2.31 (m, 1H), 2.12 (d, J=6.90 Hz, 2H), 1.86-1.64 (m, 5H), 1.49-1.32 (m, 2H), 1.18-1.00 (m, 2H).
No. 85
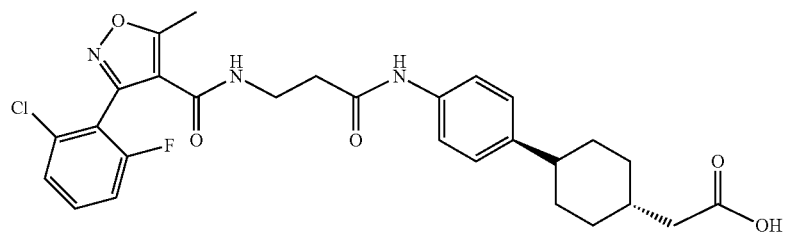
¹H NMR (300 MHz, DMSO-d₆): 12.03 (s, 1H), 9.87 (s, 1H), 8.15 (t, J=5.93 Hz, 1H), 7.60-7.30 (m, 5H), 7.13 (d, J=8.18 Hz, 2H), 3.44-3.29 (m, 2H), 2.60 (s, 3H), 2.53-2.46 (m, 2H), 2.45-2.32 (m, 1H), 2.13 (d, J=6.61 Hz, 2H), 1.86-1.62 (m, 5H), 1.50-1.33 (m, 2H), 1.21-0.99 (m, 2H).
No. 86
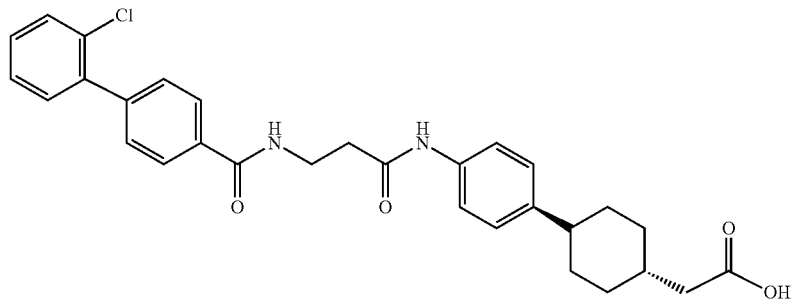
¹H NMR (300 MHz, DMSO-d₆): 12.02 (s, 1H), 9.89 (s, 1H), 8.67 (t, J=5.89 Hz, 1H), 7.91 (d, J=8.05 Hz, 2H), 7.62-7.39 (m, 8H), 7.13 (d, J=8.52 Hz, 2H), 3.61-3.51 (m, 2H), 2.61 (t, J=6.87 Hz, 2H), 2.45-2.32 (m, 1H), 2.12 (d, J=6.63 Hz, 2H), 1.85-1.62 (m, 5H), 1.50-1.32 (m, 2H), 1.18-0.99 (m, 2H).
No. 87
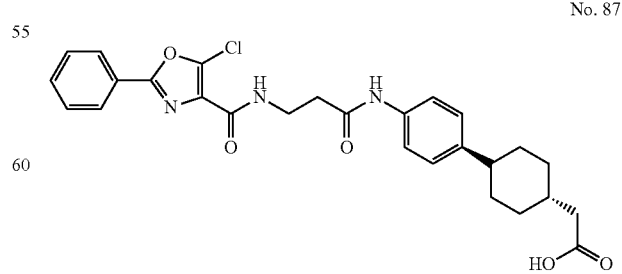
¹H NMR (300 MHz, DMSO-d₆): 12.05 (s, 1H), 9.90 (s, 1H), 8.42 (t, J=6.66 Hz, 1H), 8.01-7.94 (m, 2H), 7.62-7.55 (m, 3H), 7.48 (d, J=8.61 Hz, 2H), 7.13 (d, J=8.34 Hz, 2H), 3.60-3.49 (m, 2H), 2.61 (t, J=6.83 Hz, 2H), 2.45-2.32 (m, 1H), 2.12 (d, J=7.10 Hz, 2H), 1.85-1.66 (m, 5H), 1.50-1.32 (m, 2H), 1.20-1.00 (m, 2H).
No. 88
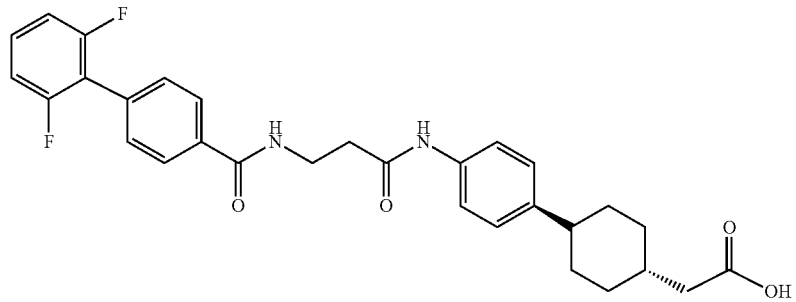
¹H NMR (300 MHz, DMSO-d₆): 12.02 (s, 1H), 9.89 (s, 1H), 8.77-8.62 (m, 1H), 7.93 (d, J=7.12 Hz, 2H), 7.64-7.40 (m, 5H), 7.32-7.06 (m, 4H), 3.65-3.48 (m, 2H), 2.61 (t, J=6.80 Hz, 2H), 2.43-2.29 (m, 1H), 2.12 (d, J=6.73 Hz, 2H), 1.91-1.60 (m, 5H), 1.54-1.31 (m, 2H), 1.20-0.98 (m, 2H).
No. 89
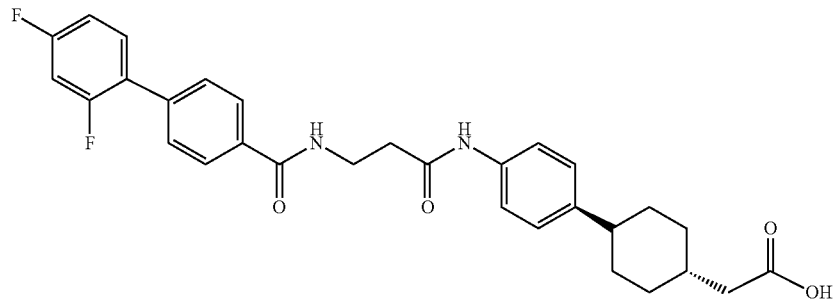
¹H NMR (300 MHz, DMSO-d₆): 12.04 (s, 1H), 9.89 (s, 1H), 8.68 (t, J=5.54 Hz, 1H), 7.93 (d, J=8.31 Hz, 2H), 7.78-7.57 (m, 3H), 7.49 (d, J=8.31 Hz, 2H), 7.45-7.34 (m, 1H), 7.26-7.17 (m, 1H), 7.13 (d, J=8.31 Hz, 2H), 3.62-3.50 (m, 2H), 2.61 (t, J=6.83 Hz, 2H), 2.45-2.31 (m, 1H), 2.12 (d, J=6.83 Hz, 2H), 1.82-1.62 (m, 5H), 1.50-1.32 (m, 2H), 1.18-0.99 (m, 2H).
No. 90
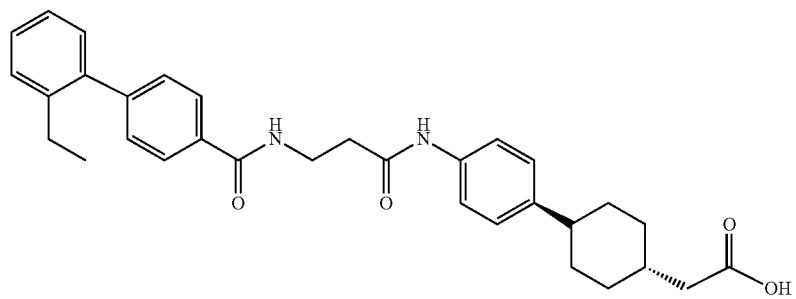
¹H NMR (300 MHz, DMSO-d₆): 12.00 (s, 1H), 9.89 (s, 1H), 8.64 (t, J=5.86 Hz, 1H), 7.89 (d, J=8.20 Hz, 2H), 7.49 (d, J=8.43 Hz, 2H), 7.43-7.31 (m, 4H), 7.29-7.21 (m, 1H), 7.19-7.09 (m, 3H), 3.62-3.52 (m, 2H), 2.66-2.55 (m, 4H), 2.44-2.30 (m, 1H), 2.12 (d, J=6.62 Hz, 2H), 1.86-1.64 (m, 5H), 1.50-1.32 (m, 2H), 1.17-1.05 (m, 2H), 1.01 (t, J=7.61 Hz, 3H).

No. 91
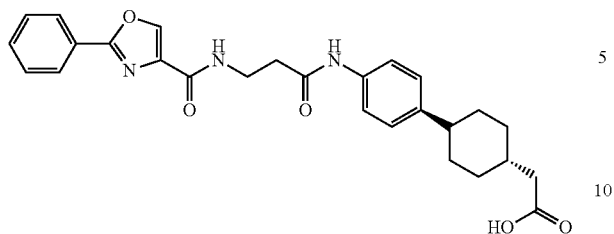
¹H NMR (300 MHz, DMSO-d₆): 12.04 (s, 1H), 9.91 (s, 1H), 8.71 (s, 1H), 8.36 (t, J=5.66 Hz, 1H), 8.06-7.97 (m, 2H), 7.61-7.54 (m, 3H), 7.48 (d, J=8.49 Hz, 2H), 7.13 (d, J=8.63 Hz, 2H), 3.60-3.50 (m, 2H), 2.61 (t, J=6.74 Hz, 2H), 2.45-2.32 (m, 1H), 2.12 (d, J=6.88 Hz, 2H), 1.85-1.62 (m, 5H), 1.49-1.32 (m, 2H), 1.17-0.99 (m, 2H).
No. 92
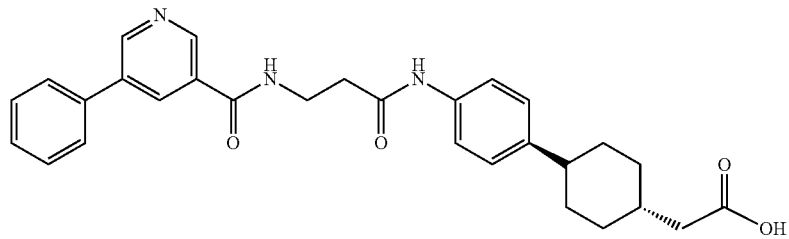
¹H NMR (300 MHz, DMSO-d₆): 12.00 (s, 1H), 9.91 (s, 1H), 9.01 (d, J=2.17 Hz, 1H), 8.98-8.88 (m, 2H), 8.43 (s, 1H), 7.78 (d, J=7.10 Hz, 2H), 7.57-7.41 (m, 5H), 7.12 (d, J=8.40 Hz, 2H), 3.64-3.53 (m, 2H), 2.62 (t, J=7.18 Hz, 2H), 2.45-2.31 (m, 1H), 2.12 (d, J=6.80 Hz, 2H), 1.85-1.62 (m, 5H), 1.49-1.31 (m, 2H), 1.19-0.99 (m, 2H).
No. 93
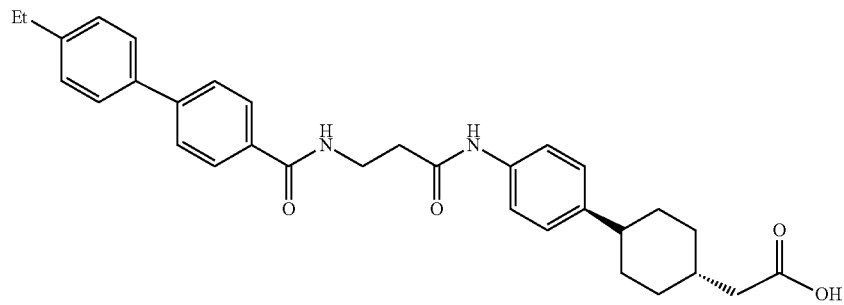
¹H NMR (300 MHz, DMSO-d₆): 12.03 (s, 1H), 9.93 (s, 1H), 8.65 (t, J=5.46 Hz, 1H), 7.92 (d, J=8.30 Hz, 2H), 7.73 (d, J=8.35 Hz, 2H), 7.63 (d, J=8.09 Hz, 2H), 7.50 (d, J=8.38 Hz, 2H), 7.31 (d, J=8.26 Hz, 2H), 7.13 (d, J=8.46 Hz, 2H), 3.61-3.50 (m, 2H), 2.70-2.56 (m, 4H), 2.45-2.30 (m, 1H), 2.12 (d, J=6.72 Hz, 2H), 1.85-1.61 (m, 5H), 1.50-1.32 (m, 2H), 1.20 (t, J=7.53 Hz, 3H), 1.16-0.99 (m, 2H).

No. 94
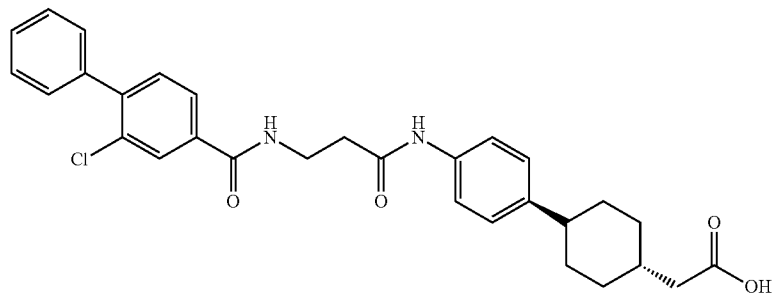
¹H NMR (300 MHz, DMSO-d$_6$): 12.03 (s, 1H), 9.89 (s, 1H), 8.79 (t, J=6.19 Hz, 1H), 8.01 (d, J=1.34 Hz, 1H), 7.87 (dd, J=8.21, 1.15 Hz, 1H), 7.54-7.39 (m, 8H), 7.13 (d, J=8.28 Hz, 2H), 3.62-3.50 (m, 2H), 2.61 (t, J=6.85 Hz, 2H), 2.45-2.30 (m, 1H), 2.12 (d, J=6.91 Hz, 2H), 1.85-1.62 (m, 5H), 1.50-1.32 (m, 2H), 1.20-0.99 (m, 2H).
No. 95
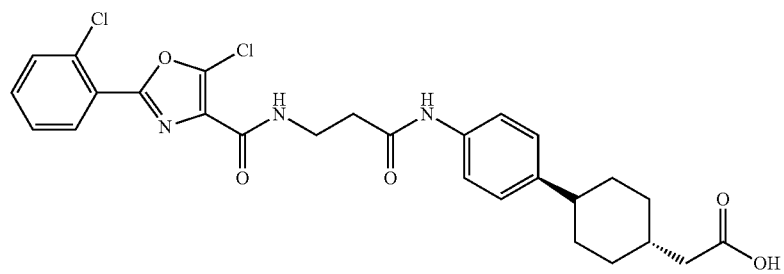
¹H NMR (300 MHz, DMSO-d$_6$): 12.00 (s, 1H), 9.90 (s, 1H), 8.42 (t, J=6.46 Hz, 1H), 7.98 (dd, J=7.64, 1.79 Hz, 1H), 7.72-7.51 (m, 3H), 7.47 (d, J=8.58 Hz, 2H), 7.13 (d, J=8.39 Hz, 2H), 3.59-3.48 (m, 2H), 2.60 (t, J=7.02 Hz, 2H), 2.44-2.31 (m, 1H), 2.12 (d, J=6.63 Hz, 2H), 1.86-1.59 (m, 5H), 1.50-1.31 (m, 2H), 1.20-0.98 (m, 2H).
No. 96
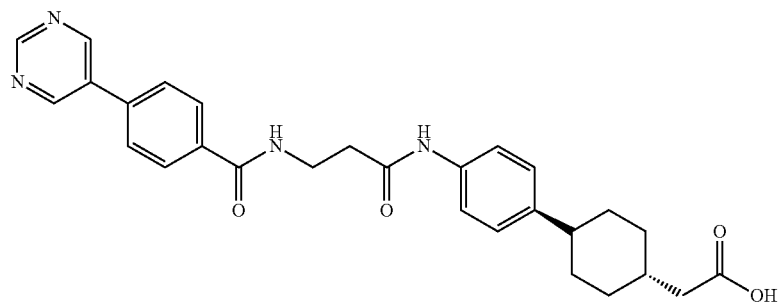

¹H NMR (300 MHz, DMSO-d₆): 12.04 (s, 1H), 9.90 (s, 1H), 8.66 (t, J=5.50 Hz, 1H), 7.93 (d, J=8.17 Hz, 2H), 7.79-7.68 (m, 3H), 7.53-7.44 (m, 3H), 7.44-7.35 (m, 1H), 7.13 (d, J=8.39 Hz, 2H), 3.61-3.50 (m, 2H), 2.61 (t, J=6.94 Hz, 2H), 2.45-2.31 (m, 1H), 2.12 (d, J=6.69 Hz, 2H), 1.85-1.61 (m, 5H), 1.51-1.31 (m, 2H), 1.19-0.99 (m, 2H).
No. 97
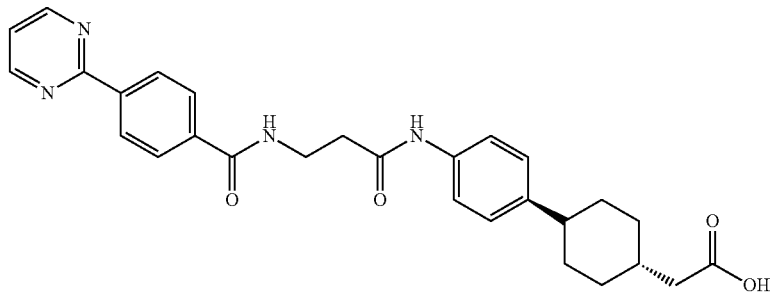
¹H NMR (300 MHz, DMSO-d₆): 12.04 (s, 1H), 9.90 (s, 1H), 8.94 (dd, J=4.87, 0.49 Hz, 2H), 8.78-8.70 (m, 1H), 8.45 (d, J=8.21 Hz, 2H), 7.98 (d, J=8.32 Hz, 2H), 7.53-7.45 (m, 3H), 7.13 (d, J=8.43 Hz, 2H), 3.63-3.51 (m, 2H), 2.61 (t, J=6.75 Hz, 2H), 2.44-2.43 (m, 1H), 2.12 (d, J=6.75 Hz, 2H), 1.85-1.62 (m, 5H), 1.51-1.30 (m, 2H), 1.19-0.97 (m, 2H).
No. 98
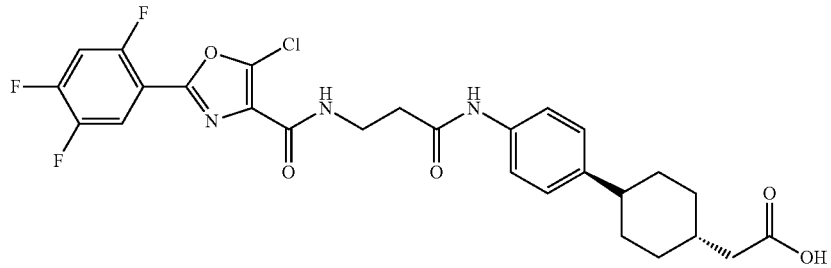
¹H NMR (300 MHz, DMSO-d₆): 12.02 (s, 1H), 9.90 (s, 1H), 8.48-8.35 (m, 1H), 7.88-7.73 (m, 1H), 7.48 (d, J=8.56 Hz, 2H), 7.44-7.34 (m, 1H), 7.13 (d, J=8.71 Hz, 2H), 3.59-3.48 (m, 2H), 2.60 (t, J=6.97 Hz, 2H), 2.44-2.30 (m, 1H), 2.12 (d, J=6.82 Hz, 2H), 1.85-1.60 (m, 5H), 1.50-1.32 (m, 2H), 1.19-0.99 (m, 2H).
No. 99
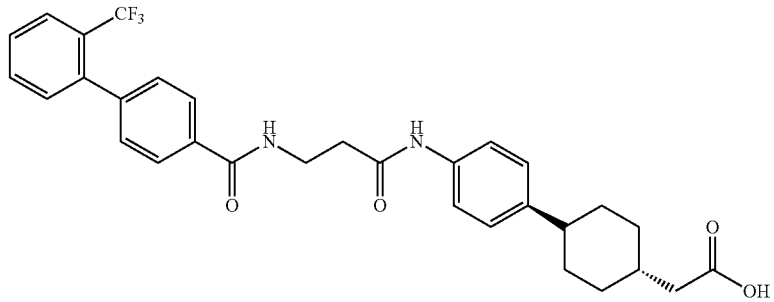

¹H NMR (300 MHz, DMSO-d₆): 12.02 (s, 1H), 9.89 (s, 1H), 8.68 (t, J=6.04 Hz, 1H), 7.93-7.81 (m, 3H), 7.74 (t, J=7.40 Hz, 1H), 7.63 (t, J=7.40 Hz, 1H), 7.49 (d, J=8.34 Hz, 2H), 7.44-7.35 (m, 3H), 7.13 (d, J=8.55 Hz, 2H), 3.63-3.51 (m, 2H), 2.61 (t, J=7.40 Hz, 2H), 2.44-2.32 (m, 1H), 2.12 (d, J=6.88 Hz, 2H), 1.86-1.62 (m, 5H), 1.50-1.32 (m, 2H), 1.18-0.99 (m, 2H).
No. 100
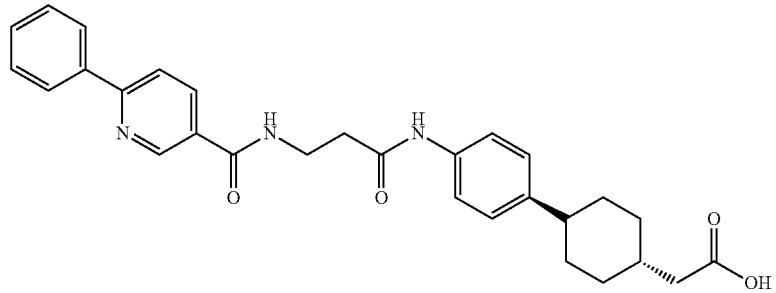
¹H NMR (300 MHz, DMSO-d₆): 12.03 (s, 1H), 9.90 (s, 1H), 9.07 (d, J=1.90 Hz, 1H), 8.84 (t, J=5.29 Hz, 1H), 8.26 (dd, J=8.54, 2.15 Hz, 1H), 8.18-8.11 (m, 2H), 8.07 (d, J=8.54 Hz, 1H), 7.56-7.44 (m, 5H), 7.13 (d, J=8.54 Hz, 2H), 3.64-3.53 (m, 2H), 2.62 (t, J=6.85 Hz, 2H), 2.45-2.31 (m, 1H), 2.12 (d, J=6.79 Hz, 2H), 1.85-1.61 (m, 5H), 1.51-1.31 (m, 2H), 1.20-0.98 (m, 2H).
No. 101
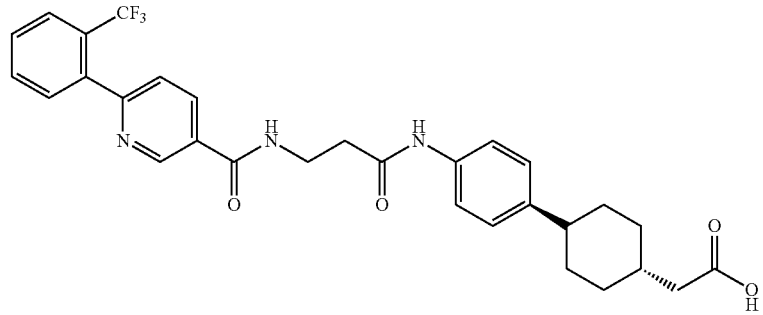
¹H NMR (300 MHz, DMSO-d₆): 12.05 (s, 1H), 9.91 (s, 1H), 9.04 (d, J=2.02 Hz, 1H), 8.91 (t, J=5.55 Hz, 1H), 8.27 (dd, J=8.27, 1.76 Hz, 1H), 7.88 (d, J=7.38 Hz, 1H), 7.83-7.66 (m, 2H), 7.64-7.53 (m, 2H), 7.49 (d, J=8.48 Hz, 2H), 7.13 (d, J=8.58 Hz, 2H), 3.64-3.53 (m, 2H), 2.62 (t, J=6.51 Hz, 2H), 2.44-2.31 (m, 1H), 2.12 (d, J=6.80 HZ, 2H), 1.86-1.60 (m, 5H), 1.50-1.31 (m, 2H), 1.18-0.98 (m, 2H).
No. 102
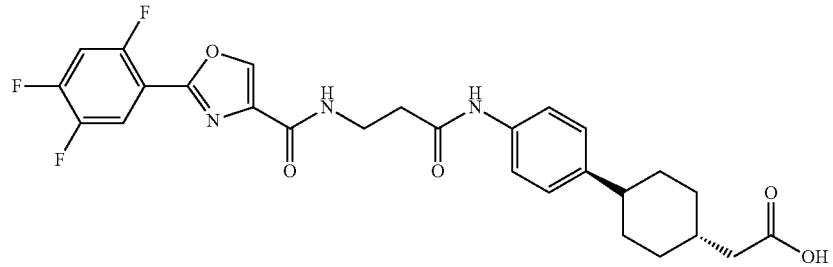

¹H NMR (300 MHz, DMSO-d₆): 12.03 (s, 1H), 9.91 (s, 1H), 8.81 (s, 1H), 8.39 (t, J=6.27 Hz, 1H), 8.14-8.02 (m, 1H), 7.93-7.79 (m, 1H), 7.48 (d, J=8.20 Hz, 2H), 7.13 (d, J=8.57 Hz, 2H), 3.60-3.49 (m, 2H), 2.60 (t, J=6.56 Hz, 2H), 2.44-2.29 (m, 1H), 2.12 (d, J=6.68 Hz, 2H), 1.85-1.62 (m, 5H), 1.51-1.31 (m, 2H), 1.16-0.99 (m, 2H).

Experimental Example 1

Zymogen

A plasmid (Origene #RC220595) in which cDNA coding the full-length of human DGAT1 was inserted into a mam- No. 103

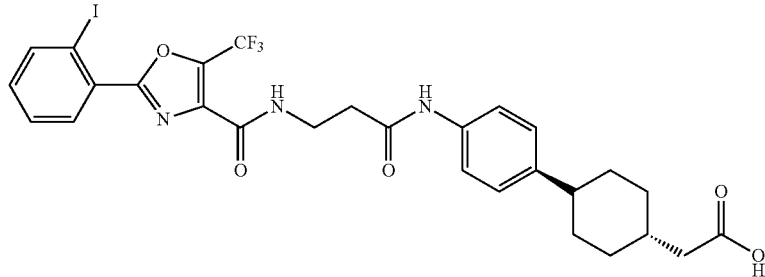

¹H NMR (300 MHz, DMSO-d₆): 12.02 (s, 1H), 9.92 (s, 1H), 8.78 (t, J=5.85 Hz, 1H), 8.11 (d, J=7.68 Hz, 1H), 7.88 (dd, J=8.03, 1.53 Hz, 1H), 7.66-7.57 (m, 1H), 7.47 (d, J=8.30 Hz, 2H), 7.42-7.33 (m, 1H), 7.13 (d, J=8.30 Hz, 2H), 3.61-3.49 (m, 2H), 2.62 (t, J=7.58 Hz, 2H), 2.45-2.30 (m, 1H), 2.12 (d, J=6.67 Hz, 2H), 1.85-1.61 (m, 5H), 1.50-1.31 (m, 2H), 1.19-0.99 (m, 2H).

malian cell expression vector pCMV6 was introduced into a Hep3B cell using a lipofectamine agent (Invitrogen) for 5 hours according to manufacturer's instruction, and the cell was stabilized for 48 hours. The cells were treated with 200 μg/ml G-418(Sigma) once every three days for 4 weeks to over-express the human DGAT1, thereby obtaining a stabilized cell line. The over-expressed cells were put into a No. 104

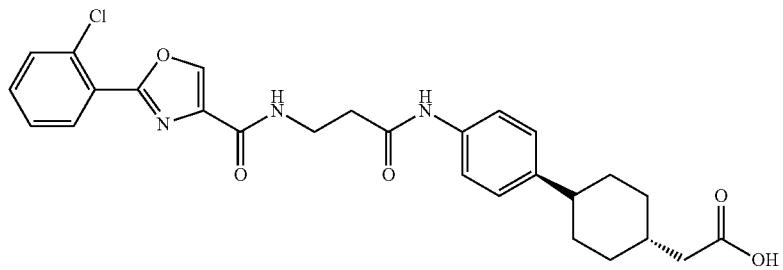

¹H NMR (300 MHz, DMSO-d₆): 12.03 (s, 1H), 9.90 (s, 1H), 8.80 (s, 1H), 8.37 (t, J=5.85 Hz, 1H), 7.98 (dd, J=7.39, 1.53 Hz, 1H), 7.71-7.51 (m, 3H), 7.47 (d, J=8.36 Hz, 2H), 7.13 (d, J=8.23 Hz, 2H), 3.62-3.48 (m, 2H), 2.60 (t, J=6.97 Hz, 2H), 2.44-2.29 (m, 1H), 2.12 (d, J=6.27 Hz, 2H), 1.86-1.59 (m, 5H), 1.51-1.30 (m, 2H), 1.21-0.97 (m, 2H).

homogenization buffer [250 mM sucrose, 10 mM Tris-HCl (pH 7.4), 1 mM EDTA] and lysed by a homogenization apparatus. Then, centrifugation was performed with 600×g for 15 minutes to remove cell residue, and the obtained cells were used for an enzyme inhibition test.

No. 105

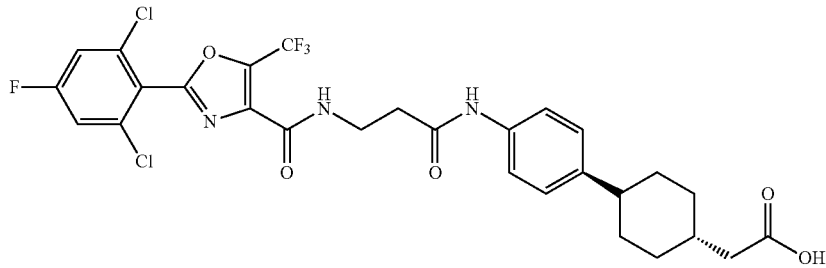

LC-MS (m/z): 630 (MH⁺)

Enzyme Inhibition Test

Human DGAT-1 and mouse DGAT activity was determined as follows: Assay buffer [20 mM HEPES (pH 7.4), 100 mM $MgCl_2$, 0.04% BSA] containing 500 μM of enzyme substrate (didecanoyl glycerol) and 7.5 μM radiolabeled acyl-CoA substrate ([$^{14}$C]decanoyl-CoA) was added to each well of a phospholipid FlashPlate (PerkinElmer Life Sciences). A small aliquot of lysate (5 μg/well) or mouse liver microsome (0.1 mg/well) was added to start the reaction, which was allowed to proceed in a 20° C. bath for 1 hour. and maintained overnight at room temperature. Next day, measurement was performed by Wallac 1450 Microbeta Trilux Liquid Scintillation Counter and Luminometer (PerkinElmer Life Science). In the control group, 0.1% DMSO was only added, and for the background value, 0.1% DMSO was only added without the cell fragment having the over-expressed human DGAT1 (5 μg/well) or the liver microsome of mice (0.1 mg/well), which was the same as the control group. A calculation method of inhibition degree (%) is as follows.

Inhibition degree(%)=100−((cpm value of drug−cpm value of background)/(cpm value of control group−cpm value of background)×100)

As a result after the measurement, $IC_{50}$ values of the compounds of the present invention decreasing human DGAT1 enzyme activity to 50% are shown in the following Table 1.

TABLE 1

| Compound No | Human DGAT1 $IC_{50}$ (nM) |
|---|---|
| 4 | <50 nM |
| 6 | <50 nM |
| 7 | <100 nM |
| 11 | <50 nM |
| 15 | <100 nM |
| 19 | <100 nM |
| 21 | <100 nM |
| 22 | <500 nM |
| 27 | <100 nM |
| 31 | <100 nM |
| 33 | <500 nM |
| 37 | <100 nM |
| 41 | <50 nM |
| 47 | <100 nM |
| 49 | <100 nM |
| 51 | <100 nM |
| 56 | <500 nM |
| 58 | <500 nM |
| 60 | <50 nM |
| 64 | <50 nM |
| 65 | <50 nM |
| 66 | <50 nM |
| 68 | <50 nM |
| 69 | <50 nM |
| 73 | <100 nM |
| 75 | <100 nM |
| 79 | <50 nM |
| 86 | <100 nM |
| 87 | <100 nM |
| 93 | <50 nM |
| 94 | <50 nM |
| 95 | <50 nM |
| 105 | <50 nM |

As shown in Table 1, the compounds of 4, 6, 11, 41, 60, 64, 65, 66, 68, 69, 79, 93, 94, 95 and 105, which is the beta-alanine derivative compound, showed good to excellent in vitro inhibition activity with respect to DGAT1.

Although specific embodiments of the present invention are described in detail, it will be apparent to those skilled in the art that the specific description is merely desirable exemplary embodiment and should not be construed as limiting the scope of the present invention. Therefore, the substantial scope of the present invention is defined by the accompanying claims and equivalent thereof.

The invention claimed is:

1. A beta-alanine derivative represented by the following Chemical Formula 1 or pharmaceutically acceptable salts thereof:

[Chemical Formula 1]

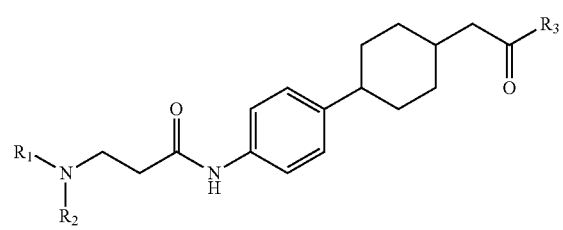

in Chemical Formula 1,
$R_1$ and $R_2$ are each independently hydrogen, a $C_1$-$C_{10}$ alkyl group, a $C_3$-$C_7$ cycloalkyl group or

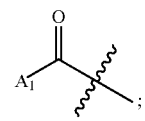

$A_1$ is a substituted or unsubstituted $C_1$-$C_7$ alkyl group, a substituted or unsubstituted $C_3$-$C_7$ cycloalkyl group, a substituted or unsubstituted $C_1$-$C_7$ alkoxy group, a substituted or unsubstituted $C_5$-$C_{20}$ aryl $C_1$-$C_7$ alkyl, a substituted or unsubstituted $C_5$-$C_{20}$ aryl group or a $C_3$-$C_{20}$ heteroaryl group containing 1 to 3 heteroatoms each independently selected from oxygen, nitrogen and sulfur;
$R_3$ is $OR_{30}$, or a substituted or unsubstituted amine group; and
$R_{30}$ is hydrogen or $C_1$-$C_5$ alkyl.

2. The beta-alanine derivative or pharmaceutically acceptable salts thereof of claim 1, wherein $R_1$ and $R_2$ are each independently hydrogen or

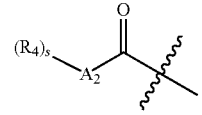

$A_2$ is a $C_1$-$C_7$ alkylene group, a $C_3$-$C_7$ cycloalkylene group, a $C_5$-$C_{20}$ aryl $C_1$-$C_7$ alkyl, a $C_5$-$C_{20}$ arylene group or a $C_3$-$C_{20}$ heteroarylene group containing 1 to 3 heteroatoms each independently selected from oxygen, nitrogen and sulfur;
$R_4$ is selected from the group consisting of hydrogen, halogen, a substituted or unsubstituted $C_1$-$C_7$ alkyl group, a substituted or unsubstituted $C_3$-$C_7$ cycloalkyl group, a substituted or unsubstituted $C_1$-$C_7$ alkoxy group, a substituted or unsubstituted amino group, a substituted or unsubstituted $C_5$-$C_{20}$ aryl group and a substituted or unsubstituted $C_3$-$C_{20}$ heteroaryl group containing 1 to 2 or more heteroatoms in which the heteroatoms are selected from the group consisting of oxygen, nitrogen and sulfur; and
s is an integer of 0 to 3.

3. The beta-alanine derivative or pharmaceutically acceptable salts thereof of claim 2, wherein $A_2$ is phenylene, naphthylene, benzylene, pyridylene, pryimidinylene, triazinylene, oxazolene, pyrazolene, oxadizolene, thiazolene, or indolene.

4. The beta-alanine derivative or pharmaceutically acceptable salts thereof of claim 2, wherein $R_4$ is further substituted with at least one substituent independently selected from halogen, a substituted or unsubstituted $C_1$-$C_7$ alkyl group, a carboxyl group, a substituted or unsubstituted $C_1$-$C_7$alkylcarbonyl group, a substituted or unsubstituted $C_1$-$C_7$ alkoxy group; a substituted or unsubstituted $C_3$-$C_7$ cycloalkyl group, a $C_1$-$C_7$ alkoxycarbonyl group, a carboxy $C_1$-$C_7$ alkyl group, a substituted or unsubstituted $C_5$-$C_{20}$ aryl group, a substituted or unsubstituted $C_3$-$C_{20}$ heteroaryl group containing 1 to 2 or more heteroatoms selected from oxygen, nitrogen and sulfur, a nitro group, and an amino group.

5. The beta-alanine derivative or pharmaceutically acceptable salts thereof of claim 1, wherein the beta-alanine derivative is selected from the group consisting of:
1) trans-(4-{4-[3-(3,4-diethoxybenzoylamino)propionylamino]phenyl}cyclohexyl)acetic acid methyl ester;
2) trans-(4-{4-[3-(3,4-diethoxybenzoylamino)propionylamino]phenyl}cyclohexyl)acetic acid;
3) trans-(4-{4-[3-(4-ethoxybenzoylamino)propionylamino]phenyl}cyclohexyl)acetic acid methyl ester;
4) trans-(4-{4-[3-(4-ethoxybenzoylamino)propionylamino]phenyl)cyclohexyl}acetic acid;
5) trans-[4-(4-{3-[(2-phenyl-5-trifluoromethyloxazole-4-carbonyl)amino]propionylamino}phenyl)cyclohexyl]acetic acid methyl ester;
6) trans-[4-(4-{3-[(2-Phenyl-5-trifluoromethyloxazole-4-carbonyl)amino]propionylamino}phenyl)cyclohexyl]acetic acid;
7) trans-[4-(4-{3-[(1-phenyl-3-trifluoromethyl-1H-pyrazole-4-carbonyl)amino]propionylamino}phenyl)cyclohexyl]acetic acid;
8) trans-2-(4-(4-(3-(2-(2,3-dichlorophenyl)-5-(trifluoromethyl)oxazole-4-carboxamido)propanamido)phenyl)cyclohexyl)acetic acid;
9) trans-2-(4-(4-(3-(2-(2,5-dichlorophenyl)-5-(trifluoromethyl)oxazole-4-carboxamido)propanamido)phenyl)cyclohexyl)acetic acid;
10) trans-{4-[4-(3-{[2-(2-chlorophenyl)-5-trifluoromethyloxazole-4-carbonyl]amino}propionylamino)phenyl]cyclohexyl}acetic acid methyl ester;
11) trans-{4-[4-(3-{[2-(2-chlorophenyl)-5-trifluoromethyloxazole-4-carbonyl]amino}propionylamino)phenyl]cyclohexyl}acetic acid;
12) trans-{4-[4-(3-{[2-(4-chlorophenyl)-5-trifluoromethyloxazole-4-carbonyl]amino}propionylamino)phenyl]cyclohexyl}acetic acid methyl ester;
13) trans-{4-[4-(3-{[2-(4-chiorophenyl)-5-trifluoromethyloxazole-4-carbonyl]amino}propionylamino)phenyl]cyclohexyl}acetic acid;
14) trans-[4-(4-{3-[(2-phenyl-4-trifluoromethyloxazole-5-carbonyl)amino]propionylamino}phenyl)cyclohexyl]acetic acid methyl ester;
15) trans-[4-(4-{3-[(2-phenyl-4-trifluoromethyloxazole-5-carbonyl)amino]propionylamino}phenyl)cyclohexyl]acetic acid;
16) trans-[4-(4-{3-[(5-phenyl-[1,2,4]oxadiazole-3-carbonyl)amino]propionylamino}phenyl)cyclohexyl]acetic acid methyl ester;
17) trans-[4-(4-{3[(5-phenyl-[1,2,4]oxadiazole-3-carbonyl)amino]propionylamino}phenyl)cyclohexyl]acetic acid;
18) trans-[4-(4-{3-[(2-p-tolyl-5-trifluoromethyloxazole-4-carbonyl)amino]propionylamino}phenyl)cyclohexyl]acetic acid methyl ester;
19) trans-[4-(4-{3-[(2-p-tolyl-5-trifluoromethyloxazole-4-carbonyl)amino]propionylamino}phenyl)cyclohexyl]acetic acid;
20) trans-[4-(4-{3-[(2-p-tolyl-5-trifluoromethyloxazole-4-carbonyl)amino]propionylamino}phenyl)cyclohexyl]acetic acid methyl ester;
21) trans-[4-(4-{3-[(2-o-tolyl-5-trifluoromethyloxazole-4-carbonyl)amino]propionylamino}phenyl)cyclohexyl]acetic acid;
22) sodium; trans-[4-(4-{3-[(2-phenyl-5-trifluoromethyloxazole-4-carbonyl)amino]propionylamino}phenyl)cyclohexyl]acetate;
23) trans-{4-[4-(3-tert-Butoxycarbonylaminopropionylamino)phenyl]cyclohexyl}acetic acid methyl ester;
24) trans-{4-[4-(3-tert-Butoxycarbonylaminopropionylamino)phenyl]cyclohexyl}acetic acid;
25) trans-{4-[4-(3-aminopropionylamino)phenyl]cyclohexyl}acetic acid methyl ester hydrochloride;
26) trans-{4-[4-(3-{[2-(4-bromophenyl)-5-trifluoromethyloxazole-4-carbonyl]amino}propionylamino)phenyl]cyclohexyl}acetic acid methyl ester;
27) trans-{4-[4-(3-{[2-(4-bromophenyl)-5-trifluoromethyloxazole-4-carbonyl]amino}propionylamino)phenyl]cyclohexyl}acetic acid;
28) trans-[4-(4-{3-[(2-methyl-5-trifluoromethyloxazole-4-carbonyl)amino]propionylamino}phenyl)cyclohexyl]acetic acid methyl ester;
29) trans-[4-(4-{3-[(2-methyl-5-trifluoromethyloxazole-4-carbonyl)amino]propionylamino}phenyl)cyclohexyl]acetic acid;
30) trans-[4-(4-{3-[(5-methyl-2-phenyloxazole-4-carbonyl)amino]propionylamino}phenyl)cyclohexyl]acetic acid methyl ester;
31) trans-[4-(4-{3-[(5-methyl-2-phenyloxazole-4-carbonyl)amino]propionylamino}phenyl)cyclohexyl]acetic acid;
32) trans-[4-(4-{3-[(4-methyl-2-phenylthiazole-5-carbonyl)amino]propionylamino}phenyl)cyclohexyl]acetic acid methyl ester;
33) trans-[4-(4-{3-[(4-methyl-2-phenylthiazole-5-carbonyl)amino]propionylamino}phenyl)cyclohexyl]acetic acid;
34) trans-{4-[4-(3-{[2-(4-chlorophenyl)-4-methylthiazole-5-carbonyl]amino}propionylamino)phenyl]cyclohexyl}acetic acid methyl ester;
35) trans-{4-[4-(3-{[2-(4-chlorophenyl)-4-methylthiazole-5-carbonyl]amino}propionylamino)phenyl]cyclohexyl}acetic acid;
36) trans-[4-(4-{3-[(2-phenyl-4-trifluoromethylthiazole-5-carbonyl)amino]propionylamino}phenyl)cyclohexyl]acetic acid methyl ester;
37) trans-[4-(4-{3-[(2-phenyl-4-trifluoromethylthiazole-5-carbonyl)amino]propionylamino}phenyl)cyclohexyl]acetic acid;
38) trans[4-(4-{3-[(2-methoxy-4-trifluoromethylthiazole-5-carbonyl)amino]propionylamino}phenyl)cyclohexyl]acetic acid methyl ester;
39) trans[4-(4-{3-[(2-methoxy-4-trifluoromethylthiazole-5-carbonyl)amino]propionylamino}phenyl)cyclohexyl]acetic acid;
40) trans-{4-[4-(3-{[4-trifluoromethyl-2-(6-trifluoromethylpyridin-3-ylamino)thiazole-5-carbonyl]amino}propionylamino)phenyl]cyclohexyl}acetic acid;

41) trans-2-phenyl-5-trifluoromethyloxazole-4-carboxylic acid{2-[4-(4-carbamoylmethylcyclohexyl)phenylcarbamoyl]ethyl}amide;
42) trans-{4-[4-(3-{[5-(2-trifluoromethylphenyl)isoxazole-3-carbonyl]amino}propionylamino)phenyl]cyclohexyl}acetic acid methyl ester;
43) trans-{4-[4-(3-{[5-(2-trifluoromethylphenyl)isoxazole-3-carbonyl]amino}propionylamino)phenyl]cyclohexyl}acetic acid;
44) trans-[4-(4-{3-[(1-o-tolyl-3-trifluoromethyl-1H-pyrazole-4-carbonyl)amino]propionylamino}phenyl)cyclohexyl]acetic acid methyl ester;
45) trans-[4-(4-{3-[(1-o-tolyl-3-trifluoromethyl-1H-pyrazol-4-ylmethyl)amino]propionylamino}phenyl)cyclohexyl]acetic acid;
46) trans-[4-(4-{3-[(1-p-tolyl-3-trifluoromethyl-1H-pyrazole-4-carbonyl)amino]propionylamino}phenyl)cyclohexyl]acetic acid methyl ester;
47) trans-[4-(4-{3-[(1-p-tolyl-3-trifluoromethyl-1H-pyrazole-4-carbonyl)amino]propionylamino}phenyl)cyclohexyl]acetic acid;
48) trans-{4-[4-(3-{[1-(4-chlorophenyl)-3-trifluoromethyl-1H-pyrazole-4-carbonyl]amino}propionylamino)phenyl]cyclohexyl}acetic acid methyl ester;
49) trans-{4-[4-(3-{[1-(4-chlorophenyl)-3-trifluoromethyl-1H-pyrazole-4-carbonyl]amino}propionylamino)phenyl]cyclohexyl}acetic acid;
50) trans-{4-[4-(3-{[1-(2-chlorophenyl)-3-trifluoromethyl-1H-pyrazole-4-carbonyl]amino}propionylamino)phenyl]cyclohexyl}acetic acid methyl ester;
51) trans-{4-[4-(3-{[1-(2-Chlorophenyl)-3-trifluoromethyl-1H-pyrazole-4-carbonyl]amino}propionylamino)phenyl]cyclohexyl}acetic acid;
52) trans-{4-[4-(3-{[1-(4-methoxyphenyl)-3-triflurom-ethyl-1H-pyrazole-4-carbonyl]amino}propionylamino)phenyl]cyclohexyl}acetic acid methyl ester;
53) trans-{4-[4-(3-{[1-(4-methoxyphenyl)-3-trifluoromethyl-1H-pyrazole-4-carbonyl]amino}propionylamino)phenyl]cyclohexyl}acetic acid;
54) trans-[4-(4-{3-[(5-chloro-1H-indole-2-carbonyl)amino]propionylamino}phenyl)cyclohexyl]acetic acid methyl ester;
55) trans-[4-(4-{3[(5-chloro-1H-indole-2-carbonyl)amino]propionylamino}phenyl)cyclohexyl]acetic acid;
56) trans-{4-[4-(3-{[2-(4-fluorophenyl)-5-trifluoromethyloxazole-4-carbonyl]amino}propionylamino)phenyl]-cyclohexyl}-acetic acid;
57) trans-[4-(4-{3-[2-(4-trifluoromethoxyphenyl)acetylamino]propionylamino}phenyl)cyclohexyl]acetic acid;
58) trans-(4-{4-[3-(4-cyclopropylmethoxybenzoylamino)propionylamino]phenyl}cyclohexyl)acetic acid;
59) trans-{4-[4-(3-{[2-(2-Fluorophenyl)-5-trifluoromethyloxazole-4-carbonyl]amino}propionylamino)phenyl]cyclohexyl}acetic acid methyl ester;
60) trans-{4-[4-(3-{[2-(2-Fluorophenyl)-5-trifluoromethyloxazole-4-carbonyl]amino}propionylamino)phenyl]cyclohexyl}acetic acid;
61) trans-(4-{4-[3-(4-chlorobenzoylamino)propionylamino]phenyl}cyclohexyl)acetic acid methyl ester;
62) trans-(4-{4-[3-(4-chlorobenzoylamino)propionylamino]phenyl}cyclohexyl)acetic acid;
63) trans-{4-[4-(3-{[2-(2,4-dichlorophenyl)-5-trifluoromethyloxazole-4-carbonyl]amino}propionylamino)phenyl]cyclohexyl}acetic acid methyl ester;
64) trans-{4-[4-(3-{[2-(2,4-dichlorophenyl)-5-trifluoromethyloxazole-4-carbonyl]amino}propionylamino)phenyl]cyclohexyl}acetic acid;
65) trans-{4-[4-(3-{[2-(2-Bromo-phenyl)-5-trifluoromethyloxazole-4-carbonyl]amino}propionylamino)phenyl]cyclohexyl}acetic acid;
66) trans-{4-[4-(3-{[5-trifluoromethyl-2-(2-trifluoromethylphenyl)oxazole-4-carbonyl]amino}propionylamino)phenyl]cyclohexyl}acetic acid;
67) trans-{4-[4-(3-{[2-(3-chlorophenyl)-5-trifluoromethyloxazole-4-carbonyl]amino}propionylamino)phenyl]cyclohexyl}acetic acid;
68) trans-{4-[4-(3-{[2-(2,6-dichlorophenyl)-5-trifluoromethyloxazole-4-carbonyl]amino}propionylamino)phenyl]cyclohexyl}acetic acid;
69) sodium; trans-{4-[4-(3-{[2-(2,6-dichlorophenyl)-5-trifluoromethyloxazole-4-carbonyl]amino}propionylamino)phenyl]cyclohexyl}acetate;
70) trans-{4-[4-(3-{[2-(2-chlorophenyl)-5-methyloxazole-4-carbonyl]amino}propionylamino)phenyl]cyclohexyl}acetic acid;
71) trans-{4-[4-(3-{[2-(2-methoxyphenyl)-5-trifluoromethyloxazole-4-carbonyl]amino}propionylamino)phenyl]cyclohexyl}acetic acid;
72) trans-{4-[4-(3-{[2-(2,6-difluorophenyl)-5-trifluoromethyloxazole-4-carbonyl]amino}propionylamino)phenyl]cyclohexyl}acetic acid;
73) trans-{4-[4-(3-{[2-(2-chloro-6-fluorophenyl)-5-trifluoromethyloxazole-4-carbonyl]amino}propionylamino)phenyl]cyclohexyl}acetic acid;
74) trans-[4-(4-{3-[(2'-methylbiphenyl-4-carbonyl)amino]propionylamino}phenyl)cyclohexyl]acetic acid;
75) trans-[4-(4-(3-(2',6'-dimethylbiphenyl-4-carbonylamino)propionylamino)phenyl)cyclohexyl]acetic add;
76) trans-[4-(4-{3-[4-(4-carboxymethylcyclohexyl)benzoylamino]propionylamino}phenyl)cyclohexyl]acetic add;
77) trans-{4-[4-(3-{[2-(2-nitrophenyl)-5-trifluoromethyloxazole-4-carbonyl]amino}-propionylamino)phenyl]cyclohexyl}acetic add;
78) trans-[4-(4-{3-[(biphenyl-4-carbonyl)amino]propionylamino}phenyl)cyclohexyl]acetic acid;
79) sodium; trans-{4-[4-(3-{[2-(2-chlorophenyl)-5-trifluoromethyloxazole-4-carbonyl]amino}propionylamino)phenyl]cyclohexyl}acetate;
80) trans-[4-(4-{3-[(naphthalene-2-carbonyl)amino]propionylamino}phenyl)cyclohexyl]acetic acid;
81) trans-4-(4-{2-[4-(4-methoxycarbonylmethylcyclohexyl)phenylcarbamoyl]ethylcarbamoyl}phenoxy)cyclohexanecarboxylic acid ethyl ester;
82) cis,trans-4-(4-{2-[4-(4-carboxymethylcyclohexyl)phenylcarbamoyl]ethylcarbamoyl}phenoxy)cyclohexanecarboxylic acid;
83) trans-[4-(4-{3-[(4-fluoro-naphthalene-1-carbonyl)amino]propionylamino}phenyl)cyclohexyl]acetic acid;
84) trans-[4-(4-(3-(2',6'-dichlorobiphenyl-4-carbonylamino)propionylamino)phenyl)cyclohexyl]acetic acid;
85) trans-{4-[4-(3-{[3-(2-chloro-6-fluorophenyl)-5-methylisoxazole-4-carbonyl]amino}propionylamino)phenyl]cyclohexyl}-acetic acid;
86) trans-[4-(4-{3-[(2'-chloro-biphenyl-4-carbonyl)amino]propionylamino}phenyl)cyclohexyl]acetic acid;
87) trans-[4-(4-{3-[(5-chloro-2-phenyloxazole-4-carbonyl)amino]propionylamino}phenyl)cyclohexyl]acetic acid;
88) trans-[4-(4-(3-(2',6'-difluorobiphenyl-4-carbonylamino)propionylamino)phenyl)cyclohexyl]acetic acid;

89) trans-[4-(4-(3-(2',4'-difluorobiphenyl-4-carbonylamino)propionylamino)phenyl)cyclohexyl]acetic acid;
90) trans-[4-(4-(3-(2'-ethylbiphenyl-4-carbonylamino)propionylamino)phenyl)cyclohexyl]acetic acid;
91) trans-[4-(4-{3-[(2-phenyloxazole-4-carbonyl)amino]propionylamino}phenyl)cyclohexyl]acetic acid;
92) trans-[4-(4-{3-[(5-phenylpyridine-3-carbonyl)amino]propionylamino}phenyl)cyclohexyl]acetic acid;
93) trans-[4-(4-{3-[(4'-ethylbiphenyl-4-carbonyl)amino]propionylamino}phenyl)cyclohexyl]acetic acid;
94) trans-[4-(4-{3-[(2-chlorobiphenyl-4-carbonyl)amino]propionylamino}phenyl)cyclohexyl]acetic acid;
95) trans-{4-[4-(3-{[5-chloro-2-(2-chlorophenyl)oxazole-4-carbonyl]amino}propionylamino)phenyl]cyclohexyl}acetic acid;
96) trans-(4-{4-[3-(4-pyrimidin-5-ylbenzoylamino)propionylamino]phenyl}cyclohexyl)acetic acid;
97) trans-(4-{4-[3-(4-pyrimidin-2-ylbenzoylamino)propionylamino]phenyl}cyclohexyl)acetic acid;
98) trans-{4-[4-(3-{[5-chloro-2-(2,4,5-trifluorophenyl)oxazole-4-carbonyl]amino}propionylamino)phenyl]cyclohexyl}acetic acid;
99) trans-[4-(4-{3-[(2-trifluoromethylbiphenyl-4-carbonyl)amino]propionylamino}phenyl)cyclohexyl]acetic acid;
100) trans-[4-(4-{3-[(6-phenylpyridine-3-carbonyl)amino]propionylamino}phenyl)cyclohexyl]acetic acid;
101) trans-{4-[4-(3-{[6-(2-trifluoromethylphenyl)pyridine-3-carbonyl]amino}propionylamino)phenyl]cyclohexyl}acetic acid;
102) trans-{4-[4-(3-{[2-(2,4,5-trifluorophenyl)oxazole-4-carbonyl]amino}propionylamino)phenyl]cyclohexyl}acetic acid;
103) trans-{4-[4-(3-{[2-(2-iodophenyl)-5-trifluoromethyloxazole-4-carbonyl]amino}propionylamino)phenyl]cyclohexyl}acetic acid;
104) trans-{4-[4-(3-{[2-(2-chlorophenyl)oxazole-4-carbonyl]amino}propionylamino)phenyl]cyclohexyl}acetic acid; and
105) trans-(4-(4-(3-(2-(2,6-dichloro-4-fluorophenyl)-5-(trifluoromethyl)oxazole-4-carboxamido)propanamido)phenyl)cyclohexyl)acetic acid.

6. The beta-alanine derivative or pharmaceutically acceptable salts thereof of claim 5, wherein the beta-alanine derivative is selected from the group consisting of:
4) trans-(4-{4-[3-(4-ethoxybenzoylamino)propionylamino]phenyl}cyclohexyl)acetic acid;
6) trans-[4-(4-{3-[(2-phenyl-5-trifluoromethyloxazole-4-carbonyl)amino]propionylamino}phenyl)cyclohexyl]acetic acid;
11) trans-{4-[4-(3-{[2-(2-chlorophenyl)-5-trifluoromethyloxazole-4-carbonyl]amino}propionylamino)phenyl]cyclohexyl}acetic acid;
41) trans-2-phenyl-5-trifluoromethyloxazole-4-carboxylic acid{2-[4-(4-carbamoylmethylcyclohexyl)phenylcarbamoyl]ethyl}amide;
60) trans-{4-[4-(3-{[2-(2-fluorophenyl)-5-trifluoromethyloxazole-4-carbonyl]amino}propionylamino)phenyl]cyclohexyl}acetic acid;
64) trans-{4-[4-(3-{[2-(2,4-dichlorophenyl)-5-trifluoromethyloxazole-4-carbonyl]amino}propionylamino)phenyl]cyclohexyl}acetic acid;
65) trans-{4-[4-(3-{[2-(2-bromophenyl)-5-trifluoromethyloxazole-4-carbonyl]amino}propionylamino)phenyl]cyclohexyl}acetic acid;
66) trans-{4-[4-(3-{[5-trifluoromethyl-2-(2-trifluoromethylphenyl)oxazole-4-carbonyl]amino}propionylamino)phenyl]cyclohexyl}acetic acid;
68) trans-{4-[4-(3-{[2-(2,6-dichlorophenyl)-5-trifluoromethyloxazole-4-carbonyl]amino}propionylamino)phenyl]cyclohexyl}acetic acid;
69) sodium; trans-{4-[4-(3-{[2-(2,6-dichlorophenyl)-5-trifluoromethyloxazole-4-carbonyl]amino}propionylamino)phenyl]cyclohexyl}acetate;
79) sodium; trans-{4-[4-(3-{[2-(2-chlorophenyl)-5-trifluoromethyloxazole-4-carbonyl]amino}propionylamino)phenyl]cyclohexyl}acetate;
93) trans-[4-(4-{3-[(4'-ethylbiphenyl-4-carbonyl)amino]propionylamino}phenyl)cyclohexyl]acetic acid;
94) trans-[4-(4-{3-[(2-chlorobiphenyl-4-carbonyl)amino]propionylamino}phenyl)cyclohexyl]acetic acid;
95) trans-{4-[4-(3-{[5-chloro-2-(2-chlorophenyl)-oxazole-4-carbonyl]amino}propionylamino)phenyl]cyclohexyl}acetic acid; and
105) trans-(4-(4-(3-(2-(2,6-dichloro-4-fluorophenyl)-5-(trifluoromethyl)oxazole-4-carboxamido)propanamido)phenyl)cyclohexyl)acetic acid.

7. A pharmaceutical composition, comprising the beta-alanine derivative of claim 1, the pharmaceutically acceptable salts thereof or a solvate thereof, as an active ingredient.

8. The pharmaceutical composition of claim 7, further comprising at least one pharmaceutical agent selected from the group consisting of anti-obesity agents and anti-diabetic agents.

* * * * *